United States Patent

(12) United States Patent
Witter et al.

(10) Patent No.: US 10,399,972 B2
(45) Date of Patent: *Sep. 3, 2019

(54) TRICYCLIC COMPOUNDS AS INHIBITORS OF MUTANT IDH ENZYMES

(71) Applicant: Merck Sharp & Dohme Corp., Rahway, NJ (US)

(72) Inventors: David J. Witter, Norfolk, MA (US); Tesfaye Biftu, Freehold, NJ (US); Purakkattle Biju, Westwood, MA (US); Stephane L. Bogen, Somerset, NJ (US); Qingmei Hong, Scotch Plains, NJ (US); Chunhui Huang, Arlington, MA (US); Xianhai Huang, Warren, NJ (US); Bing Li, Towaco, NJ (US); Min K. Park, Whippany, NJ (US); David L. Sloman, Brookline, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/769,414

(22) PCT Filed: Oct. 25, 2016

(86) PCT No.: PCT/US2016/058614

§ 371 (c)(1),
(2) Date: Apr. 19, 2018

(87) PCT Pub. No.: WO2017/074914

PCT Pub. Date: May 4, 2017

(65) Prior Publication Data

US 2018/0305352 A1  Oct. 25, 2018

Related U.S. Application Data

(60) Provisional application No. 62/247,930, filed on Oct. 29, 2015.

(51) Int. Cl.
| | |
|---|---|
| *A61K 31/551* | (2006.01) |
| *A61K 31/4353* | (2006.01) |
| *C07D 471/04* | (2006.01) |
| *C07D 519/00* | (2006.01) |
| *A61P 35/02* | (2006.01) |
| *C07D 491/10* | (2006.01) |
| *C07D 498/08* | (2006.01) |

(52) U.S. Cl.
CPC ............ *C07D 471/04* (2013.01); *A61P 35/02* (2018.01); *C07D 491/10* (2013.01); *C07D 498/08* (2013.01); *C07D 519/00* (2013.01)

(58) Field of Classification Search
CPC .............. A61K 31/551; A61K 31/4353; C07D 471/04; C07D 519/00

USPC ............ 514/220, 293; 546/82; 540/578, 586
See application file for complete search history.

(56) References Cited

U.S. PATENT DOCUMENTS

| | | | |
|---|---|---|---|
| 3,903,134 | A | 9/1975 | Diamond |
| 5,354,747 | A | 10/1994 | Hansen, Jr. et al. |
| 6,194,407 | B1 | 2/2001 | Failli et al. |
| 2002/0198191 | A1 | 12/2002 | Failli et al. |
| 2017/0369507 | A1 * | 12/2017 | Christian ............. A61K 31/551 |

FOREIGN PATENT DOCUMENTS

| | | | | |
|---|---|---|---|---|
| WO | WO-9631111 A1 * | 10/1996 | ........... | C07D 401/12 |
| WO | 2014141153 A1 | 9/2014 | | |
| WO | WO-2016089797 A1 * | 6/2016 | ........... | A61K 31/551 |

OTHER PUBLICATIONS

International Search Report, PCT/US2016/58614, dated Feb. 16, 2017, 8 pages.
Shen, J et al, Selective Inhibition of Mutant Isocitrate Dehydrogenase 1 (IDH1) via Disruption of a Metal Binding Network by an Allosteric Small Molecule Gejing Deng 1, The Journal of Biological Chemistry vol. 2015, 762-774, vol. 290.

* cited by examiner

*Primary Examiner* — Matthew P Coughlin
*Assistant Examiner* — Sagar Patel
(74) *Attorney, Agent, or Firm* — Yong Zhao; Catherine D. Fitch

(57) ABSTRACT

The present invention is directed to tricyclic compounds of formula (I), (Ia) or (Ib) which are inhibitors of one or more mutant IDH enzymes. The present invention is also directed to uses of these tricyclic compounds in the potential treatment or prevention of cancers in which one or more mutant IDH enzymes are involved. The present invention is also directed to compositions comprising these compounds. The present invention is also directed to uses of these compositions in the potential prevention or treatment of such cancers.

19 Claims, No Drawings

TRICYCLIC COMPOUNDS AS INHIBITORS OF MUTANT IDH ENZYMES

CROSS-REFERENCE TO RELATED APPLICATIONS

The present application is a 371 national phase application of international application no. PCT/US2016/058614, filed Oct. 25, 2016, which claims the benefit of U.S. Provisional Application No. 62/247,930, filed Oct. 29, 2015; hereby incorporated by reference in its entirety.

BACKGROUND OF THE INVENTION

Isocitrate dehydrogenase (IDH) is a family of enzymes found in cellular metabolism. They are $NADP^+/NAD^+$ and metal dependent oxidoreductases of the enzyme class EC 1.1.1.42. The wild type proteins catalyze the oxidative decarboxylation of isocitrate to alpha-ketoglutarate, generating carbon dioxide and NADPH/NADH in the process. They are also known to convert oxalosuccinate into alpha-ketoglutarate. Mutations in IDH1 (cytosolic) and IDH2 (mitochondrial) have been identified in multiple cancer types including, but not limited to, glioma, glioblastoma multiforme, paraganglioma, supratentorial primordial neuroectodermal tumors, acute myeloid leukemia (AML), prostate cancer, thyroid cancer, colon cancer, chondrosarcoma, cholangiocarcinoma, peripheral T-cell lymphoma, and melanoma. (See L. Dang et al., Trends Mol. Med., 2010, 16, 387; T. Shibata et al., Am. J. Pathol., 2011, 178(3), 1395; Gaal et al., J. Clin. Endocrinol. Metab. 2010, 95(3), 1274; Balss et al., Acta Neuropathol., 2008, 116, 597). The mutations have been found at or near key residues in the active site: G97D, R100Q, R132H, H133Q, and A134D for IDH1, and R140 and R172 for IDH2. (See L. Dang et al., Nature, 2009, 462, 739; L. Sellner et al., Eur. J. Haematol., 2010, 85, 457).

These mutant forms of IDH are believed to have a neomorphic activity, reducing alpha-ketoglutarate to 2-hydroxyglutarate (2-HG). (See P. S. Ward et al., Cancer Cell, 2010, 17, 225) In general, production of 2-HG is enantiospecific, resulting in generation of the D-enantiomer (also known as the R enantiomer or R-2-HG). Normal cells generally have low native levels of 2-HG, whereas cells harboring these mutations in IDH1 or IDH2 show significantly elevated levels of 2-HG. High levels of 2-HG have also been detected in tumors harboring the mutations. High levels of 2-HG have been detected in the plasma of patients with mutant IDH containing AML. (See S. Gross et al., J. Exp. Med., 2010, 207(2), 339).

Mutations in IDH1 have been associated with multiple cancers and patients having these disorders often have increased levels of 2-HG in their urine, plasma or cerebrospinal fluid. (See M. Kranendijk et al., Science, 2010, 330, 336) There is a continuing need for small molecule inhibitors of mutant IDH enzymes, or more specifically IDH1 enzymes, for the treatment of diseases and disorders associated with these enzymes.

SUMMARY OF THE INVENTION

Disclosed herein are novel tricyclic compounds of formula (I), (Ia) or (Ib) which are inhibitors of one or more mutant IDH enzymes. Also disclosed herein are uses of these novel tricyclic compounds in the potential treatment or prevention of cancers in which one or more mutant IDH enzymes are involved. Also disclosed herein are compositions comprising these compounds. Further disclosed herein are uses of these compositions in the potential prevention or treatment of such cancers.

DETAILED DESCRIPTION OF THE INVENTION

Disclosed herein is a compound of formula I, or a pharmaceutically acceptable salt thereof:

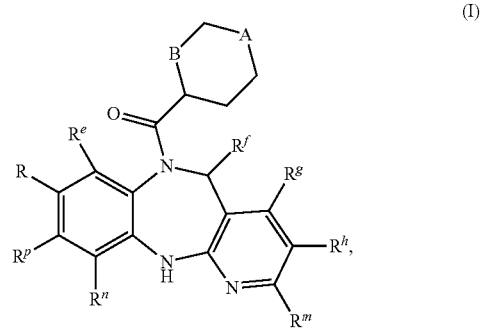

(I)

wherein
A is —CH($R^1$)— or —N($R^2$)—; $R^1$ is selected from the group consisting of hydrogen, —O—$C_{1-10}$alkyl, and $C_{1-10}$alkyl optionally substituted with one to four halogens; and $R^2$ is selected from the group consisting of hydrogen, —S(O)$_2$—$C_{1-4}$alkyl, and $C_{1-10}$alkyl optionally substituted with one to four halogens;
B is —CH$_2$— or —O—;
R is selected from the group consisting of:
 (1) hydrogen,
 (2) halogen,
 (3) —$C_{1-10}$alkyl,
 (4) —O—$C_{1-10}$alkyl,
 (5) —N$R^xR^y$, wherein each of $R^x$ and $R^y$ is independently selected from the group consisting of (a) hydrogen and (b) $C_{1-6}$alkyl, optionally substituted with one to four substituents independently selected from halogen and heterocyclyl; wherein the heterocyclyl is optionally substituted with one to four substituents independently selected from methyl, ethyl, propyl, butyl, —CH$_2$—Cl, —CH$_2$—F, —CH$_2$CH$_2$—Cl, —CH$_2$CH$_2$—F, and —CH$_2$CF$_3$; and
 (6) heterocyclyl, optionally substituted with one to four substituents independently selected from halogen, hydroxyl, —$C_{1-10}$alkyl, and —O—$C_{1-10}$alkyl;
$R^e$ is selected from the group consisting of:
 (1) hydrogen,
 (2) halogen, and
 (3) $C_{1-6}$alkyl; and
each of $R^f$, $R^g$, $R^h$, $R^m$, $R^n$ and $R^p$ is independently selected from the group consisting of:
 (1) hydrogen,
 (2) halogen,
 (3) $C_{1-6}$alkyl, and
 (4) —S(O)$_2$—$C_{1-4}$alkyl;
 with the proviso that when $R^e$ is hydrogen, at least one of $R^f$, $R^g$, $R^h$, $R^m$, $R^n$ and $R^p$ is not hydrogen.

In one embodiment of the compounds of formula (I), each occurrence of a heterocyclyl is independently selected from the group consisting of 2-azabicyclo[2.2.2]octanyl, 8-azabicyclo[3.2.1]octanyl, 2-azaspiro[3.3]heptanyl, azaindolyl, 1,6-diazaspiro[3.3]heptanyl, 2,3-dihydro-1,4-dioxinyl, 1,4- dioxanyl, hexahydro-3,6-epiminofuro[3,2-b]furanyl, hexahydro-1H-furo[3,4-c]pyrrolyl, imidazolyl, isoxazolyl, morpholinyl, 2-oxa-5-azabicyclo[2.2.1]heptanyl, 6-oxa-3-azabicyclo[3.1.1]heptanyl, 6-oxa-2-azaspiro[3.5]nonanyl, 2-oxa-5-azabicyclo[2.2.2]octanyl, 3-oxa-8-azabicyclo[3.2.1]octanyl, 8-oxa-3-azabicyclo[3.2.1]octanyl, 1-oxa-8-azaspiro[4.5]decanyl, 6-oxa-2-azaspiro[3.4]octanyl, 3-oxa-1,7-diazaspiro[4.4]nonanyl, 3,9-dioxa-7-azabicyclo[3.3.1]nonanyl, oxazolidinyl, piperazinyl, piperidinyl, pyrazolyl, pyridazinyl, pyridinyl, pyrimidinyl, pyrrolidinyl, pyrrolyl, tetrahydrofuranyl and tetrahydropyranyl.

In one embodiment of the compounds of formula (I), each occurrence of a heterocyclyl is independently selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl, pyrazolyl, and tetrahydropyranyl.

In one embodiment of the compounds of formula (I):
A is —CH($R^1$)— or —N($R^2$)—; $R^1$ is selected from the group consisting of hydrogen, —$C_{1-6}$alkyl and —O—$C_{1-6}$alkyl; $R^2$ is selected from the group consisting of hydrogen, methyl, ethyl, propyl, butyl, —$CH_2CF_3$, and —$S(O)_2$—$C_{1-4}$alkyl; and
B is —$CH_2$— or —O—.

In an embodiment of each previous embodiment of formula (I):
A is —CH($R^1$)— or —N($R^2$)—; $R^1$ is selected from the group consisting of hydrogen, methyl, ethyl, propyl, —O-methyl, —O-ethyl, —O-propyl and —O-isopropyl; $R^2$ is selected from the group consisting of hydrogen, —$CH_2CF_3$, and —$S(O)_2$-ethyl; and
B is —$CH_2$— or —O—.

In an embodiment of each previous embodiment of formula (I):
R is selected from the group consisting of:
(1) hydrogen,
(2) halogen,
(3) —$C_{1-6}$alkyl,
(4) —O—$C_{1-6}$alkyl,
(5) —NH$R^y$, wherein $R^y$ is selected from the group consisting of (a) hydrogen and (b) $C_{1-4}$alkyl, optionally substituted with one to four substituents independently selected from halogen and heterocyclyl; wherein the heterocyclyl is optionally substituted with methyl, ethyl, propyl, —$CH_2$—Cl, —$CH_2$—F, or —$CH_2CF_3$; and
(6) heterocyclyl, optionally substituted with one to four substituents independently selected from halogen, hydroxyl, —$C_{1-6}$alkyl, and —O—$C_{1-6}$alkyl.

In an embodiment of each previous embodiment of formula (I):
R is selected from the group consisting of:
(1) hydrogen,
(2) halogen,
(3) —O—$C_{1-4}$alkyl,
(4) —NH—$C_{1-2}$alkyl, wherein the —$C_{1-2}$alkyl is substituted with a heterocyclyl; wherein the heterocyclyl is optionally substituted with methyl, ethyl, propyl, —$CH_2$Cl or —$CH_2CF_3$; and
(5) heterocyclyl, optionally substituted with one to four substituents independently selected from halogen, $C_{1-4}$alkyl, and —O—$C_{1-4}$alkyl;
wherein each occurrence of the heterocyclyl of (4) and (5) is independently selected from the group consisting of 2-azabicyclo[2.2.2]octanyl, 8-azabicyclo[3.2.1]octanyl, 2-azaspiro[3.3]heptanyl, azaindolyl, 1,6-diazaspiro[3.3]heptanyl, 2,3-dihydro-1,4-dioxinyl, 1,4-dioxanyl, hexahydro-3,6-epiminofuro[3,2-b]furanyl, hexahydro-1H-furo[3,4-c]pyrrolyl, imidazolyl, isoxazolyl, morpholinyl, 2-oxa-5-azabicyclo[2.2.1]heptanyl, 6-oxa-3-azabicyclo[3.1.1]heptanyl, 6-oxa-2-azaspiro[3.5]nonanyl, 2-oxa-5-azabicyclo[2.2.2]octanyl, 3-oxa-8-azabicyclo[3.2.1]octanyl, 8-oxa-3-azabicyclo[3.2.1]octanyl, 1-oxa-8-azaspiro[4.5]decanyl, 6-oxa-2-azaspiro[3.4]octanyl, 3-oxa-1,7-diazaspiro[4.4]nonanyl, 3,9-dioxa-7-azabicyclo[3.3.1]nonanyl, oxazolidinyl, piperazinyl, piperidinyl, pyrazolyl, pyridazinyl, pyridinyl, pyrrolyl, tetrahydrofuranyl, and tetrahydropyranyl.

In an embodiment of each previous embodiment of formula (I):
R is selected from the group consisting of:
(1) hydrogen,
(2) —F,
(3) —Cl,
(4) —Br,
(5) —O-methyl,
(6) —O-ethyl,
(7) —NH—$CH_2$-heterocyclyl, wherein the heterocyclyl is substituted with —$CH_2$Cl, and
(8) heterocyclyl, optionally substituted with one to two substituents independently selected from F, —Cl, methyl, ethyl, propyl, —O-methyl, —O-ethyl, and —O-propyl;
wherein each occurrence of the heterocyclyl of (7) and (8) is independently selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl, pyrazolyl, and tetrahydropyranyl.

In an embodiment of each previous embodiment of formula (I):
R is selected from the group consisting of:
(1) hydrogen,
(2) —F,
(3) —Cl,
(4) —Br,
(5) —O-methyl,
(6) —O-ethyl,
(7) —NH—$CH_2$-tetrahydropyranyl, wherein the tetrahydropyranyl is substituted with —$CH_2$Cl, and
(8) heterocyclyl, optionally substituted with one to two substituents independently selected from —Cl, —F, methyl, ethyl, propyl, —O-methyl, —O-ethyl, and —O-propyl;
wherein the heterocyclyl is selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl and pyrazolyl.

In an embodiment of each previous embodiment of formula (I):
$R^e$ is hydrogen, —F, —Cl, methyl or ethyl; and
each of $R^f$, $R^g$, $R^h$, $R^m$, $R^n$ and $R^p$ is independently selected from the group consisting of:
(1) hydrogen,
(2) —F, (3) —Cl,
(4) —Br,
(5) methyl,
(6) ethyl,
(7) propyl, and
(8) —S(O)$_2$—C$_{1-2}$alkyl;
with the proviso that when R$^e$ is hydrogen, at least one of R$^f$, R$^g$, R$^h$, R$^m$, R$^g$ and R$^p$ is not hydrogen.

In an embodiment of each previous embodiment of formula (I):
R$^e$ is —F, —Cl, methyl or ethyl; and
each of R$^f$, R$^g$, R$^h$, R$^m$, R$^n$ and R$^p$ is hydrogen.

In an embodiment of each previous embodiment of formula (I):
R$^e$ is hydrogen; and
each of R$^f$, R$^g$, R$^h$, R$^m$, R$^n$ and R$^p$ is independently selected from the group consisting of:
(1) —F,
(2) —Cl,
(3) —Br,
(4) methyl,
(5) ethyl, and
(6) —S(O)$_2$-methyl.

In an embodiment of each previous embodiment of formula (I):
A is —CH(R$^1$)— or —N(R$^2$)—; R$^1$ is selected from the group consisting of hydrogen, methyl, —O— methyl, —O-ethyl and —O-propyl and —O-isopropyl; R$^2$ is selected from the group consisting of hydrogen, —CH$_2$CF$_3$, and —S(O)$_2$-ethyl;
B is —CH$_2$— or —O—;
R is selected from the group consisting of:
(1) hydrogen,
(2) —F,
(3) —Cl,
(4) —O-methyl,
(5) —O-ethyl,
(6) —NH—CH$_2$-tetrahydropyranyl, wherein the tetrahydropyranyl is substituted with —CH$_2$Cl, and
(7) heterocyclyl, optionally substituted with one to two substituents independently selected from —Cl, —F, methyl, ethyl, propyl, —O-methyl, —O-ethyl, —O-propyl and —O-isopropyl;
  wherein the heterocyclyl is selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl and pyrazolyl;
R$^e$ is hydrogen, —Cl, —F, methyl or ethyl; and
each of R$^f$, R$^g$, R$^h$, R$^m$, R$^n$ and R$^p$ is independently selected from the group consisting of:
(1) hydrogen,
(2) —F,
(3) —Cl,
(4) —Br,
(5) methyl,
(6) ethyl,
(7) propyl, and
(8) —S(O)$_2$-methyl;
with the proviso that when R$^e$ is hydrogen, at least one of R$^f$, R$^g$, R$^h$, R$^m$, R$^n$ and R$^p$ is not hydrogen.

In one embodiment, a compound disclosed herein is of formula (Ia), or a pharmaceutically acceptable salt thereof:

(Ia)

wherein
A is —CH(R$^1$)— or —N(R$^2$)—; R$^1$ is selected from the group consisting of hydrogen, methyl, —O— propyl and —O-isopropyl; R$^2$ is —CH$_2$CF$_3$ or —S(O)$_2$-ethyl;
R$^e$ is hydrogen, —Cl, —F, methyl or ethyl; and
each of R$^f$, R$^g$, R$^h$, R$^m$, R$^n$ and R$^p$ is independently selected from the group consisting of:
(1) hydrogen,
(2) —F,
(3) —Cl,
(4) —Br,
(5) methyl,
(6) ethyl,
(7) propyl, and
(8) —S(O)$_2$-methyl;
with the proviso that when R$^e$ is hydrogen, at least one of R$^f$, R$^g$, R$^h$, R$^m$, R$^n$ and R$^p$ is not hydrogen; and
R is as defined for formula (I).

In an embodiment of the compounds of formula (Ia), or a pharmaceutically acceptable salt thereof:
R$^e$ is —F or methyl; and
each of R$^f$, R$^g$, R$^h$, R$^m$, R$^n$ and R$^p$ is hydrogen.

In an embodiment of the compounds of formula (Ia), or a pharmaceutically acceptable salt thereof:
R$^e$ is hydrogen;
each of R$^m$ and R$^h$ is hydrogen; and
each of R$^f$, R$^g$, R$^h$, and R$^p$ is independently selected from the group consisting of:
(1) hydrogen,
(2) —F,
(3) —Cl,
(4) methyl, and
(5) —S(O)$_2$-methyl;
with the proviso that at least one of R$^f$, R$^g$, R$^h$ and R$^p$ is not hydrogen.

In one embodiment, a compound disclosed herein is of formula (Ib), or a pharmaceutically acceptable salt thereof:

(Ib)

wherein
A is —CH(R¹)—; and R¹ is —O-propyl or —O-isopropyl;
R$^e$ is hydrogen;
each of R$^f$, R$^g$, R$^m$ and R$^n$ is hydrogen;
each of R$^h$ and R$^p$ is independently selected from the group consisting of:
(1) hydrogen,
(2) —F, and
(3) —Cl;
with the proviso that at least one of R$^h$ and R$^p$ is not hydrogen; and
R is as defined for formula (I).

In one embodiment of formula (Ib) above, R is a heterocyclyl selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl and pyrazolyl.

In one embodiment, a compound disclosed herein is of formula (Ib), or a pharmaceutically acceptable salt thereof, wherein:
A is —CH(R¹)—; and R¹ is —O-propyl or —O-isopropyl;
R$^e$ is hydrogen;
each of R$^f$, R$^g$, R$^m$ and R$^n$ is hydrogen;
each of R$^h$ and R$^p$ is independently selected from the group consisting of:
(1) hydrogen,
(2) —F, and
(3) —Cl;
with the proviso that at least one of R$^h$ and R$^p$ is not hydrogen; and R is a heterocyclyl selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl and pyrazolyl.

In one embodiment, a compound disclosed herein is of formula (Ib), or a pharmaceutically acceptable salt thereof, wherein:
A is —CH(R¹)—; and R¹ is —O-propyl or —O-isopropyl;
R$^e$ is hydrogen;
each of R$^f$, R$^g$, R$^m$, R$^n$ and R$^p$ is hydrogen;
R$^h$ is —F or Cl; and
R is a heterocyclyl selected from the group consisting of 1,4-dioxanyl, morpholinyl, oxazolidinyl and pyrazolyl.

In one embodiment, a compound is selected from the group consisting of:
(8-Chloro-3-fluoro-5,11-dihydro-6H-benzo[b]pyrido[2,3-e][1,4]diazepin-6-yl)(1-(2,2,2-trifluoroethyl)piperidin-4-yl)methanone,
(8-Chloro-3-fluoro-5,11-dihydro-6H-benzo[b]pyrido[2,3-e][1,4]diazepin-6-yl)(trans-4-isopropoxycyclohexyl)methanone,
(8-Bromo-3-fluoro-5,11-dihydro-6H-benzo[b]pyrido[2,3-e][1,4]diazepin-6-yl)(trans-4-isopropoxycyclohexyl)methanone,
(8-Chloro-3,9-difluoro-5,11-dihydro-6H-benzo[b]pyrido[2,3-e][1,4]diazepin-6-yl)(trans-4-isopropoxycyclohexyl)methanone,
(8-Chloro-3,9-difluoro-5,11-dihydro-6H-benzo[b]pyrido[2,3-e][1,4]diazepin-6-yl)(1-(2,2,2-trifluoroethyl)piperidin-4-yl)methanone,
(8-((1S,4S)-2-Oxa-5-azabicyclo[2.2.1]heptan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone,
(3-Fluoro-8-((3R,3aR,6R,6aR)-hexahydro-3,6-epiminofuro[3,2-b]furan-7-yl)-5,11-dihydro-6H-benzo[b]pyrido[2,3-e][1,4]diazepin-6-yl)(1-(2,2,2-trifluoroethyl)piperidin-4-yl)methanone,
(8-(2-Oxa-5-azabicyclo[2.2.2]octan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone,
(8-(2-Oxa-5-azabicyclo[2.2.2]octan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone,
(3-Fluoro-8-((1R,3r,5S)-3-methoxy-8-azabicyclo[3.2.1]octan-8-yl)-5,11-dihydro-6H-benzo[b]pyrido[2,3-e][1,4]diazepin-6-yl)(1-(2,2,2-trifluoroethyl)piperidin-4-yl)methanone,
(8-((2S,5S)-2,5-Dimethylmorpholino)-3-fluoro-5,11-dihydro-6H-benzo[b]pyrido[2,3-e][1,4]diazepin-6-yl)(1-(2,2,2-trifluoroethyl)piperidin-4-yl)methanone,
(3-Fluoro-8-(6-oxa-2-azaspiro[3.5]nonan-2-yl)-5,11-dihydro-6H-benzo[b]pyrido[2,3-e][1,4]diazepin-6-yl)(1-(2,2,2-trifluoroethyl)piperidin-4-yl)methanone,
[3-Fluoro-8-(2-oxa-5-azabicyclo[2.2.2]oct-5-yl)-5,11-dihydro-6H-pyrido[2,3-b][1,5]benzodiazepin-6-yl][trans-4-(propan-2-yloxy)cyclohexyl]methanone,
[3-Fluoro-8-(2-oxa-5-azabicyclo[2.2.2]oct-5-yl)-5,11-dihydro-6H-pyrido[2,3-b][1,5]benzodiazepin-6-yl][trans-4-(propan-2-yloxy)cyclohexyl]methanone,
(8-41R,5S)-3,9-Dioxa-7-azabicyclo[3.3.1]nonan-7-yl)-3-fluoro-5,11-dihydro-6H-benzo[b]pyrido[2,3-e][1,4]diazepin-6-yl)(1-(2,2,2-trifluoroethyl)piperidin-4-yl)methanone,
[3-Fluoro-8-(6-oxa-2-azaspiro[3.5]non-2-yl)-5,11-dihydro-6H-pyrido[2,3-b][1,5]benzodiazepin-6-yl][trans-4-(propan-2-yloxy)cyclohexyl]methanone,
(3-Fluoro-8-((3R,3aR,6R,6aR)-hexahydro-3,6-epiminofuro[3,2-b]furan-7-yl)-5,11-dihydro-6H-benzo[b]pyrido[2,3-e][1,4]diazepin-6-yl)(trans-4-isopropoxycyclohexyl)methanone,
(8-((1S,4S)-2-Oxa-5-azabicyclo[2.2.1]heptan-5-yl)-3-fluoro-5,11-dihydro-6H-benzo[b]pyrido[2,3-e][1,4]diazepin-6-yl)(trans-4-isopropoxycyclohexyl)methanone,
(8-((1S,4S)-2-Oxa-5-azabicyclo[2.2.1]heptan-5-yl)-3-fluoro-5,11-dihydro-6H-benzo[b]pyrido[2,3-e][1,4]diazepin-6-yl)(cis-4-isopropoxycyclohexyl)methanone,
(8-((1S,4S)-2-Oxa-5-azabicyclo[2.2.1]heptan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone,
(3,9-Difluoro-8-(6-oxa-2-azaspiro[3.5]nonan-2-yl)-5,11-dihydro-6H-benzo[b]pyrido[2,3-e][1,4]diazepin-6-yl)(1-(2,2,2-trifluoroethyl)piperidin-4-yl)methanone,
(3,9-Difluoro-8-((3R,3aR,6R,6aR)-hexahydro-3,6-epiminofuro[3,2-b]furan-7-yl)-5,11-dihydro-6H-benzo[b]pyrido[2,3-e][1,4]diazepin-6-yl)(1-(2,2,2-trifluoroethyl)piperidin-4-yl)methanone,
(8-((2S,5S)-2,5-Dimethylmorpholino)-3,9-difluoro-5,11-dihydro-6H-benzo[b]pyrido[2,3-e][1,4]diazepin-6-yl)(1-(2,2,2-trifluoroethyl)piperidin-4-yl)methanone,
{3,9-Difluoro-8-[(1S,4S)-2-oxa-5-azabicyclo[2.2.1]hept-5-yl]-5,11-dihydro-6H-pyrido[2,3-b][1,5]benzodiazepin-6-yl}[trans-4-(propan-2-yloxy)cyclohexyl]methanone,
[3,9-Difluoro-8-(6-oxa-2-azaspiro[3.5]non-2-yl)-5,11-dihydro-6H-pyrido[2,3-b][1,5]benzodiazepin-6-yl][trans-4-(propan-2-yloxy)cyclohexyl]methanone,

[3,9-Difluoro-8-(3-oxa-8-azabicyclo[3.2.1]oct-8-yl)-5,11-dihydro-6H-pyrido[2,3-b][1,5]benzodiazepin-6-yl][trans-4-(propan-2-yloxy)cyclohexyl]methanone, (8-((1S,4S)-2-Oxa-5-azabicyclo[2.2.1]heptan-5-yl)-9-fluoro-5,11-dihydro-6H-benzo[b]pyrido[2,3-e][1,4]diazepin-6-yl)(1-(2,2,2-trifluoroethyl)piperidin-4-yl)methanone, (9-Fluoro-8-((3R,3aR,6R,6aR)-hexahydro-3,6-epiminofuro[3,2-b]furan-7-yl)-5,11-dihydro-6H-benzo[b]pyrido[2,3-e][1,4]diazepin-6-yl)(1-(2,2,2-trifluoroethyl)piperidin-4-yl)methanone, (8-(2-Oxa-5-azabicyclo[2.2.2]octan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone, (3,9-Difluoro-8-41R,3r,5S)-3-methoxy-8-azabicyclo[3.2.1]octan-8-yl)-5,11-dihydro-6H-benzo[b]pyrido[2,3-e][1,4]diazepin-6-yl)(1-(2,2,2-trifluoroethyl)piperidin-4-yl)methanone, (8-41R,4R)-2-Oxa-5-azabicyclo[2.2.2]octan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone, (8-((1S,4S)-2-Oxa-5-azabicyclo[2.2.2]octan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone, (8-((S)-1,4-Dioxan-2-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone, (8-((R)-1,4-dioxan-2-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone, (8-(1,4-Dioxan-2-yl)-3,9-difluoro-5H-benzo[b]pyrido[2,3-e][1,4]diazepin-6(11H)-yl)((2R,5S)-5-isopropoxytetrahydro-2H-pyran-2-yl)methanone, (8-(1,4-Dioxan-2-yl)-9-fluoro-5,11-dihydro-6H-benzo[b]pyrido[2,3-e][1,4]diazepin-6-yl)((2R,5S)-5-isopropoxytetrahydro-2H-pyran-2-yl)methanone, (8-(1,4-Dioxan-2-yl)-9-fluoro-5,11-dihydro-6H-benzo[b]pyrido[2,3-e][1,4]diazepin-6-yl)((2R,5S)-5-isopropoxytetrahydro-2H-pyran-2-yl)methanone, (3-Fluoro-8-((1R,3S,5S)-3-methoxy-8-azabicyclo[3.2.1]octan-8-yl)-5,11-dihydro-6H-benzo[b]pyrido[2,3-e][1,4]diazepin-6-yl)((2R,5S)-5-isopropoxytetrahydro-2H-pyran-2-yl)methanone, (3-Fluoro-8-(6-oxa-2-azaspiro[3.5]nonan-2-yl)-5,11-dihydro-6H-benzo[b]pyrido[2,3-e][1,4]diazepin-6-yl)((2R,5S)-5-isopropoxytetrahydro-2H-pyran-2-yl)methanone, (8-41R,5S)-3,9-Dioxa-7-azabicyclo[3.3.1]nonan-7-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone, (8-(((3-(Chloromethyl)tetrahydro-2H-pyran-3-yl)methyl)amino)-3-fluoro-5,11-dihydro-6H-benzo[b]pyrido[2,3-e][1,4]diazepin-6-yl)((2R,5S)-5-isopropoxytetrahydro-2H-pyran-2-yl)methanone, (8-(2-Oxa-5-azabicyclo[2.2.2]octan-5-yl)-3-fluoro-5,11-dihydro-6H-benzo[b]pyrido[2,3-e][1,4]diazepin-6-yl)(1-(ethylsulfonyl)piperidin-4-yl)methanone, (8-(2-Oxa-5-azabicyclo[2.2.2]octan-5-yl)-3,9-difluoro-5,11-dihydro-6H-benzo[b]pyrido[2,3-e][1,4]diazepin-6-yl)((2R,5S)-5-isopropoxytetrahydro-2H-pyran-2-yl)methanone, (3,9-Difluoro-8-(6-oxa-2-azaspiro[3.5]nonan-2-yl)-5H-benzo[b]pyrido[2,3-e][1,4]diazepin-6(11H)-yl)((2R,5S)-5-isopropoxytetrahydro-2H-pyran-2-yl)methanone, (8-((1S,4S)-2-Oxa-5-azabicyclo[2.2.1]heptan-5-yl)-3,9-difluoro-5,11-dihydro-6H-benzo[b]pyrido[2,3-e][1,4]diazepin-6-yl)((2R,5S)-5-isopropoxytetrahydro-2H-pyran-2-yl)methanone, (3,9-Difluoro-8-41R,3S,5S)-3-methoxy-8-azabicyclo[3.2.1]octan-8-yl)-5,11-dihydro-6H-benzo[b]pyrido[2,3-e][1,4]diazepin-6-yl)((2R,5S)-5-isopropoxytetrahydro-2H-pyran-2-yl)methanone, (8-41R,4R)-2-Oxa-5-azabicyclo[2.2.2]octan-5-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone, (8-((1S,4S)-2-Oxa-5-azabicyclo[2.2.2]octan-5-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone, (3,9-Difluoro-8-(1-methyl-1H-pyrazol-5-yl)-5,11-dihydro-6H-benzo[b]pyrido[2,3-e][1,4]diazepin-6-yl)(1-(2,2,2-trifluoroethyl)piperidin-4-yl)methanone, (3,9-Difluoro-8-(1H-pyrazol-5-yl)-5,11-dihydro-6H-benzo[b]pyrido[2,3-e][1,4]diazepin-6-yl)(1-(2,2,2-trifluoroethyl)piperidin-4-yl)methanone, (9-Fluoro-8-(1-methyl-1H-pyrazol-4-yl)-5,11-dihydro-6H-benzo[b]pyrido[2,3-e][1,4]diazepin-6-yl)(1-(2,2,2-trifluoroethyl)piperidin-4-yl)methanone, (9-Fluoro-8-(1-methyl-1H-pyrazol-5-yl)-5,11-dihydro-6H-benzo[b]pyrido[2,3-e][1,4]diazepin-6-yl)(1-(2,2,2-trifluoroethyl)piperidin-4-yl)methanone, (S)-(8-(1,4-Dioxan-2-yl)-3-fluoro-5,11-dihydro-6H-benzo[b]pyrido[2,3-e][1,4]diazepin-6-yl)(1-(2,2,2-trifluoroethyl)piperidin-4-yl)methanone, (R)-(8-(1,4-Dioxan-2-yl)-3-fluoro-5,11-dihydro-6H-benzo[b]pyrido[2,3-e][1,4]diazepin-6-yl)(1-(2,2,2-trifluoroethyl)piperidin-4-yl)methanone, (R)-(8-(1,4-Dioxan-2-yl)-9-fluoro-5,11-dihydro-6H-benzo[b]pyrido[2,3-e][1,4]diazepin-6-yl)(1-(2,2,2-trifluoroethyl)piperidin-4-yl)methanone, (S)-(8-(1,4-Dioxan-2-yl)-9-fluoro-5,11-dihydro-6H-benzo[b]pyrido[2,3-e][1,4]diazepin-6-yl)(1-(2,2,2-trifluoroethyl)piperidin-4-yl)methanone, (Trans-4-isopropoxycyclohexyl){9-methyl-8-[(1S,4S)-2-oxa-5-azabicyclo[2.2.2]oct-5-yl]-5,11-dihydro-6H-pyrido[2,3-b][1,5]benzodiazepin-6-yl}methanone, (Trans-4-isopropoxycyclohexyl){7-methyl-8-[(1S,4S)-2-oxa-5-azabicyclo[2.2.2]oct-5-yl]-5,11-dihydro-6H-pyrido[2,3-b][1,5]benzodiazepin-6-yl}methanone, (Trans-4-isopropoxycyclohexyl){9-methyl-8-[(1R,4R)-2-oxa-5-azabicyclo[2.2.2]oct-5-yl]-5,11-dihydro-6H-pyrido[2,3-b][1,5]benzodiazepin-6-yl}methanone, (Trans-4-isopropoxycyclohexyl){7-methyl-8-[(1R,4R)-2-oxa-5-azabicyclo[2.2.2]oct-5-yl]-5,11-dihydro-6H-pyrido[2,3-b][1,5]benzodiazepin-6-yl}methanone,

[9-Fluoro-8-(2-oxa-5-azabicyclo[2.2.2]oct-5-yl)-5,11-dihydro-6H-pyrido[2,3-b][1,5]benzodiazepin-6-yl](trans-4-isopropoxycyclohexyl)methanone,

[7-Fluoro-8-(2-oxa-5-azabicyclo[2.2.2]oct-5-yl)-5,11-dihydro-6H-pyrido[2,3-b][1,5]benzodiazepin-6-yl](trans-4-isopropoxycyclohexyl)methanone, (8-((1S,4S)-2-Oxa-5-azabicyclo[2.2.1]heptan-5-yl)-9-fluoro-5H-benzo[b]pyrido[2,3-e][1,4]diazepin-6(11H)-yl)((2R,5S)-5-isopropoxytetrahydro-2H-pyran-2-yl)methanone, (8-Chloro-5-methyl-5,11-dihydro-6H-benzo[b]pyrido[2,3-e][1,4]diazepin-6-yl)(trans-4-isopropoxycyclohexyl)methanone, (Trans-4-isopropoxycyclohexyl)(5-methyl-8-morpholino-5,
11-dihydro-6H-benzo[b]pyrido[2,3-e][1,4]diazepin-6-yl)
methanone,
(8-Methoxy-5-methyl-5,11-dihydro-6H-benzo[b]pyrido[2,
3-e][1,4]diazepin-6-yl)(1-(2,2,2-trifluoroethyl)piperidin-
4-yl)methanone,
(Trans-4-isopropoxycyclohexyl)(8-methoxy-5-methyl-5,11-
dihydro-6H-benzo[b]pyrido[2,3-e][1,4]diazepin-6-yl)
methanone,
(8-((1S,4S)-2-Oxa-5-azabicyclo[2.2.2]octan-5-yl)-3-
methyl-5,11-dihydro-6H-benzo[b]pyrido[2,3-e][1,4]diaz-
epin-6-yl)(trans-4-isopropoxycyclohexyl)methanone,
(8-((1S,4S)-2-Oxa-5-azabicyclo[2.2.2]octan-5-yl)-3-(meth-
ylsulfonyl)-5,11-dihydro-6H-benzo[b]pyrido[2,3-e][1,4]
diazepin-6-yl)(trans-4-isopropoxycyclohexyl)methanone,
(8-((1S,4S)-2-Oxa-5-azabicyclo[2.2.2]octan-5-yl)-3-chloro-
5,11-dihydro-6H-benzo[b]pyrido[2,3-e][1,4]diazepin-6-
yl)(trans-4-isopropoxycyclohexyl)methanone,
(3,9-Difluoro-5,11-dihydro-6H-benzo[b]pyrido[2,3-e][1,4]
diazepin-6-yl)(1-(2,2,2-trifluoroethyl)piperidin-4-yl)
methanone,
(8-(2-Oxa-5-azabicyclo[2.2.2]octan-5-yl)-3,9-difluoro-5H-
benzo[b]pyrido[2,3-e][1,4]diazepin-6(11H)-yl)(1-(2,2,2-
trifluoroethyl)piperidin-4-yl)methanone, and
(9-Fluoro-5,11-dihydro-6H-benzo[b]pyrido[2,3-e][1,4]diaz-
epin-6-yl)(1-(2,2,2-trifluoroethyl)piperidin-4-yl)metha-
none,
or a pharmaceutically acceptable salt thereof.

In one embodiment, a compound disclosed herein or a pharmaceutically acceptable salt thereof is used in medicine.

In one embodiment, disclosed herein is a composition which comprises an inert carrier or excipient and a compound of formula (I), (Ia) or (Ib), or a pharmaceutically acceptable salt thereof.

In one embodiment, disclosed herein is a method for treating or preventing a disease or disorder associated with mutant IDH enzyme activity in a subject which comprises administering to the subject an effective amount of a compound of formula (I), (Ia) or (Ib), or a pharmaceutically acceptable salt thereof.

In one embodiment, disclosed herein is the use of a compound of formula (I), (Ia), or (Ib), or a pharmaceutically acceptable salt thereof, for the manufacture of a medicament for the treatment or prevention of a disease or disorder associated with mutant IDH enzyme activity.

In one embodiment, a method for treating a disease or disorder associated with mutant IDH enzyme activity in a subject comprises administering to the subject an effective amount of a compound of formula (I), (Ia) or (Ib), or a pharmaceutically acceptable salt thereof, in combination with another anti-cancer agent.

In one embodiment, the disease or disorder associated with mutant IDH enzyme activity is cancer. In one embodiment, the cancer is selected from the group consisting of glioma, glioblastoma multiforme, paraganglioma, supratentorial primordial neuroectodermal tumors, acute myeloid leukemia (AML), breast cancer, prostate cancer, thyroid cancer, colon cancer, chondrosarcoma, cholangiocarcinoma, peripheral T-cell lymphoma, and melanoma. In one embodiment, the cancer is selected from glioma, glioblastoma multiforme, acute myeloid leukemia and breast cancer.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Halo" or "halogen" refers to fluoro, chloro, bromo or iodo, unless otherwise noted.

"Heterocycle" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, furanyl, imidazolyl, isothiazolyl, isoxazolyl, oxadiazolyl, oxazolyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl.

In one embodiment, a heterocyclyl is a spirocycle ("spiro") bicyclic moiety wherein two rings are connected through one atom, and either or both of the rings comprise at least one heteroatom. In one embodiment, a spiro bicyclic heterocycle comprises a 4-7 membered heterocyclic ring comprising 1-4 heteroatoms selected from oxygen, sulfur and nitrogen connected through a single atom to either a 3-6 membered ring comprising 1-2 heteroatoms selected from oxygen, sulfur and nitrogen or a 3-6 membered carbocyclic ring.

Exemplary spiro heterocycles of this type include, but are not limited to:

 

(2-azaspiro[3.3]heptane)     (2-oxa-6-azaspiro[3.3]heptane)

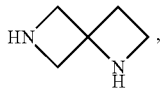 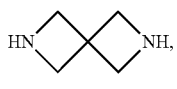

(1,6-diazaspiro[3.3]heptane)     (2,6-diazaspiro[3.3]heptane)

-continued

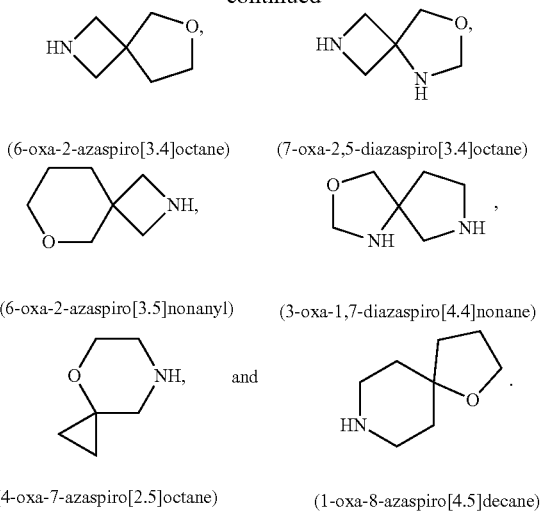

(6-oxa-2-azaspiro[3.4]octane)  (7-oxa-2,5-diazaspiro[3.4]octane)

(6-oxa-2-azaspiro[3.5]nonanyl)  (3-oxa-1,7-diazaspiro[4.4]nonane)

(4-oxa-7-azaspiro[2.5]octane)  (1-oxa-8-azaspiro[4.5]decane)

Such spiro bicyclic moieties may be attached to the rest of the molecule via a carbon atom or a nitrogen atom on either ring.

In one embodiment, a heterocycle is a bridged bicyclic moiety selected from the group consisting of:

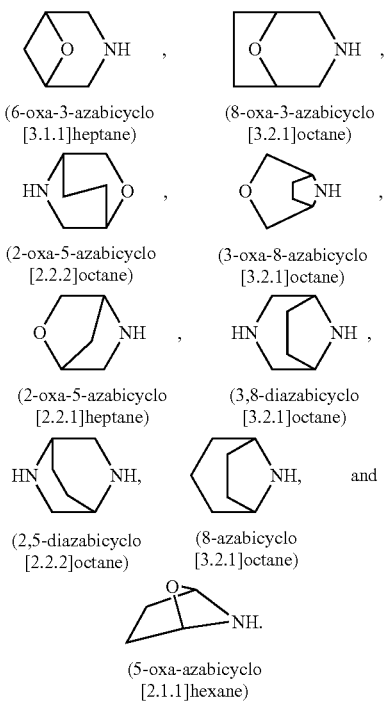

(6-oxa-3-azabicyclo [3.1.1]heptane)  (8-oxa-3-azabicyclo [3.2.1]octane)

(2-oxa-5-azabicyclo [2.2.2]octane)  (3-oxa-8-azabicyclo [3.2.1]octane)

(2-oxa-5-azabicyclo [2.2.1]heptane)  (3,8-diazabicyclo [3.2.1]octane)

(2,5-diazabicyclo [2.2.2]octane)  (8-azabicyclo [3.2.1]octane)

(5-oxa-azabicyclo [2.1.1]hexane)

Such bridged bicyclic moieties may be attached to the rest of the molecule via a carbon atom or a nitrogen atom on either ring.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound of formula (I), including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

Optical Isomers—Diastereomers—Geometric Isomers Tautomers

Included herein are various isomers of the compounds of formula (I). The term "isomers" refers to compounds that have the same composition and molecular weight but differ in physical and/or chemical properties. The structural difference may be in constitution (geometric isomers) or in the ability to rotate the plane of polarized light (stereoisomers). With regard to stereoisomers, a compound of formula (I) may have one or more asymmetric carbon atom and may occur as a racemic mixture or as individual enantiomers or diastereomers. All such isomeric forms are included herein, including mixtures thereof. If a compound of formula (I) contains a double bond, the substituent may be in the E or Z configuration. If a compound of formula (I) contains a disubstituted cycloalkyl, the cycloalkyl substituent may have a cis- or trans-configuration. All tautomeric forms are also intended to be included.

Any asymmetric atom (e.g., carbon) of a compound of formula (I) can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound of formula (I) can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —CH$_2$C(O)— groups (keto forms) may undergo tautomerism to form hydroxyl CH=C(OH)— groups (enol forms). Both keto and enol forms, individually as well as mixtures thereof, are included within the scope of the present invention.

Isotopic Variations

Compounds of formula (I) include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2$H (i.e., Deuterium or "D"), $^3$H, $^{11}$C, $^{13}$C, $^{14}$C, $^{13}$N, $^{15}$N, $^{15}$O, $^{17}$O, $^{18}$O, $^{32}$P, $^{35}$S, $^{18}$F, $^{123}$I, $^{125}$I and $^{36}$Cl. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}$C, $^{18}$F, $^{15}$O and $^{13}$N, may be particularly desirable for PET or SPECT studies.

Isotopically-labeled compounds of formula (I) can generally be prepared by conventional techniques known to those skilled in the art. Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of formula (I) is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

The compounds disclosed herein are inhibitors of a mutant IDH enzyme. These compounds are potentially useful in treating diseases or disorders associated with such enzymes including, but not limited to, cell proliferation disorders, such as cancer.

Examples of these mutant IDH enzymes are mutant IDH1 and mutant IDH2. A mutation in human IDH1 enzyme includes a mutation at amino acid residue 97, 100, or 132, e.g. G97D, R100Q, R132H, R132C, R132S, R132G, R132L, or R132V. A mutation in human IDH2 enzyme includes a mutation at amino acid residue 140 or 172, e.g. R140Q, R140G, R172K, R172M, R172S, R172G, or R172W.

Cell-proliferation disorders that may be associated with a mutant IDH enzyme activity include, but are not limited to, cancer. Examples of such cancers include, but are not limited to, Acute Lymphoblastic Leukemia; Acute Myeloid Leukemia; Adrenocortical Carcinoma; AIDS-Related Lymphoma; AIDS-Related Malignancies; Anal Cancer; Astrocytoma; Bile Duct Cancer; Bladder Cancer; Bone Cancer, Osteosarcoma/Malignant Fibrous Histiocytoma; Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Carcinoid Tumor; Carcinoid Tumor, Gastrointestinal; Carcinoma, Adrenocortical; Carcinoma, Islet Cell; Central Nervous System Lymphoma, Primary; Cerebral Astrocytoma/Malignant Glioma; Cervical Cancer; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma; Epithelial Cancer, Ovarian; Esophageal Cancer; Esophageal Cancer; Ewing's Family of Tumors; Extracranial Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer; Hodgkin's Lymphoma; Hypopharyngeal Cancer; Hypothalamic and Visual Pathway Glioma; Intraocular Melanoma; Islet Cell Carcinoma (Endocrine Pancreas); Kaposi's Sarcoma; Kidney Cancer; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia; Lymphoma, AIDS-Related; Lymphoma, Central Nervous System (Primary); Lymphoma, Cutaneous T-Cell; Lymphoma, Hodgkin's; Lymphoma, Hodgkin's During Pregnancy; Lymphoma, Non-Hodgkin's; Lymphoma, Primary Central Nervous System; Macroglobulinemia, Waldenstrom's; Male Breast Cancer; Malignant Mesothelioma; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Small Cell Lung Cancer; Oral Cancer; Oral Cavity and Lip Cancer; Oropharyngeal Cancer; steosarcoma/Malignant Fibrous Histiocytoma of Bone; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Prostate Cancer; Rectal Cancer; Renal Cell (Kidney) Cancer; Renal Pelvis and Ureter, Transitional Cell Cancer; Retinoblastoma; Rhabdomyosarcoma; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Soft Tissue; Sezary Syndrome; Skin Cancer; Skin Cancer (Melanoma); Skin Carcinoma, Merkel Cell; Small Cell Lung Cancer; Small Intestine Cancer; Soft Tissue Sarcoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Thymoma, Malignant; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Sarcoma; Vaginal Cancer; Visual Pathway and Hypothalamic Glioma; Vulvar Cancer; Waldenstrom's Macro globulinemia; and Wilms' Tumor.

In one embodiment, a cancer potentially associated with mutant IDH enzyme activity is brain cancer, such as an astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. In another embodiment, the brain cancer is glioma, glioblastoma multiforme, paraganglioma, or suprantentorial primordial neuroectodermal tumors (sPNET).

In another embodiment, a cancer potentially associated with mutant IDH enzyme activity is leukemia, such as acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blastphase chronic myelogenous leukemia, angioimmunoblastic lymphoma and acute lymphoblastic leukemia.

In one embodiment, a cancer potentially associated with mutant IDH enzyme activity is skin cancer, including melanoma. In another embodiment, a cancer potentially associated with mutant IDH enzyme activity is prostate cancer, breast cancer, thyroid cancer, colon cancer, or lung cancer. In another embodiment, a cancer potentially associated with mutant IDH enzyme activity is sarcoma, including central chondrosarcoma, central and periosteal chondroma, and fibrosarcoma. In another embodiment, a cancer potentially associated with mutant IDH enzyme activity is cholangiocarcinoma.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder described herein that may be associated with mutant IDH enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit mutant IDH enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDH mutation by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of formula (I).

One embodiment of the present invention provides for a method of treating a disease or disorder associated with mutant IDH enzyme activity comprising administration of an effective amount of a compound of formula (I) to a subject in need of treatment thereof. In one embodiment, the disease or disorder associated with a mutant IDH enzyme is a cell proliferation disorder.

In one embodiment, the cell proliferation disorder is cancer. In another embodiment, the cancer is a cancer associated with mutant IDH1 enzyme activity. In another embodiment, the cancer is associated with human mutant IDH1 enzyme activity, having a mutation at amino acid residue 97, 100, or 132, such as G97D, R100Q, R132H, R132C, R132S, R132G, R132L, or R132V.

In one embodiment, the cancer is associated with human mutant IDH2 enzyme activity having a mutation at amino acid residue 140 or 172, e.g. R140Q, R140G, R172K, R172M, R172S, R172G, or R172W.

In one embodiment, the cancer is brain cancer, leukemia, skin cancer, prostate cancer, thyroid cancer, colon cancer, lung cancer or sarcoma. In another embodiment the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In one embodiment, disclosed herein is the use of a compound of formula (I) in a therapy. The compound may be useful in a method of inhibiting mutant IDH enzyme activity in a subject, such as a mammal in need of such inhibition, comprising administering an effective amount of the compound to the subject.

In one embodiment, disclosed herein is a pharmaceutical composition comprising at least one compound of formula (I), or a pharmaceutically acceptable salt thereof, for use in potential treatment of a disorder or disease related to mutant IDH1 enzyme activity.

In one embodiment, disclosed herein is the use of a compound of formula (I) in the manufacture of a medicament for the treatment of a disease or disorder associated with mutant IDH enzyme activity. In one embodiment, the disease or disorder associated with a mutant IDH is a cell proliferation disorder. In another embodiment, the cell proliferation disorder is cancer. In another embodiment, the cancer is brain cancer, leukemia, skin cancer, breast, prostate cancer, thyroid cancer, colon cancer, lung cancer or sarcoma. In another embodiment, the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and/or cholangiocarcinoma.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of formula (I), or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound of formula (I), or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of formula (I). When prepared in unit dosage form, the composition of the invention typically contains from about 0.1 mg to 2 grams, or more specifically, 0.1 mg to 500 mg, or even more specifically, 0.2 mg to 100 mg, of a compound of formula (I), or a pharmaceutically acceptable salt thereof.

The compounds disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmellose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of formula (I) and one or more other active agent(s) together in the same pharmaceutical composition, or a compound of formula (I) and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound of formula (I) and at least one other therapeutic agent as a combined preparation for simultaneous, separate or sequential use in therapy. In one embodiment, the therapy is the treatment of a disease or disorder associated with mutant IDH enzyme activity.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

A kit of the invention may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound of formula (I) for treating a disease or disorder associated with mutant IDH enzyme activity, wherein the medicament is prepared for administration with another active agent. The invention also provides the use of another active agent for treating a disease or disorder associated with a mutant IDH enzyme, wherein the medicament is administered with a compound of formula (I).

The invention also provides the use of a compound of formula (I) for treating a disease or disorder associated with mutant IDH enzyme activity, wherein the patient has previously (e.g. within 24 hours) been treated with another active agent. The invention also provides the use of another therapeutic agent for treating a disease or disorder associated with mutant IDH enzyme activity, wherein the patient has previously (e.g. within 24 hours) been treated with a compound of formula (I). The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/ Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—(R)-1-(4-(4-Fluoro-2-methyl-1H-indol-5-yloxy)-5-methylpyrrolo[2,1-f] [1,2,4]triazin-6-yloxy)propan-2-yl)2-aminopropanoate, also known as BMS-582664), motesanib (N-(2,3-dihydro-3,3-dimethyl-1H-indoi-6-y!)-2-[(4-pyridinyimethyl)amino]-3-pyfidinecarboxamide, and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, and sold under the tradename Thioplex®.

Examples of anti-tumor antibiotics include, but are not limited to, doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), and mitomycin C (sold under the tradename Mutamycin®).

Examples of anti-metabolites include, but are not limited to, claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodium (MTX), sold under the tradenames Rheumatrex® and Trexall™), and pentostatin (sold under the tradename Nipent®).

Examples of retinoids include, but are not limited to, alitretinoin (sold under the tradename Panretin®), tretinoin (all-trans retinoic acid, also known as ATRA, sold under the tradename Vesanoid®), Isotretinoin (13-c/s-retinoic acid, sold under the tradenames Accutane®, Amnesteem®, Claravis®, Clarus®, Decutan®, Isotane®, Izotech®, Oratane®, Isotret®, and Sotret®), and bexarotene (sold under the tradename Targretin®).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename Trisenox®), asparaginase (also known as L-asparaginase, and Erwinia L-asparaginase, sold under the tradenames Elspar® and Kidrolase®).

EXPERIMENTAL

The following examples are intended to be illustrative only and not limiting in any way. Abbreviations used are those conventional in the art or the following.
ACN acetonitrile
BSA bovine serum albumin
° C. degree Celsius
DCE 1,2-dichloroethene
DCM dichloromethane
DMF NN-dimethylformamide
DMAP 4-dimethylaminopyridine
DMSO dimethylsulfoxide
DTT dithiothreitol
EtOAc ethyl acetate
EtOH ethanol
g gram
h hour(s)
HMDS hexamethyldisilazane
HPLC high pressure liquid chromatography
kg kilogram
L liter
LC liquid chromatography
LCMS liquid chromatography and mass spectrometry
MeOH methanol
MS mass spectrometry
MTBE methyl tert-butyl ether
min minutes
mL milliliter(s)
m/z mass to charge ratio
nm nanometer
nM nanomolar
N normal
NMR nuclear magnetic resonance
PS-PPh$_3$ polymer supported-triphenylphosphine
RT room temperature
sat. saturated
TEA triethylamine
TFA trifluoroacetic acid
THF tetrahydrofuran General Synthetic Schemes The compounds of formula (I) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

The compounds described herein may be made from commercially available starting materials or synthesized using known organic, inorganic, and/or enzymatic processes.

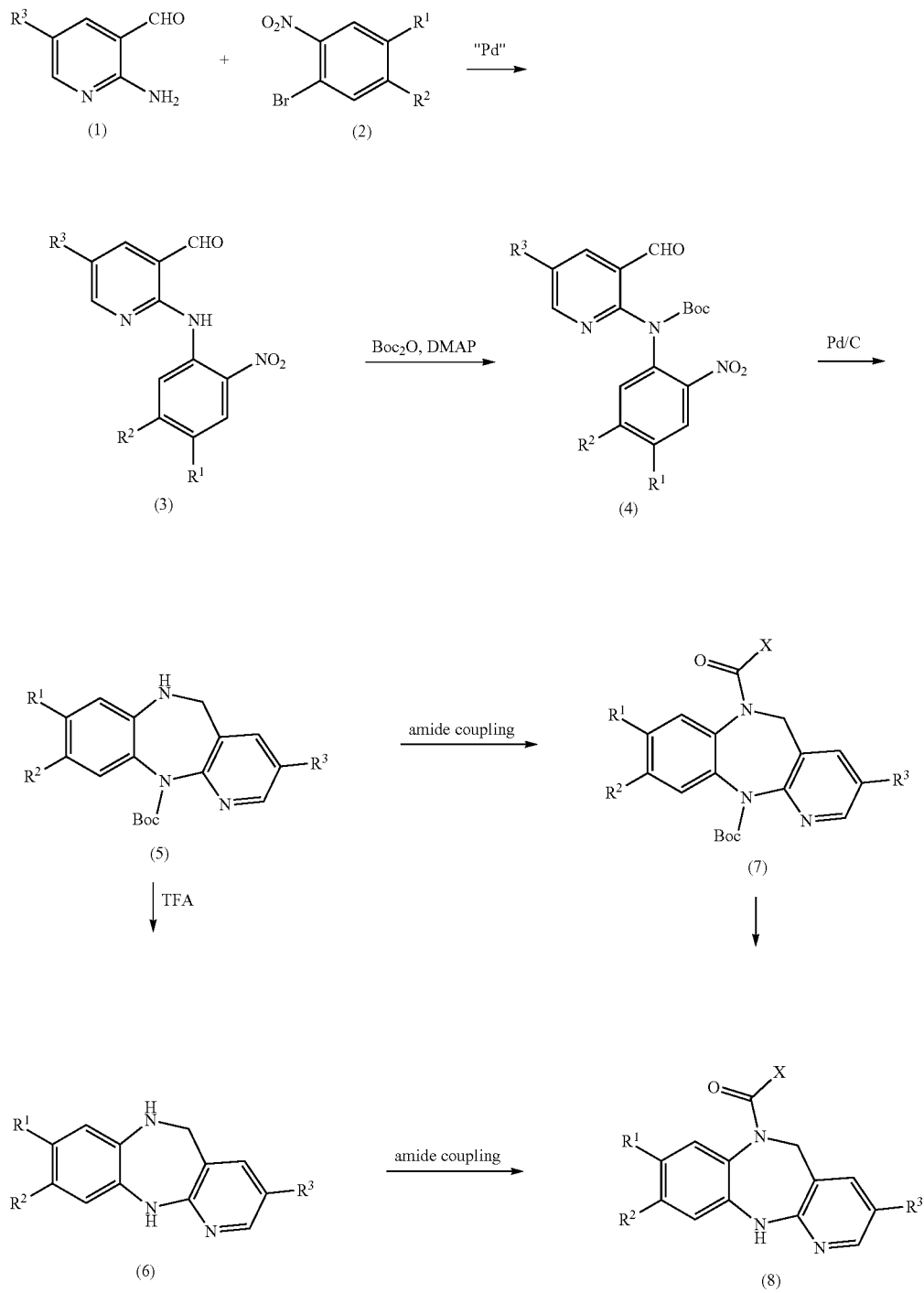

Scheme 1

In general scheme 1, compounds of formula (8) can be formed in multiple ways. Substituted aminopyridine (1) and a nitro bromobenzene (2) can be combined in a palladium-mediated C—N coupling reaction to afford (3). Formation of a carbamate followed by reduction of the nitro group with palladium on carbon affords the substituted tricyclic compound (5). Deprotection followed by amide coupling affords the desired tricycle (8). Alternatively, a direct amide coupling can lead to the bis-Boc-protected tricyclic compound (7). Deprotection of the Boc groups affords the tricyclic compound (8).

Scheme 2

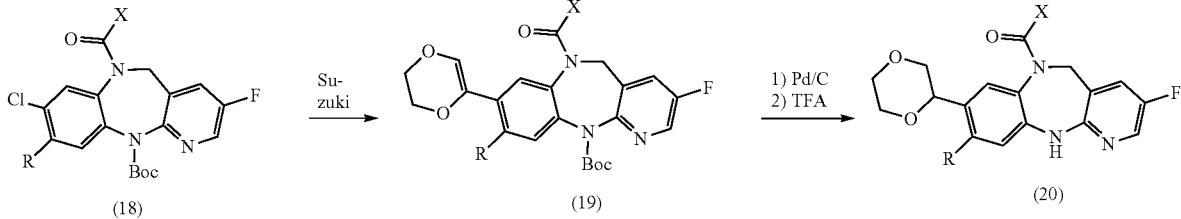

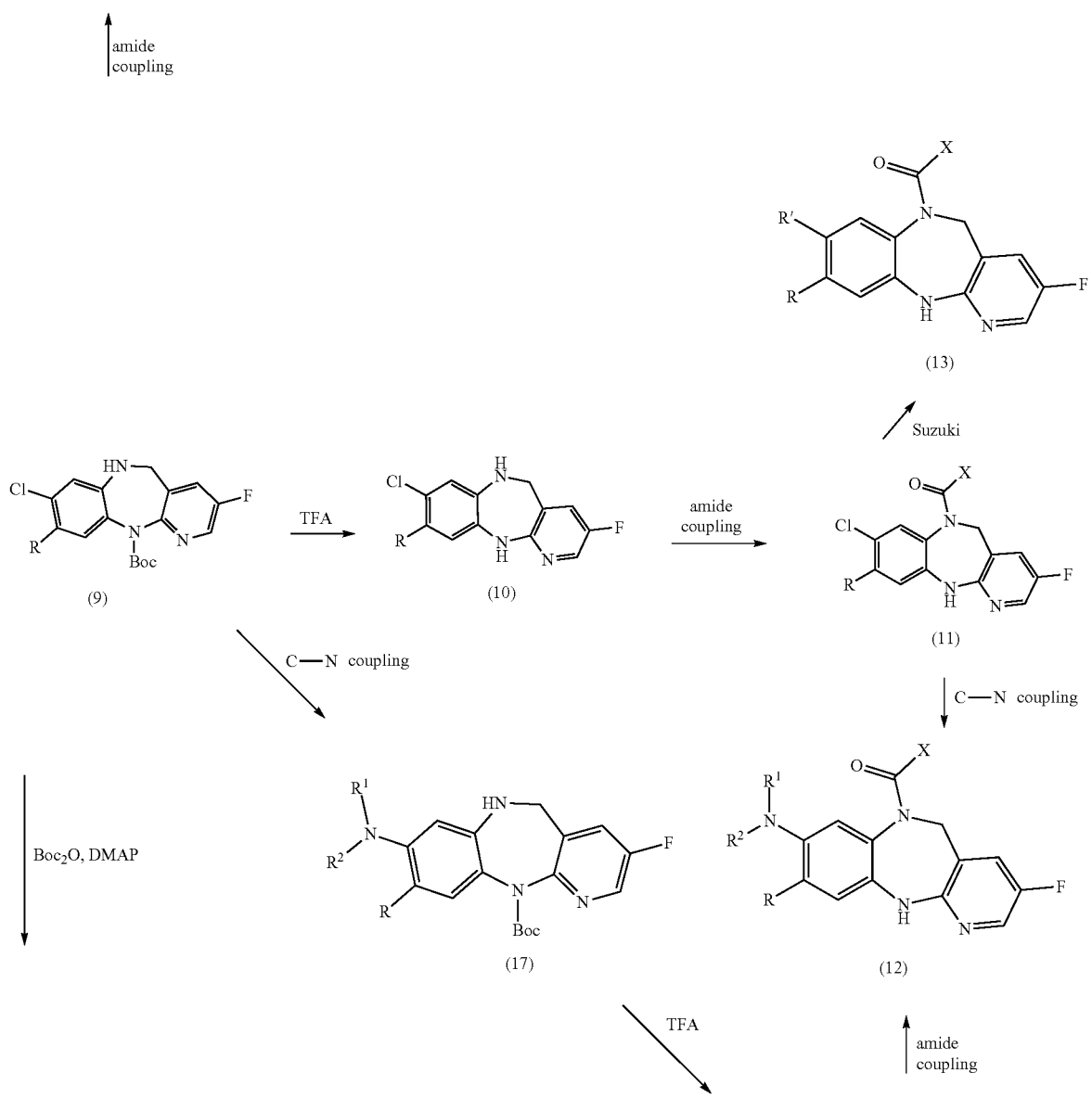

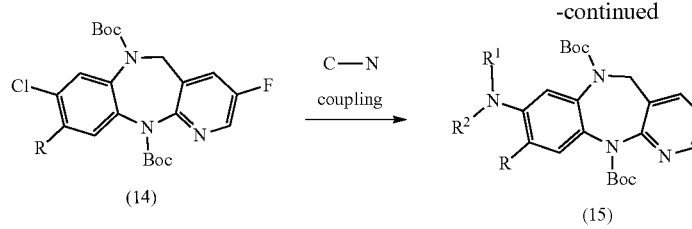
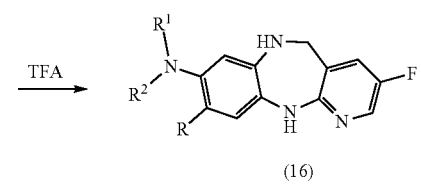

In general scheme 2, compound (9) can be used in a multitude of reactions. TFA deprotection followed by amide coupling affords tricycle (11), which can be further derivatized either through C—N coupling reaction with appropriate amines affording product (12) or via Suzuki reaction affording product (13). Alternatively, compound (9) can be protected to afford the bis-Boc protected tricycle (14). C—N coupling reaction between (14) and appropriate amines affords (15). TFA deprotection of (15) affords de-Boc tricycle (16). Alternatively, (16) can be obtained from (9) via a C—N coupling/TFA reaction sequence. Amide coupling of (16) affords compounds of formula (12). Alternatively, amide coupling of compound (9) affords compound (18). Suzuki cross-coupling between (18) and boronate ester affords (19), which undergoes Pd-catalyzed hydrogenation and TFA deprotection to afford compounds of formula (20).

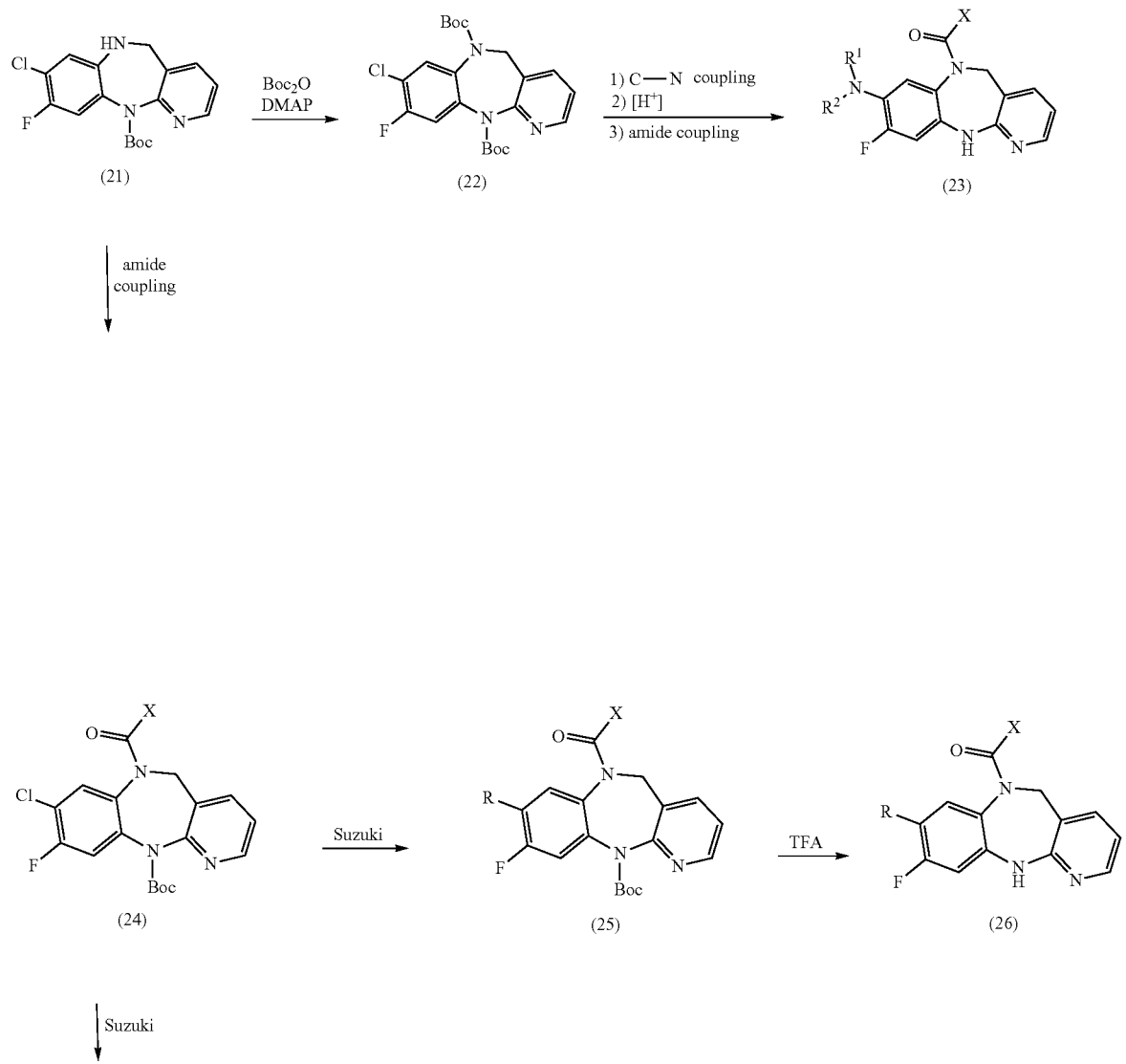

33

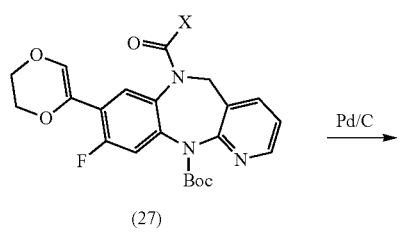
(27)

-continued

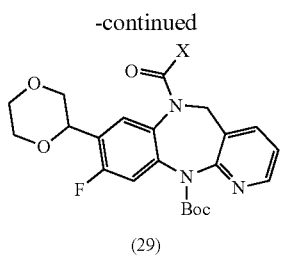
(29)

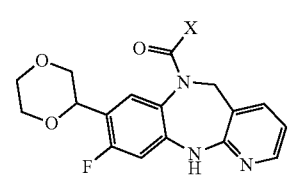
(30)

34

+

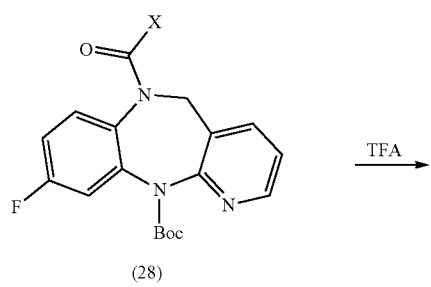
(28)

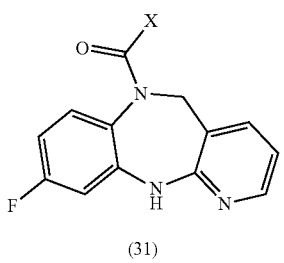
(31)

In general scheme 3, compound (21) can be used in a multitude of reactions. Boc-protection affords (22). A three-step reaction sequence involving C—N coupling/deprotection/amide coupling affords the final product (23). Alternatively, amide coupling of (21) with appropriate amines affords (24). Compound (24) can be used in a multitude of reactions. Compounds of formula (26) can be prepared from (24) through Suzuki coupling reaction with appropriate boronate ester followed by Boc-deprotection with TFA. Alternatively, Suzuki coupling between (24) and boronate ester affords C—C coupling product (27) and de-halogenated product (28). Pd-catalyzed hydrogenation of (27) affords compound (29). Boc-deprotection of (29) affords the final product (30). Likewise, Boc-deprotection of (28) affords the product (31).

-continued

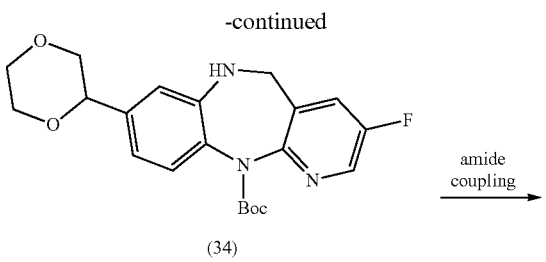
(34)

amide coupling

Scheme 4

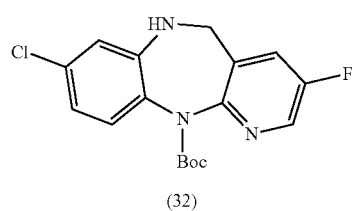
(32)

Suzuki

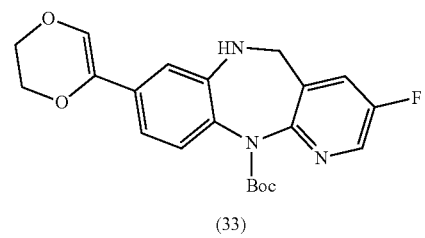
(33)

Pd/C

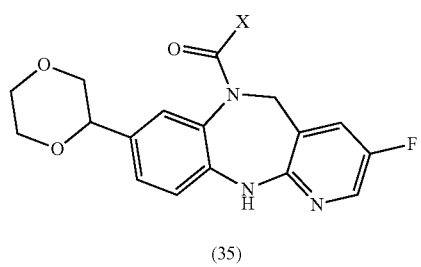
(35)

In general scheme 4, compounds of formula (35) can be prepared via a three-step sequence starting with aryl chloride (32). Suzuki coupling between (32) and boronate ester affords (33). Pd-catalyzed hydrogenation of alkene (33) affords (34). Amide coupling between (34) with an appropriate amine affords compounds of formula (35).

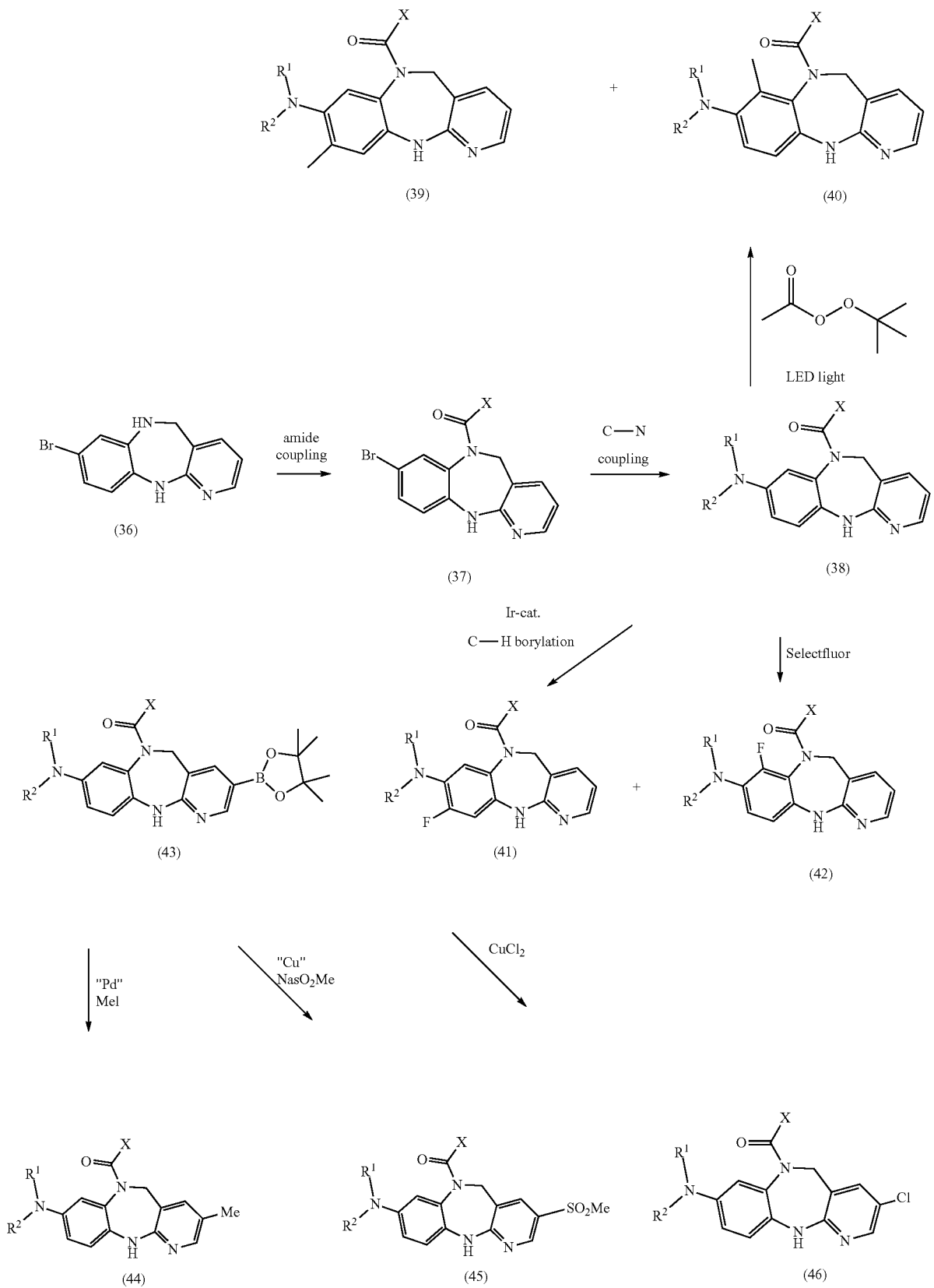

In general scheme 5, compounds of formula (38) can be prepared in two steps from (36) through an amide coupling and C—N coupling. Compound (38) can be used in a multitude of reactions. Radical reaction of (38) with t-butyl peroxyacetate under LED light affords (39) and (40). Electrophilic fluorination of (38) with selectfluor affords (41) and (42). Iridium-catalyzed regioselective C—H borylation of (38) affords boronate ester (43). Pd-catalyzed alkylation of (43) with iodomethane affords the product (44). Copper-mediated sulfonylation of (43) affords compounds of formula (45). Copper(II) chloride reacts with boronate ester (43) affording compounds of formula (46).

Scheme 6

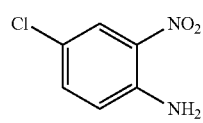
(47)

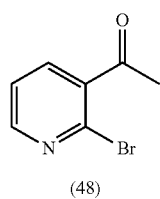
(48)

1) "Pd"
2) Boc₂O, DMAP

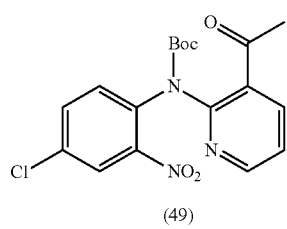
(49)

Pt/C

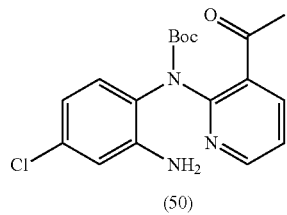
(50)

reductive amination

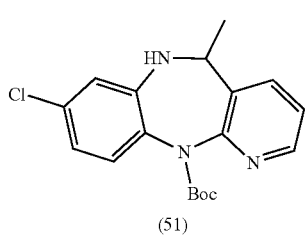
(51)

1) amide coupling
2) TFA

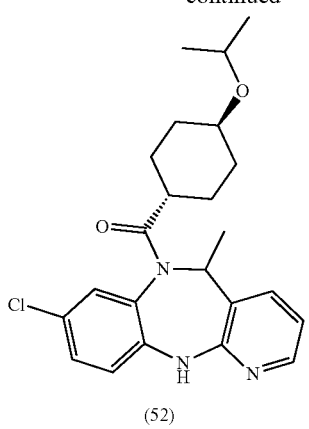
(52)

C—N coupling

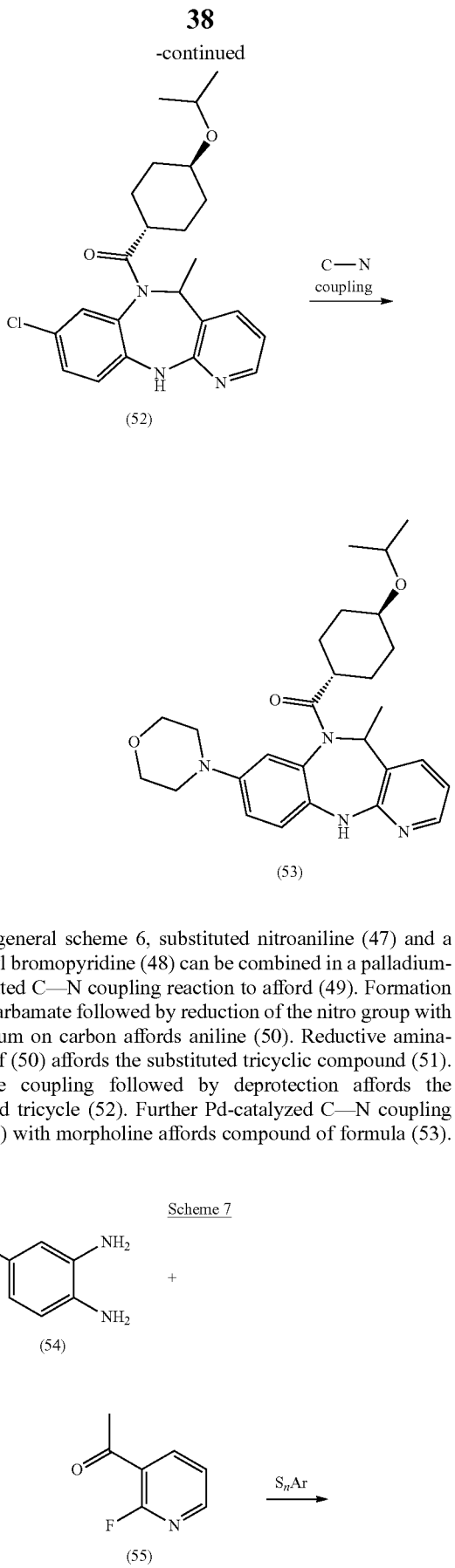
(53)

In general scheme 6, substituted nitroaniline (47) and a formyl bromopyridine (48) can be combined in a palladium-mediated C—N coupling reaction to afford (49). Formation of a carbamate followed by reduction of the nitro group with platinum on carbon affords aniline (50). Reductive amination of (50) affords the substituted tricyclic compound (51). Amide coupling followed by deprotection affords the desired tricycle (52). Further Pd-catalyzed C—N coupling of (52) with morpholine affords compound of formula (53).

Scheme 7

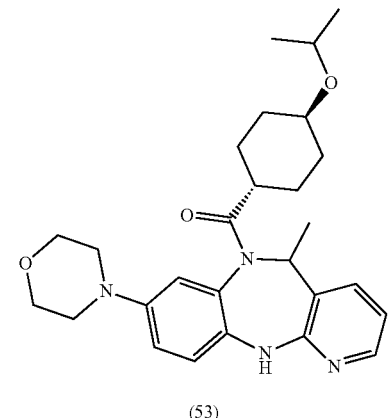
(54)

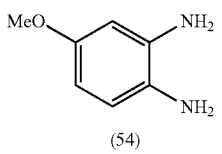
(55)

S$_n$Ar

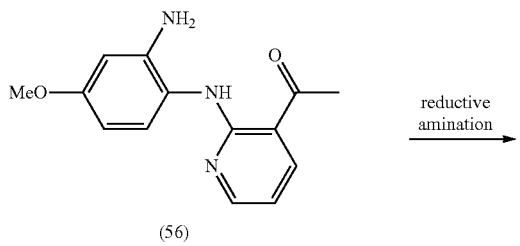

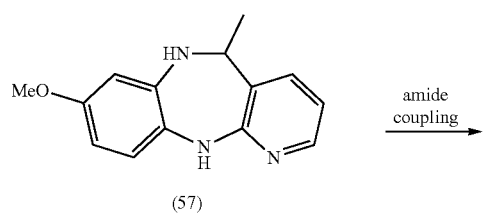

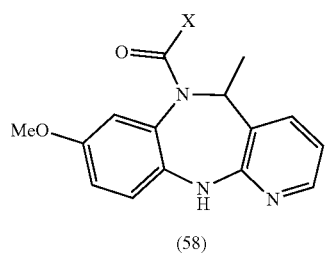

In general scheme 7, S$_N$Ar reaction between dianiline (54) and formyl fluoropyridine (55) affords (56). Reductive amination of (56) affords the substituted tricyclic compound (57). Amide coupling affords the desired tricycle (58).

Scheme 8

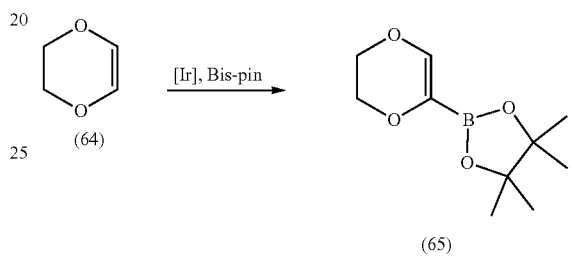

In general scheme 8, ketone (59) reacts with TMS-protected isopropanol to give (60). Saponification of ester (60) with lithium hydroxide affords compound of formula (61). Protection with benzylbromide followed by chiral separation affords (62). Hydrogenation of (62) affords compound of formula (63).

Scheme 9

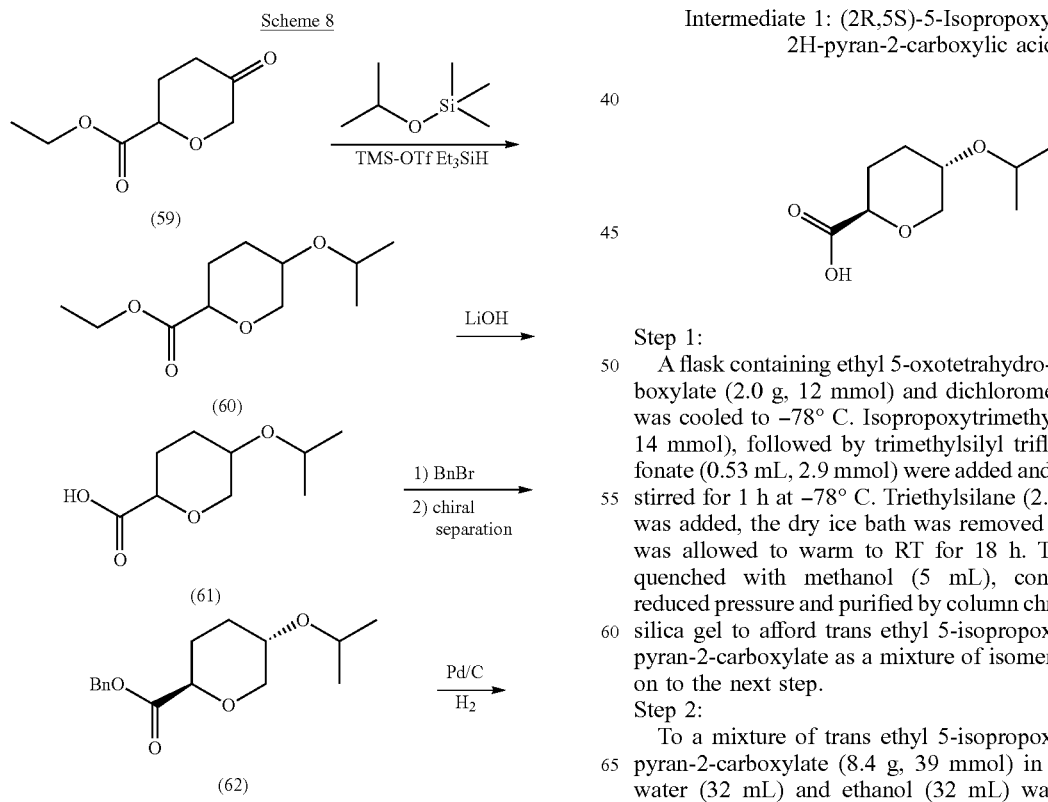

In general scheme 9, Iridium-catalyzed conversion of 1,4-dioxene (64) with bis(pinacolato)diboron affords the vinyl boronate ester (65).

INTERMEDIATES

Intermediate 1: (2R,5S)-5-Isopropoxytetrahydro-2H-pyran-2-carboxylic acid

Step 1:
A flask containing ethyl 5-oxotetrahydro-2H-pyran-2-carboxylate (2.0 g, 12 mmol) and dichloromethane (100 mL) was cooled to −78° C. Isopropoxytrimethylsilane (2.5 mL, 14 mmol), followed by trimethylsilyl trifluoromethanesulfonate (0.53 mL, 2.9 mmol) were added and the mixture was stirred for 1 h at −78° C. Triethylsilane (2.0 mL, 13 mmol) was added, the dry ice bath was removed and the reaction was allowed to warm to RT for 18 h. The mixture was quenched with methanol (5 mL), concentrated under reduced pressure and purified by column chromatography on silica gel to afford trans ethyl 5-isopropoxytetrahydro-2H-pyran-2-carboxylate as a mixture of isomers that was taken on to the next step.

Step 2:
To a mixture of trans ethyl 5-isopropoxytetrahydro-2H-pyran-2-carboxylate (8.4 g, 39 mmol) in THF (100 mL), water (32 mL) and ethanol (32 mL) was added lithium hydroxide (3.5 g, 0.15 mol) and the mixture was stirred at RT for 18 h. HCl (2.0 M in water, 78 mL, 0.16 mmol) was added and then the mixture was extracted with ethyl acetate (2×150 mL). The organic extracts were combined, dried over sodium sulfate, filtered and concentrated to afford trans 5-isopropoxytetrahydro-2H-pyran-2-carboxylic acid that was taken on to the next step without further purification.

Step 3:

To a mixture of trans 5-isopropoxytetrahydro-2H-pyran-2-carboxylic acid (10.3 g, 54.5 mmol), potassium carbonate (15.1 g, 109 mmol) and sodium iodide (1.6 g, 11 mmol) in DMF (160 mL) was added benzyl bromide (7.1 mL, 60 mmol). The mixture was stirred for 16 h. The reaction mixture was diluted with ethyl acetate (500 mL) and washed with water (6×100 mL) and brine (1×50 mL). The organic layer was dried over sodium sulfate, filtered, and concentrated under reduced pressure to afford the crude product. The residue was purified by column chromatography on silica gel to afford trans benzyl 5-isopropoxytetrahydro-2H-pyran-2-carboxylate. The purified product was then further purified by chiral SFC (IC, 2.1×25 cm, methanol with 0.25% DMEA and 10% modifier in $CO_2$) to separate the enantiomers.

Characterization data for the first peak isolated from SFC: MS: 279 (M+1).

Characterization data for the second peak isolated from SFC: MS: 279 (M+1).

Step 4:

To a mixture of trans benzyl 5-isopropoxytetrahydro-2H-pyran-2-carboxylate (peak 2 from SFC, 3.4 g, 12 mmol) in ethyl acetate (120 mL) was added palladium on carbon (10% by weight, 2.60 g, 2.4 mmol) under an atmosphere of argon. The flask was fitted with a hydrogen balloon and the mixture was evacuated and purged 5 times with hydrogen. The mixture was stirred overnight at RT, then filtered through celite and the celite was washed with ethyl acetate. The filtrate was concentrated under reduced pressure to afford trans 5-isopropoxytetrahydro-2H-pyran-2-carboxylic acid as a single enantiomer (2R,5S)-5-isopropoxytetrahydro-2H-pyran-2-carboxylic acid. $^1$H NMR (500 MHz, DMSO-$d_6$) δ 12.61 (s, 1H), 3.89 (ddd, 1H), 3.82 (dd, 1H), 3.68 (hept, 1H), 3.39-3.31 (m, 1H), 3.05 (dd, 1H), 2.02-1.95 (m, 1H), 1.95-1.88 (m, 1H), 1.55-1.45 (m, 1H), 1.41-1.31 (m, 1H), 1.06 (d, 3H), 1.04 (d, 3H).

Trans benzyl 5-isopropoxytetrahydro-2H-pyran-2-carboxylate (peak 1 from SFC) can be hydrogenated as described in Step 4 to afford trans 5-isopropoxytetrahydro-2H-pyran-2-carboxylic acid as a single enantiomer.

Intermediate 2: 2-(5,6-Dihydro-1,4-dioxin-2-yl)-4,4,5,5-tetramethyl-1,3,2-dioxaborolane

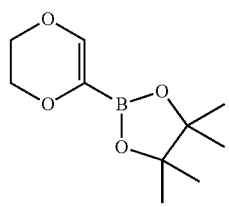

To a 40 mL vial was added 4,4,4',4',5,5,5',5'-octamethyl-2,2'-bi(1,3,2-dioxaborolane) (1.47 g, 5.81 mmol), 4,4'-di-tert-butyl-2,2'-bipyridine (47 mg, 0.174 mmol) and (1,5-cyclooctadiene)(methoxy)iridium(I) dimer (98 mg, 0.148 mmol) in a glovebox. The vial was sealed and degassed hexane (2.5 mL) and 2,3-dihydro-1,4-dioxine (926 µl, 11.62 mmol) were added subsequently. The reaction was stirred at RT overnight, filtered over celite and concentrated. The residue was purified by column chromatography (40 g silica, 0-60% EtOAc in hexane) to give 2-(5,6-dihydro-1,4-dioxin-2-yl)-4,4,5,5-tetramethyl-1,3,2-dioxaborolane as an oil. MS: 213 (M+1).

Intermediate 3: 8-Bromo-3-fluoro-6,11-dihydro-5H-benzo[b]pyrido[2,3-e][1,4]diazepine

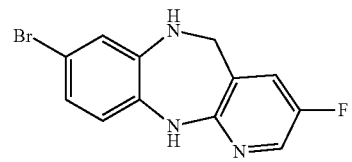 [SMILES: Fc1cnc2c(c1)CNc1cc(Br)ccc1N2]

Step 1:

Into a 20-L 4-necked round-bottom flask purged and maintained with an inert atmosphere of nitrogen was placed 2-chloro-5-fluoro-pyridine (750 g, 5.70 mol), xantphos (165 g, 285.16 mmol), $Cs_2CO_3$ (5600 g), Pd(OAc)$_2$ (120 g) and dioxane (8000 mL). This was followed by the addition of benzophenone imine (1139 g) dropwise with stirring. The resulting solution was stirred overnight at 50° C. The reaction was then quenched by the addition of water/ice. The resulting solution was extracted with 3×1000 mL of ethyl acetate and the organic layers were combined. The resulting mixture was washed with ×1000 mL of brine, dried over anhydrous sodium sulfate and concentrated under vacuum to afford N-(diphenylmethylidene)-5-fluoropyridin-2-amine as a solid.

Step 2:

Into a 20-L 4-necked round-bottom flask was placed a solution of N-(diphenylmethylidene)-5-fluoropyridin-2-amine (1100 g, 3.98 mol) in dichloromethane (8000 mL). This was followed by the addition of trifluoroacetic acid (4500 g, 39.81 mol) dropwise with stirring. The resulting solution was stirred overnight at RT. The reaction was then quenched by the addition of water/ice. The resulting solution was extracted with 2×2000 mL of ethyl acetate and the aqueous layers combined and the organic layers combined. The pH value of the solution was adjusted to 9-10 with sodium carbonate. The resulting solution was extracted with 3×2000 mL of ethyl acetate and the organic layers were combined. The resulting mixture was washed with brine, dried over anhydrous sodium sulfate and concentrated under vacuum to afford 5-fluoropyridin-2-amine as a solid.

Step 3:

Into a 5-L 4-necked round-bottom flask purged and maintained with an inert atmosphere of nitrogen, was placed 5-fluoropyridin-2-amine (230 g, 2.05 mol), TEA (415 g, 4.10 mol), and dichloromethane (3000 mL). This was followed by the addition of 2,2-dimethylpropanoyl chloride (271 g, 2.25 mol, 1.10 equiv) dropwise with stirring. The resulting solution was stirred for 5 h at RT. The resulting mixture was washed with water and brine, dried over anhydrous sodium sulfate and concentrated under vacuum to afford N-(5-fluoropyridin-2-yl)-2,2-dimethylpropanamide as a solid.

Step 4:

Into a 10-L 4-necked round-bottom flask purged and maintained with an inert atmosphere of nitrogen, was placed N-(5-fluoropyridin-2-yl)-2,2-dimethylpropanamide (332 g, 1.69 mol) and ether (6000 mL). This was followed by the addition of t-BuLi (3257 mL, 2.50 equiv) dropwise with stirring at −78° C. The mixture was stirred for 1 h at −78° C. To this was added N,N-dimethylformamide (1236 g, 16.91 mol) dropwise with stirring. The resulting solution was stirred for 2 h at −60° C. The reaction was then quenched by the addition of water. The resulting solution was extracted with 3×2000 mL of ethyl acetate and the organic layers were combined. The resulting mixture was washed with brine, dried over anhydrous sodium sulfate and concentrated under vacuum. The resulting mixture was washed with petroleum ether to afford N-(5-fluoro-3-formylpyridin-2-yl)-2,2-dimethylpropanamide as a solid.

Step 5:

Into a 5-L 4-necked round-bottom flask, was placed N-(5-fluoro-3-formylpyridin-2-yl)-2,2-dimethylpropanamide (300 g, 1.34 mol) and hydrogen chloride (2N) (3500 mL). The resulting solution was stirred for 2 h at 100° C. and then cooled to RT. The pH value of the solution was adjusted to 8-9 with sodium bicarbonate. The solids were collected by filtration to afford 2-amino-5-fluoropyridine-3-carbaldehyde as a solid.

Step 6:

Into a 3-L 3-necked round-bottom flask purged and maintained with an inert atmosphere of nitrogen, was placed 2-amino-5-fluoropyridine-3-carbaldehyde (130 g, 927.81 mmol), xantphos (53.7 g, 92.81 mmol), Pd$_2$(dba)$_3$/CHCl$_3$ (28.8 g) and 1,4-dibromo-2-nitrobenzene (285 g, 1.01 mol). This was followed by the addition of dioxane (1500 mL). The mixture was degassed by N$_2$. To this was added Cs$_2$CO$_3$ (455 g). The resulting solution was stirred for 3 h at 100° C. The reaction mixture was cooled and then quenched by the addition of water/ice. The solids were collected by filtration, washed with EtOH and DCM:petroleum ether (1:3) to afford 2-R4-bromo-2-nitrophenyl)aminol-5-fluoropyridine-3-carbaldehyde as a solid.

Step 7:

Into a 10-L 4-necked round-bottom flask purged and maintained with an inert atmosphere of nitrogen, was placed 2-R4-bromo-2-nitrophenyl)aminol-5-fluoropyridine-3-carbaldehyde (280 g, 823.28 mmol), tetrahydrofuran (3000 mL), water (3000 mL), sodium carbonate (219 g, 2.07 mol) and Na$_2$S$_2$O$_4$ (326 g). The resulting solution was stirred for 5 h at RT and the reaction mixture was cooled. The organic was collected and diluted with brine. The solids were collected by filtration to afford 2-[(2-amino-4-bromophenyl)aminol-5-fluoropyridine-3-carbaldehyde as a solid.

Step 8:

Into a 2000-mL 4-necked round-bottom flask purged and maintained with an inert atmosphere of nitrogen, was placed a solution of 2-[(2-amino-4-bromophenyl)aminol-5-fluoropyridine-3-carbaldehyde (150 g, 483.68 mmol) in tetrahydrofuran (2000 mL), trifluoroacetic acid (337 g, 2.98 mol) and TES (338 g). The resulting solution was stirred overnight at 80° C. The reaction mixture was cooled to RT and then concentrated under vacuum. The resulting mixture was washed with DCM and the resulting solution was diluted with DCM and H$_2$O. The pH value of the solution was adjusted to 8-9 with sodium bicarbonate. The organic layer was collected and washed with brine. The mixture was dried over anhydrous sodium sulfate and concentrated under vacuum. The residue was washed with ether to afford 8-bromo-3-fluoro-6,11-dihydro-5H-benzo[b]pyrido[2,3-e][1,4]diazepine as a solid. MS: 294 (M+1). $^1$H NMR: (300 MHz, DMSO-d$_6$): δ 9.03 (1H, s), 7.98 (1H, d), 7.45 (1H, dd), 6.98 (1H, d), 6.91 (1H, d), 6.79 (1H, dd), 4.02 (2H, d)

Intermediate 4: Tert-butyl 8-chloro-3-fluoro-5,6-dihydro-11H-benzo[b]pyrido[2,3-e][1,4]diazepine-11-carboxylate

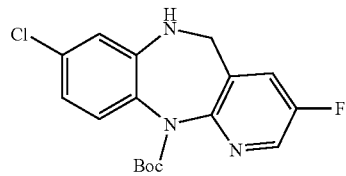

Step 1:

To a round bottle flask was added 2-amino-5-fluoronicotinaldehyde (0.97 g, 6.92 mmol), 1-bromo-4-chloro-2-nitrobenzene (1.80 g, 7.62 mmol), Pd$_2$(dba)$_3$ (0.32 g, 0.35 mmol), Xantphos (0.44 g, 0.76 mmol), Cs$_2$CO$_3$ (3.38 g, 10.38 mmol) and dioxane (20 mL). The reaction mixture was bubbled with nitrogen gas for 5 min and refluxed for 3 h. The reaction was cooled to RT, followed by addition of di-tert-butyl dicarbonate (1.96 g, 9.0 mmol) and DMAP (0.85 g, 6.92 mmol). The resulting mixture was stirred at RT for 1 h, diluted with DCM and filtered through a pad of celite, and washed with DCM. The filtrate was absorbed on silica gel and purified by column chromatography (120 g silica, 0-10% EtOAc in hexane) to afford tert-butyl (4-chloro-2-nitrophenyl)(5-fluoro-3-formylpyridin-2-yl)carbamate.

Step 2:

Under nitrogen gas flow, 3% Pt—0.6% V/C (280 mg, 0.197 mmol) was added to the solid of tert-butyl (4-chloro-2-nitrophenyl)(5-fluoro-3-formylpyridin-2-yl)carbamate (1.87 g, 4.72 mmol), followed by addition of MeOH (24 mL) and ethyl acetate (12 mL). The reaction mixture was vacuum/N$_2$ exchanged and then vacuum/H$_2$ exchanged three times each. The reaction mixture was stirred with H$_2$ balloon at RT for 16 h. After completion, the reaction mixture was diluted in DCM and filtered over celite, washed with DCM and EtOAc, and concentrated. The residue was purified by column chromatography (120 g, 0-30% EtOAc in hexane) to afford tert-butyl 8-chloro-3-fluoro-5,6-dihydro-11H-benzo[b]pyrido[2,3-e][1,4]diazepine-11-carboxylate. MS: 350 (M+1).

Intermediate 5: Tert-butyl-8-bromo-3-fluoro-5,6-dihydro-11H-benzo[b]pyrido[2,3-e][1,4]diazepine-11-carboxylate

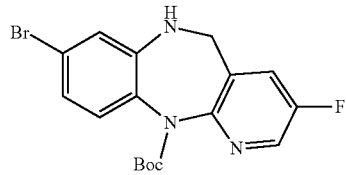 [SMILES: CC(C)(C)OC(=O)N1c2ccc(Cl)cc2NCc2cc(F)cnc21]

Step 1:

2-Amino-5-fluoronicotinaldehyde (4.0 g, 28 mmol), 1,4-dibromo-2-nitrobenzene (8.8 g, 31 mmol), Xantphos (1.8 g, 3.1 mmol), Pd$_2$(dba)$_3$ (1.3 g, 1.4 mmol) and Cs$_2$CO$_3$ (14 g, 43 mmol) were combined in dioxane (80 mL) and stirred at 100° C. for 2 h. The reaction mixture was then cooled to RT, and stabilized with a water bath. DMAP (0.35 g, 2.8 mmol) was added followed carefully and portionwise by di-tert-butyl dicarbonate (8.1 g, 37 mmol). The resulting mixture was stirred at RT for 2 h, then diluted with DCM, filtered through celite, then concentrated onto silica gel and purified by flash chromatography (0-80% EtOAc:hexane) to afford tert-butyl (2-amino-4-bromophenyl)(5-fluoro-3-formylpyridin-2-yl)carbamate. MS: 384 (M-$^t$Bu).

Step 2:

Tert-butyl (2-amino-4-bromophenyl)(5-fluoro-3-formylpyridin-2-yl)carbamate (0.70 g, 1.6 mmol) and platinum and vanadium (1%:2%) on Carbon (0.52 g, 0.064 mmol) were added to a round bottom flask and the flask was sealed and purged with $N_2$ gas. The mixture was then diluted with 2:1 MeOH:EtOAc (16 mL) and subjected to alternating vacuum and $H_2$ gas three times. The reaction mixture was then stirred at RT for 16 h under an atmosphere of $H_2$. The mixture was then subjected to alternating vacuum and $N_2$ gas three times. The reaction flask was purged with $N_2$, and the mixture was diluted with DCM. The mixture was carefully filtered through celite under a stream of argon, and the celite was flushed with DCM:MeOH. The filtrate was concentrated in vacuo and then purified by flash chromatography (0-80% EtOAc:Hexane) to afford tert-butyl 8-bromo-3-fluoro-5,6-dihydro-11H-benzo[b]pyrido[2,3-e][1,4]diazepine-11-carboxylate. MS: 338 (M-$^t$Bu).

Intermediate 6: Tert-butyl 8-chloro-3,9-difluoro-5,6-dihydro-11H-benzo[b]pyrido[2,3-e][1,4]diazepine-11-carboxylate

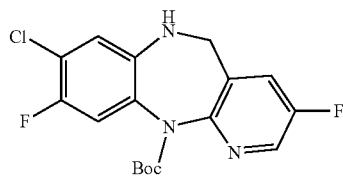 [SMILES: CC(C)(C)OC(=O)N1c2cc(F)c(Cl)cc2NCc2cc(F)cnc21]

Step 1:

A mixture of 2-amino-5-fluoronicotinaldehyde (500 mg, 3.57 mmol), 1-bromo-4-chloro-5-fluoro-2-nitrobenzene (999 mg, 3.93 mmol), $Pd_2(dba)_3$ (163 mg, 0.178 mmol), (9,9-dimethyl-9H-xanthene-4,5-diyl)bis(diphenylphosphine) (227 mg, 0.393 mmol) and cesium carbonate (1.74 g, 5.35 mmol) in dioxane (10 mL) was degassed with $N_2$/vacuum exchange three times. The mixture was refluxed for 4 h, cooled and diluted with DCM and filtered through a pad of celite, and washed with DCM three times. The solvent was concentrated to 20 mL and a solid was collected with filtration and washed with hexane/ethyl acetate (9/1) to afford 2-((4-chloro-5-fluoro-2-nitrophenyl)amino)-5-fluoronicotinaldehyde as a solid. MS: 314.2 (M+1).

Step 2:

Triethylamine (0.347 mL, 2.487 mmol) and DMAP (234 mg, 1.913 mmol) were added to a stirred mixture of $Boc_2O$ (2.87 mmol) and 2-((4-chloro-5-fluoro-2-nitrophenyl)amino)-5-fluoronicotinaldehyde (600 mg, 1.913 mmol) in $CH_2Cl_2$ (15 mL) and the mixture was stirred at RT for 1 h. The solvent was removed and the residue was purified with ISCO column (80 g silica gel eluting with 0-50% EtOAc/hexane gradient) to afford tert-butyl (4-chloro-5-fluoro-2-nitrophenyl)(5-fluoro-3-formylpyridin-2-yl)carbamate as a syrup. MS: 414 (M+1).

Step 3:

A mixture of tert-butyl (4-chloro-5-fluoro-2-nitrophenyl)(5-fluoro-3-formylpyridin-2-yl)carbamate (470 mg, 1.136 mmol) in MeOH (6 mL) and EtOAc (3 mL), and 3% Pt-0.6% V/C (47 mg, 0.182 mmol) were loaded into a flask fitted with a hydrogen gas balloon. The reaction mixture was $H_2$/vacuum exchanged three times, and stirred overnight at RT. The reaction mixture was diluted in DCM and filtered through a short pad of celite. The solvent was removed under reduced pressure and the residue was purified with ISCO column (40 g gold, EtOAc/hexane 0-100% then MeOH/DCM 0-10%) to afford tert-butyl 8-chloro-3,9-difluoro-5H-benzo[b]pyrido[2,3-e][1,4]diazepine-11(6H)-carboxylate as a solid. MS: 368 (M+1).

Intermediate 7: Tert-butyl 8-chloro-9-fluoro-6-(1-(2,2,2-trifluoroethyl)piperidine-4-carbonyl)-5,6-dihydro-11H-benzo[b]pyrido[2,3-e][1,4]diazepine-11-carboxylate

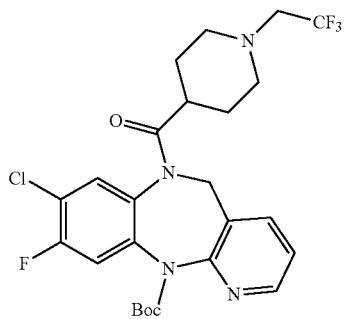 [SMILES: CC(C)(C)OC(=O)N1c2cc(F)c(Cl)cc2N(C(=O)C2CCN(CC(F)(F)F)CC2)Cc2cccnc21]

Step 1:

A mixture of 2-aminonicotinaldehyde (500 mg, 4.09 mmol), 1-bromo-4-chloro-5-fluoro-2-nitrobenzene (1.15 g, 4.50 mmol), $Pd_2(dba)_3$ (187 mg, 0.205 mmol), (9,9-dimethyl-9H-xanthene-4,5-diyl)bis(diphenylphosphine) (261 mg, 0.450 mmol), and cesium carbonate (2.0 g, 6.14 mmol) in dioxane (10 mL) was degassed with vacuum/nitrogen exchange three times. The mixture was heated to reflux for 4 h before cooled to RT. The reaction mixture was diluted with DCM and filtered through a pad of celite, washed three times with DCM. The solvent was concentrated to ~20 mL and a solid was collected with filtration and washed with hexane/ethyl acetate (9/1) to afford 2-((4-chloro-5-fluoro-2-nitrophenyl)amino)nicotinaldehyde as a solid. MS: 296 (M+1)

Step 2:

Triethylamine (0.674 mL, 4.84 mmol) and DMAP (455 mg, 3.72 mmol) were added to a stirred mixture of $Boc_2O$ (1.3 mL, 5.58 mmol) and 2-((4-chloro-5-fluoro-2-nitrophenyl)amino)nicotinaldehyde (1.10 g, 3.72 mmol) in $CH_2Cl_2$ (35 mL) and the mixture was stirred at RT for 1 h. The solvent was removed under reduced pressure and the residue was purified with ISCO column (80 g silica gel eluting with 0-50% EtOAc/hexane gradient) to afford tert-butyl (4-chloro-5-fluoro-2-nitrophenyl)(3-formylpyridin-2-yl)carbamate as a syrup.

Step 3:

A mixture of tert-butyl (4-chloro-5-fluoro-2-nitrophenyl)(3-formylpyridin-2-yl)carbamate (1.10 g, 2.78 mol) in MeOH (14 mL) and ethyl acetate (7 mL), and 3% Pt-0.6% V/C (165 mg, 0.639 mmol) was loaded into a flask fitted with a hydrogen gas balloon. The reaction mixture was $H_2$/vacuum exchanged three times before it was stirred for overnight at RT. The reaction mixture was diluted with $CH_2Cl_2$ and filtered through a short pad of celite and washed with $CH_2Cl_2$. The solvent was removed under reduced pressure to afford tert-butyl 8-chloro-9-fluoro-5H-benzo[b]pyrido[2,3-e][1,4]diazepine-11(6H)-carboxylate. MS: 350 (M+1)

Step 4:

1-(2,2,2-Trifluoroethyl)piperidine-4-carboxylic acid (266 mg, 1.258 mmol) was dissolved in $CH_2Cl_2$ (3 mL) and one drop of DMF. Oxalyl chloride (0.11 mL, 1.26 mmol) was added at RT. The solvent was evaporated in 1 h to give the acyl chloride intermediate. To another 2 drum vial with a vent cap was charged with tert-butyl 8-chloro-9-fluoro-5H-benzo[b]pyrido[2,3-e][1,4]diazepine-11(6H)-carboxylate (400 mg, 1.144 mmol), DMAP (140 mg, 1.144 mmol) and DCE (3 mL). The mixture was heated to 80° C. The previously made acyl chloride was suspended in DCE (1 mL) and added to the hot mixture. The reaction vial was sealed and heated for 1 hour. The reaction was quenched with saturated aqueous sodium bicarbonate solution. The aqueous phase was extracted with EtOAc, and organic phase was washed with brine and dried over $Mg_2SO_4$. The solvent was removed under reduced pressure and the residue was subjected to column chromatography (40 g silica gel, eluting with 0-70% EtOAc/Hex) to give a mixture of products. The mixture of products was dissolved in DCM (3 mL) and treated with $Boc_2O$ (0.319 mL, 1.372 mmol), triethylamine (0.191 mL, 1.372 mmol) and DMAP (140 mg, 1.144 mmol). The mixture was stirred at RT for 1 h. The solvent was removed and the residue was subjected to column chromatography (40 g silica gel, eluting with 0-70% EtOAc/hexane gradient) to afford tert-butyl 8-chloro-9-fluoro-6-(1-(2,2,2-trifluoroethyl)piperidine-4-carbonyl)-5H-benzo[b]pyrido[2,3-e][1,4]diazepine-11(6H)-carboxylate as a foam. MS: 543 (M+1).

Intermediate 8: (Trans-4-isopropoxycyclohexyl){8-[(1S,4S)-2-oxa-5-azabicyclo[2.2.2]oct-5-yl]-5,11-dihydro-6H-pyrido[2,3-b][1,5]benzodiazepin-6-yl}methanone

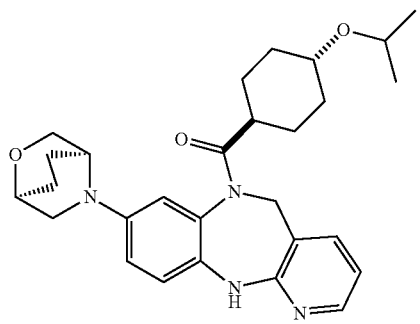

Step 1:

To a microwave vial containing 8-bromo-6,11-dihydro-5H-benzo[b]pyrido[2,3-e][1,4]diazepine, HCl salt (300 mg, 0.960 mmol) and PS-$PPh_3$ (2.06 mmol/g loading, 1.4 g, 2.9 mmol) was added a mixture of trans 4-isopropoxycyclohexanecarboxylic acid (0.18 g, 0.96 mmol) dissolved in acetonitrile (12 mL). Trichloroacetonitrile (0.48 mL, 4.8 mmol) was added and the vial was heated to 100° C. for 15 min in a microwave reactor. Upon cooling, the mixture was diluted with methanol, filtered, and concentrated. The residue was diluted with EtOAc and washed with sat. aq. sodium bicarbonate. The organic layer was then washed with water and brine, dried over sodium sulfate, filtered, and concentrated. The residue was purified by column chromatography on silica gel (5-50% ethyl acetate gradient in hexanes to afford (8-bromo-5,11-dihydro-6H-benzo[b]pyrido[2,3-e][1,4]diazepin-6-yl)((trans)-4-isopropoxycyclohexyl)methanone.

Step 2:

To a vial containing (8-bromo-5,11-dihydro-6H-benzo[b]pyrido[2,3-e][1,4]diazepin-6-yl)((trans)-4-isopropoxycyclohexyl)methanone (0.20 g, 0.45 mmol) was added 2-oxa-5-azabicyclo[2.2.2]octane hemioxalate (0.10 g, 0.90 mmol) and (2-dicyclohexylphosphino-2',6'-diisopropoxy-1,1'-biphenyl)[2-(2'-amino-1,1'-biphenyl)]palladium methanesulfonate (RuPhos Pd G3) (38 mg, 0.045 mmol). To the mixture was added lithium bis(trimethylsilyl)amide (1M in THF, 4.5 mL, 4.5 mmol). The vial was capped and heated to 80° C. for 4 h. Upon cooling to RT, the mixture was filtered and concentrated. The residue was purified by column chromatography on silica gel to afford the title compound as the racemate. The purified compound was then further purified by chiral SFC (IC, 2.1×25 cm, methanol with 0.25% DMEA and 25% modifier in $CO_2$) to afford (trans-4-isopropoxycyclohexyl){8-[(1S,4S)-2-oxa-5-azabicyclo[2.2.2]oct-5-yl]-5,11-dihydro-6H-pyrido[2,3-b][1,5]benzodiazepin-6-yl}methanone and (trans-4-isopropoxycyclohexyl){8-[(1R,4R)-2-oxa-5-azabicyclo[2.2.2]oct-5-yl]-5,11-dihydro-6H-pyrido[2,3-b][1,5]benzodiazepin-6-yl}methanone.

Characterization data for the first peak isolated from SFC: MS: 477 (M+1). $^1$H NMR (500 MHz, DMSO-$d_6$) δ 8.96 (s, 1H), 7.96 (d, 1H), 7.38 (d, 1H), 7.18 (d, 1H), 6.68-6.58 (m, 2H), 6.55 (s, 1H), 5.18 (d, 1H), 4.02-3.84 (m, 5H), 3.68-3.54 (m, 2H), 3.20-3.08 (m, 1H), 2.46-2.40 (m, 1H), 2.06-1.80 (m, 5H), 1.75-1.62 (m, 2H), 1.54-1.38 (m, 1H), 1.27-1.18 (m, 2H), 1.15-1.01 (m, 1H), 1.01-0.94 (m, 6H), 0.93-0.81 (m, 1H), 0.76-0.61 (m, 1H).

Characterization data for the second peak isolated from SFC: MS: 477 (M+1). $^1$H NMR (500 MHz, DMSO-$d_6$) δ 8.96 (s, 1H), 7.96 (d, 1H), 7.38 (d, 1H), 7.18 (d, 1H), 6.68-6.58 (m, 2H), 6.55 (s, 1H), 5.18 (d, 1H), 4.01-3.85 (m, 5H), 3.67-3.54 (m, 2H), 3.20-3.08 (m, 1H), 2.46-2.39 (m, 1H), 2.06-1.83 (m, 5H), 1.75-1.62 (m, 2H), 1.53-1.40 (m, 1H), 1.26-1.19 (m, 2H), 1.13-1.02 (m, 1H), 1.01-0.94 (m, 6H), 0.94-0.82 (m, 1H), 0.74-0.62 (m, 1H).

Intermediate 9: (8-((1S,4S)-2-Oxa-5-azabicyclo[2.2.2]octan-5-yl)-3-(4,4,5,5-tetramethyl-1,3,2-dioxaborolan-2-yl)-5,11-dihydro-6H-benzo[b]pyrido[2,3-e][1,4]diazepin-6-yl)(trans-4-isopropoxycyclohexyl)methanone

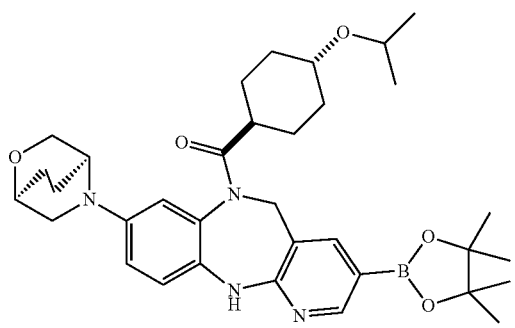 [SMILES: CC(C)O[C@H]1CC[C@H](C(=O)N2Cc3cc(B4OC(C)(C)C(C)(C)O4)cnc3Nc3ccc(N4C[C@@H]5CC[C@H]4CO5)cc32)CC1]

To a solution of (1,5-cyclooctadiene)(methoxy)iridium(I) dimer (69.5 mg, 0.105 mmol) in 2-methyl-THF (10.5 mL) in a glove box was added bis(pinacolato)diboron (293 mg, 1.15 mmol), 3,4,7,8-tetramethyl-1,10-phenanthroline (44.6 mg, 0.189 mmol) and stirred for 2 min, then added (trans-4-isopropoxycyclohexyl){8-[(1S,4S)-2-oxa-5-azabicyclo[2.2.2]oct-5-yl]-5,11-dihydro-6H-pyrido[2,3-b][1,5]benzodiazepin-6-yl}methanone (500 mg, 1.05 mmol) and the vial was sealed. The reaction mixture was microwaved at 100° C. for 60 min, cooled down, diluted with DCM, dried over Na$_2$SO$_4$, filtered and concentrated under reduced pressure. The residue was purified by column chromatography on silica (0-100% EtOAc in hexane) to afford (8-((1S,4S)-2-oxa-5-azabicyclo[2.2.2]octan-5-yl)-3-(4,4,5,5-tetramethyl-1,3,2-dioxaborolan-2-yl)-5,11-dihydro-6H-benzo[b]pyrido[2,3-e][1,4]diazepin-6-yl)(trans-4-isopropoxycyclohexyl)methanone as a solid. MS: 521 (M+1).

EXAMPLES

Example 1: (8-Chloro-3-fluoro-5,11-dihydro-6H-benzo[b]pyrido[2,3-e][1,4]diazepin-6-yl)(1-(2,2,2-trifluoroethyl)piperidin-4-yl)methanone

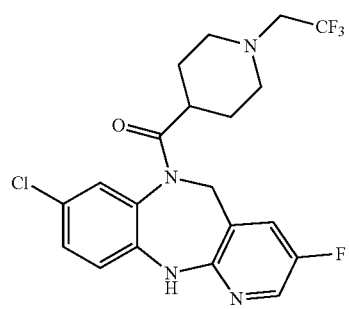 [SMILES: O=C(C1CCN(CC(F)(F)F)CC1)N1Cc2cc(F)cnc2Nc2ccc(Cl)cc21]

To a stirred solution of 1-(2,2,2-trifluoroethyl)piperidine-4-carboxylic acid (63.4 mg, 0.30 mmol) in DCM (500 μl) and one drop DMF was added oxalyl chloride (27.5 μl, 0.31 mmol) at RT. The reaction was stirred at RT for 1.5 h and then concentrated to dryness. The resulting acyl chloride was redissolved in DCE (1 mL) and added to a hot suspension of tert-butyl 8-chloro-3-fluoro-5H-benzo[b]pyrido[2,3-e][1,4]diazepine-11(6H)-carboxylate (100 mg, 0.286 mmol) in DCE (1 mL) at 80° C. DMAP (1.7 mg, 0.014 mmol) in DCE (0.5 mL) was added subsequently. The mixture was heated overnight. Upon cooling to RT, the mixture was diluted with water, extracted with ethyl acetate (3×) and the combined organic layers were washed with brine, dried over sodium sulfate, filtered, and concentrated under reduced pressure. The residue was purified by column chromatography (24 g silica gel, EtOAc:EtOH (3:1) in hexanes, 0-70%) to afford (8-chloro-3-fluoro-5,11-dihydro-6H-benzo[b]pyrido[2,3-e][1,4]diazepin-6-yl)(1-(2,2,2-trifluoroethyl)piperidin-4-yl)methanone as a solid. MS: 443 (M+1).

Example 2: (8-Chloro-3-fluoro-5,11-dihydro-6H-benzo[b]pyrido[2,3-e][1,4]diazepin-6-yl)(trans-4-isopropoxycyclohexyl)methanone

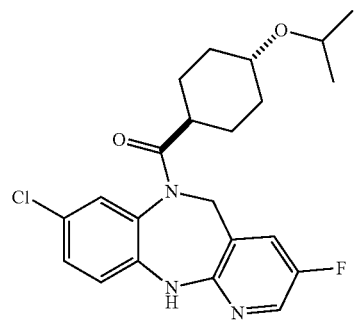

To a stirred solution of trans-4-isopropoxycyclohexanecarboxylic acid (56 mg, 0.30 mmol) in DCM (500 μl) and one drop DMF was added oxalyl chloride (28 μl, 0.31 mmol) at RT. The reaction was stirred at RT for 1.5 h and then concentrated to dryness. The resulting (1r,4r)-4-isopropoxycyclohexane-1-carbonyl chloride was redissolved in DCE (1 mL) and added to a hot suspension of tert-butyl 8-chloro-3-fluoro-5H-benzo[b]pyrido[2,3-e][1,4]diazepine-11(6H)-carboxylate (100 mg, 0.286 mmol) in DCE (1 mL) at 80° C. DMAP (1.7 mg, 0.014 mmol) in DCE (0.5 mL) was added subsequently. The mixture was heated overnight. Another 1 equiv of trans-4-isopropoxycyclohexane-1-carbonyl chloride and 0.05 equivalent of DMAP were added to the reaction mixture. The reaction was heated for another 16 h before quenching with water and aq. sodium bicarbonate solution. The mixture was extracted with EtOAc, washed with brine, dried over sodium sulfate and concentrated. The residue was further treated with TFA/DCM (1 mL, 1:1) at RT for 1 h. The volatiles were removed under reduced pressure. The residue was purified by column chromatography (24 g silica gel, 0-60% EtOAc in hexane) to afford (8-chloro-3-fluoro-5,11-dihydro-6H-benzo[b]pyrido[2,3-e][1,4]diazepin-6-yl)(trans-4-isopropoxycyclohexyl)methanone as a solid. MS: 418 (M+1).

Example 3: (8-Bromo-3-fluoro-5,11-dihydro-6H-benzo[b]pyrido[2,3-e][1,4]diazepin-6-yl)(trans-4-isopropoxycyclohexyl)methanone

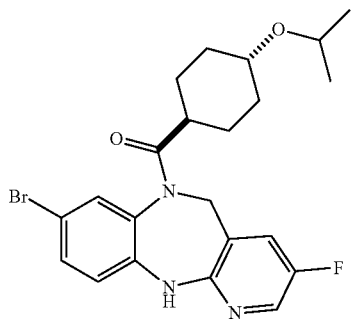 [SMILES: CC(C)O[C@H]1CC[C@H](C(=O)N2Cc3cc(F)cnc3Nc3ccc(Cl)cc32)CC1]

To a stirred solution of trans-4-isopropoxycyclohexanecarboxylic acid (275 mg, 1.48 mmol) in DCM (2.2 mL) and one drop DMF was added oxalyl chloride (0.144 mL, 1.65 mmol) at RT. The reaction was stirred at RT for 1.5 h and then concentrated to dryness. The resulting (1r,4r)-4-isopropoxycyclohexane-1-carbonyl chloride was redissolved in DCE (1.5 mL) and added to a hot suspension of tert-butyl 8-bromo-3-fluoro-5H-benzo[b]pyrido[2,3-e][1,4]diazepine-11(6H)-carboxylate (500 mg, 1.27 mmol) in DCE (4.5 mL) at 80° C. DMAP (7.7 mg, 0.063 mmol) in DCE (0.5 mL) was added subsequently. The mixture was heated overnight before quenching with water and aq. sodium bicarbonate solution. The mixture was extracted with EtOAc, washed with brine, dried over sodium sulfate and concentrated. The residue was further treated with TFA/DCM (3 mL, 1:1) at RT for 1 h. The volatiles were removed under reduced pressure. The residue was diluted with EtOAc, quenched with aq. NaHCO$_3$ solution (0.5 mL) for 5 min, dried over sodium sulfate, filtered, and concentrated. The residue was purified by column chromatography (80 g silica gel, 0-30% EtOAc in hexane) to afford (8-bromo-3-fluoro-5,11-dihydro-6H-benzo[b]pyrido[2,3-e][1,4]diazepin-6-yl)(trans-4-isopropoxycyclohexyl)methanone as a yellow solid. MS: 464 (M+1).

Example 4: (8-Chloro-3,9-difluoro-5,11-dihydro-6H-benzo[b]pyrido[2,3-e][1,4]diazepin-6-yl)(trans-4-isopropoxycyclohexyl)methanone

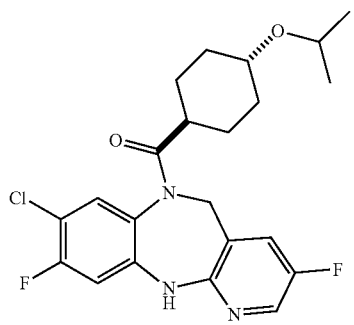 [SMILES: CC(C)O[C@H]1CC[C@H](C(=O)N2Cc3cc(F)cnc3Nc3cc(F)c(Cl)cc32)CC1]

Trans-4-isopropoxycyclohexanecarboxylic acid (223 mg, 1.196 mmol) was dissolved in DCM (8 mL) and one drop DMF. Oxalyl chloride (0.114 mL, 1.305 mmol) was added at RT and the reaction mixture was stirred at RT for 1.5 h. All volatiles were evaporated. A separate microwave vail was charged with tert-butyl 8-chloro-3,9-difluoro-5H-benzo[b]pyrido[2,3-e][1,4]diazepine-11(6H)-carboxylate (400 mg, 1.088 mmol) and DCE (15 mL). The mixture was heated to 80° C. The previously made acyl chloride was suspended in DCE and added to the hot mixture. DMAP (133 mg, 1.088 mmol) was added afterwards. The reaction vial was sealed and heated for overnight. TFA (1.666 mL, 21.75 mmol) was added and the mixture was stirred at RT for 1 h. The mixture was cooled, diluted with DCM (50 mL), washed with sat. aqueous sodium bicarbonate (40 mL), dried over MgSO$_4$, filtered and the solvent was evaporated under reduced pressure. The residue was purified by column chromatography on silica gel ISCO 40 g, eluting with EtOAc/hexane to afford (8-chloro-3,9-difluoro-5H-benzo[b]pyrido[2,3-e][1,4]diazepin-6(11H)-yl)(trans-4-isopropoxycyclohexyl)methanone as a solid. MS: 436 (M+1).

Example 5: (8-Chloro-3,9-difluoro-5,11-dihydro-6H-benzo[b]pyrido[2,3-e][1,4]diazepin-6-yl)(1-(2,2,2-trifluoroethyl)piperidin-4-yl)methanone

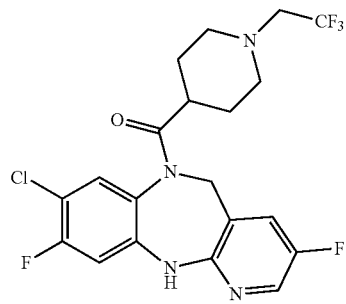 [SMILES: O=C(C1CCN(CC(F)(F)F)CC1)N1Cc2cc(F)cnc2Nc2cc(F)c(Cl)cc21]

1-(2,2,2-Trifluoroethyl)piperidine-4-carboxylic acid (189 mg, 0.897 mmol) was dissolved in DCM (2 mL) and one drop DMF. Oxalyl dichloride (0.079 mL, 0.897 mmol) was added at RT for 1 h before solvent was evaporated under reduced pressure to give the acyl chloride intermediate. To another 2 drum vial with vent cap was charged with tert-butyl 8-chloro-3,9-difluoro-5H-benzo[b]pyrido[2,3-e][1,4]diazepine-11(6H)-carboxylate (300 mg, 0.816 mmol), DMAP (100 mg, 0.816 mmol), and DCE (3.5 mL). The mixture was heated to 80° C. The previously made acyl chloride was suspended in DCE (0.5 mL) and added to the hot mixture. The reaction vial was sealed and heated for 1 h. The reaction was quenched with sodium bicarbonate solution and extracted with EtOAc. The organic phase was washed with brine, dried over Mg$_2$SO$_4$, and filtered. Solvent was removed under reduced pressure and the residue was subjected to column chromatography eluting with 0-70% EtOAc/Hex on ISCO silica gel column (24 g) to afford (8-chloro-3,9-difluoro-5H-benzo[b]pyrido[2,3-e][1,4]diazepin-6(11H)-yl)(1-(2,2,2-trifluoroethyl)piperidin-4-yl)methanone as a solid. MS: 461 (M+1).

Example 6: (8-((1S,4S)-2-Oxa-5-azabicyclo[2.2.1]heptan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone

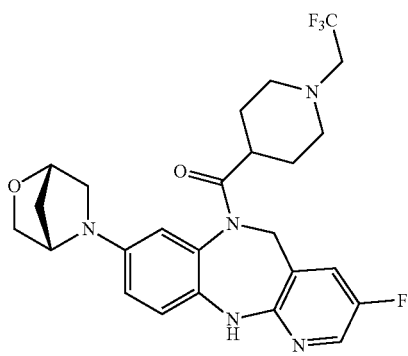 [SMILES: O=C(C1CCN(CC(F)(F)F)CC1)N1Cc2cc(F)cnc2Nc2ccc(N3C[C@@H]4C[C@H]3CO4)cc21]

To an oven-dried, nitrogen cooled microwave vial was added (8-chloro-3-fluoro-5H-benzo[b]pyrido[2,3-e][1,4]diazepin-6(11H)-yl)(1-(2,2,2-trifluoroethyl)piperidin-4-yl)methanone (80 mg, 0.18 mmol), (1S,4S)-2-oxa-5-azabicyclo[2.2.1]heptane (36 mg, 0.36 mmol), RuPhos-G3-palladacycle (7.4 mg, 9.03 μmol) and Ruphos (4.2 mg, 9.03 μmol). The vial was evacuated and filled with nitrogen and then lithium bis(trimethylsilyl)amide (1.0M in THF, 1.1 mL, 1.1 mmol) was added via syringe. The reaction was heated to 80° C. overnight. Upon cooling to RT, the mixture was diluted with water, extracted with EtOAc (2×) and the combined organic layers were washed with brine, dried over sodium sulfate, filtered, and concentrated under reduced pressure. The residue was purified by mass triggered reverse phase HPLC (ACN/water) to afford (8-((1S,4S)-2-oxa-5-azabicyclo[2.2.1]heptan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone as a solid. MS: 506 (M+1).

$^1$H NMR (500 MHz, Methanol-$d_4$) δ 7.88 (d, J=2.8 Hz, 1H), 7.36-7.29 (m, 1H), 7.09 (dd, J=8.8, 2.1 Hz, 1H), 6.67 (dd, J=8.8, 2.7 Hz, 1H), 6.55 (dd, J=5.4, 2.7 Hz, 1H), 5.30 (dd, J=15.2, 3.5 Hz, 1H), 4.65 (t, J=1.9 Hz, 1H), 4.48 (dt, J=15.7, 1.5 Hz, 1H), 4.03 (dd, J=15.1, 1.8 Hz, 1H), 3.90-3.82 (m, 2H), 3.58 (td, J=9.2, 1.6 Hz, 1H), 3.11-2.89 (m, 4H), 2.82-2.75 (m, 1H), 2.63 (dtt, J=15.3, 11.6, 3.7 Hz, 1H), 2.23 (dtd, J=19.2, 11.7, 3.0 Hz, 1H), 2.09-1.74 (m, 5H), 1.52-1.40 (m, 1H), 1.36-1.27 (m, 1H).

The compounds in Table 1 were prepared using the methodology herein and the general procedure described in Example 6.

TABLE 1

| Ex. No. | Structure | Chemical Name | [M + H]+ |
|---|---|---|---|
| 7 | 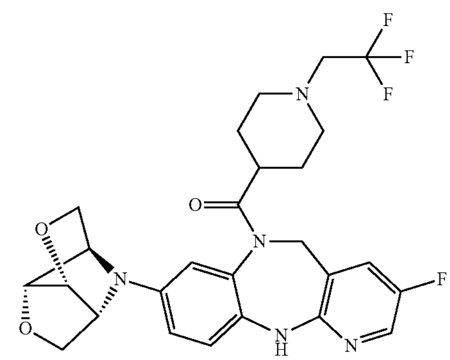 [SMILES: O=C(C1CCN(CC(F)(F)F)CC1)N1Cc2cc(F)cnc2Nc2ccc(N3[C@@H]4CO[C@H]5[C@@H]4OC[C@H]53)cc21] | (3-fluoro-8-((3R,3aR,6R,6aR)-hexahydro-3,6-epiminofuro[3,2-b]furan-7-yl)-5,11-dihydro-6H-benzo[b]pyrido[2,3-e][1,4]diazepin-6-yl)(1-(2,2,2-trifluoroethyl)piperidin-4-yl)methanone | 534 |
| 8 | Isomer 1 | (8-(2-oxa-5-azabicyclo[2.2.2]octan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone | 520 |

TABLE 1-continued

| Ex. No. | Structure | Chemical Name | [M + H]+ |
|---|---|---|---|
| 9 | 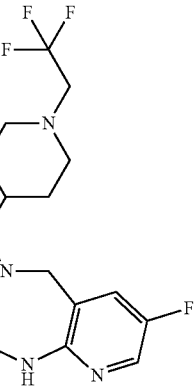 Isomer 2 | (8-(2-oxa-5-azabicyclo[2.2.2]octan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone | 520 |
| 10 | 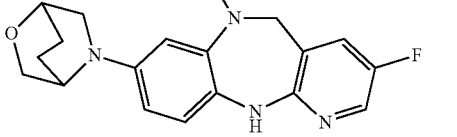 | (3-fluoro-8-((1R,3r,5S)-3-methoxy-8-azabicyclo[3.2.1]octan-8-yl)-5,11-dihydro-6H-benzo[b]pyrido[2,3-e][1,4]diazepin-6-yl)(1-(2,2,2-trifluoroethyl)piperidin-4-yl)methanone | 548 |
| 11 | 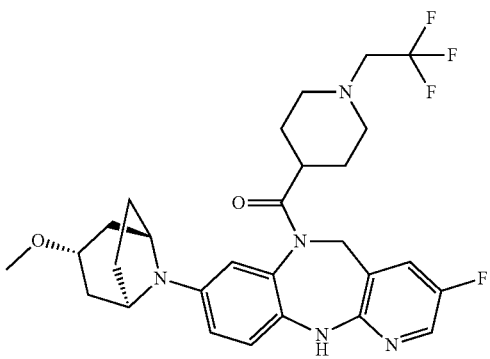 [SMILES: CO[C@H]1C[C@H]2CC[C@@H](C1)N2c1ccc2c(c1)N(C(=O)C1CCN(CC(F)(F)F)CC1)Cc1cc(F)cnc1N2] | (8-((2S,5S)-2,5-dimethylmorpholino)-3-fluoro-5,11-dihydro-6H-benzo[b]pyrido[2,3-e][1,4]diazepin-6-yl)(1-(2,2,2-trifluoroethyl)piperidin-4-yl)methanone | 522 |
| 12 | 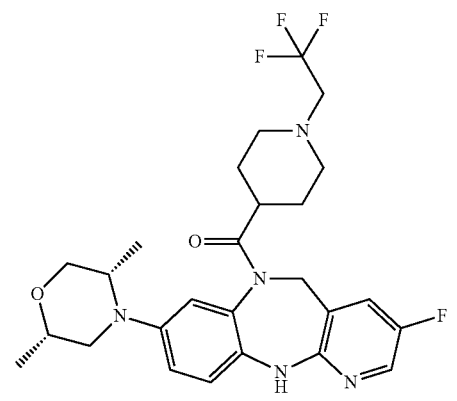 [SMILES: C[C@H]1CN(c2ccc3c(c2)N(C(=O)C2CCN(CC(F)(F)F)CC2)Cc2cc(F)cnc2N3)[C@@H](C)CO1] | (3-fluoro-8-(6-oxa-2-azaspiro[3.5]nonan-2-yl)-5,11-dihydro-6H-benzo[b]pyrido[2,3-e][1,4]diazepin-6-yl)(1-(2,2,2-trifluoroethyl)piperidin-4-yl)methanone | 535 |

TABLE 1-continued

| Ex. No. | Structure | Chemical Name | [M + H]+ |
|---|---|---|---|
| 13 | Isomer 1 | [3-fluoro-8-(2-oxa-5-azabicyclo[2.2.2]oct-5-yl)-5,11-dihydro-6H-pyrido[2,3-b][1,5]benzodiazepin-6-yl][trans-4-(propan-2-yloxy)cyclohexyl]methanone | 496 |
| 14 | Isomer 2 | [3-fluoro-8-(2-oxa-5-azabicyclo[2.2.2]oct-5-yl)-5,11-dihydro-6H-pyrido[2,3-b][1,5]benzodiazepin-6-yl][trans-4-(propan-2-yloxy)cyclohexyl]methanone | 496 |
| 15 | 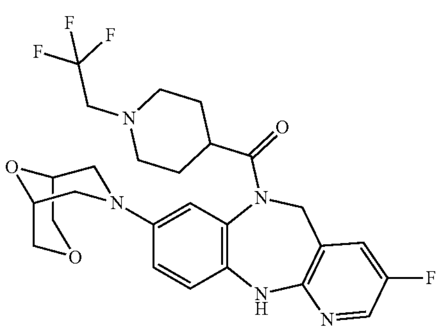 [SMILES: O=C(C1CCN(CC(F)(F)F)CC1)N1Cc2cc(F)cnc2Nc2ccc(N3CC4COCC(C3)O4)cc21] | (8-((1R,5S)-3,9-dioxa-7-azabicyclo[3.3.1]nonan-7-yl)-3-fluoro-5,11-dihydro-6H-benzo[b]pyrido[2,3-e][1,4]diazepin-6-yl)(1-(2,2,2-trifluoroethyl)piperidin-4-yl)methanone | 536 |
| 16 | 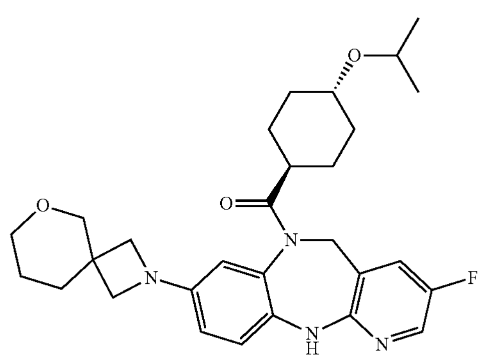 [SMILES: CC(C)O[C@H]1CC[C@H](C(=O)N2Cc3cc(F)cnc3Nc3ccc(N4CC5(CCCOC5)C4)cc32)CC1] | [3-fluoro-8-(6-oxa-2-azaspiro[3.5]non-2-yl)-5,11-dihydro-6H-pyrido[2,3-b][1,5]benzodiazepin-6-yl][trans-4-(propan-2-yloxy)cyclohexyl]methanone | 510 |

TABLE 1-continued

| Ex. No. | Structure | Chemical Name | [M + H]+ |
|---|---|---|---|
| 17 | 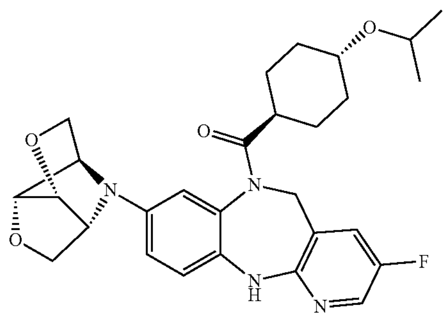 [SMILES: CC(C)O[C@H]1CC[C@H](C(=O)N2Cc3cc(F)cnc3Nc3ccc(N4[C@@H]5CO[C@H]6[C@@H]5OC[C@H]64)cc32)CC1] | (3-fluoro-8-((3R,3aR,6R,6aR)-hexahydro-3,6-epiminofuro[3,2-b]furan-7-yl)-5,11-dihydro-6H-benzo[b]pyrido[2,3-e][1,4]diazepin-6-yl)(trans-4-isopropoxycyclohexyl)methanone | 510 |
| 18 | 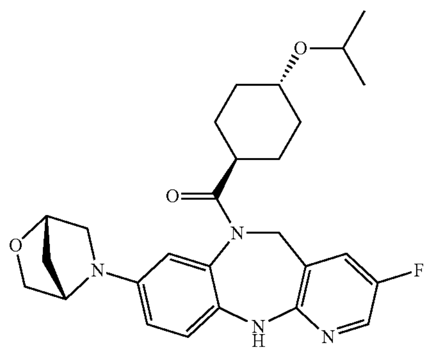 [SMILES: CC(C)O[C@H]1CC[C@H](C(=O)N2Cc3cc(F)cnc3Nc3ccc(N4C[C@@H]5C[C@H]4CO5)cc32)CC1] | (8-((1S,4S)-2-oxa-5-azabicyclo[2.2.1]heptan-5-yl)-3-fluoro-5,11-dihydro-6H-benzo[b]pyrido[2,3-e][1,4]diazepin-6-yl)(trans-4-isopropoxycyclohexyl)methanone | 481 |
| 19 | 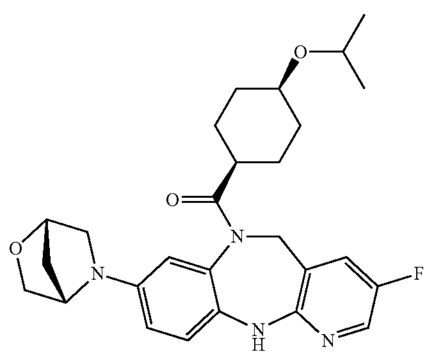 [SMILES: CC(C)O[C@H]1CC[C@@H](C(=O)N2Cc3cc(F)cnc3Nc3ccc(N4C[C@@H]5C[C@H]4CO5)cc32)CC1] | (8-((1S,4S)-2-oxa-5-azabicyclo[2.2.1]heptan-5-yl)-3-fluoro-5,11-dihydro-6H-benzo[b]pyrido[2,3-e][1,4]diazepin-6-yl)(cis-4-isopropoxycyclohexyl)methanone | 481 |
| 20 | 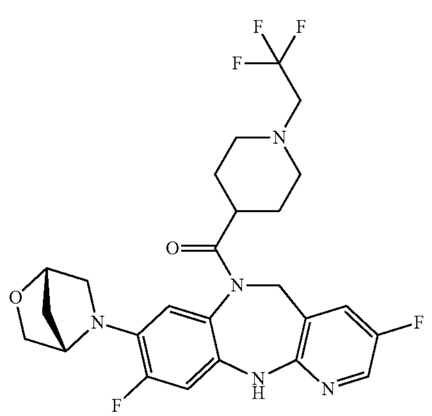 [SMILES: O=C(C1CCN(CC(F)(F)F)CC1)N1Cc2cc(F)cnc2Nc2cc(F)c(N3C[C@@H]4C[C@H]3CO4)cc21] | (8-((1S,4S)-2-oxa-5-azabicyclo[2.2.1]heptan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone | 524 |

TABLE 1-continued

| Ex. No. | Structure | Chemical Name | [M + H]+ |
|---|---|---|---|
| 21 | 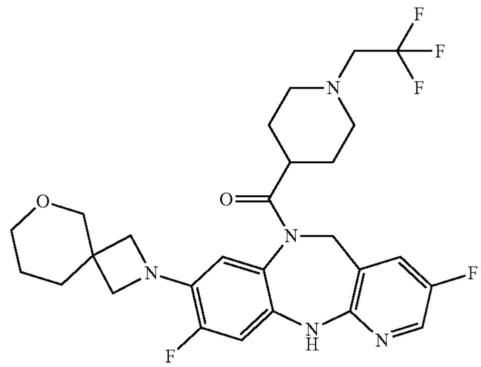 [SMILES: O=C(C1CCN(CC(F)(F)F)CC1)N1Cc2cc(F)cnc2Nc2cc(F)c(N3CC4(CCCOC4)C3)cc21] | (3,9-difluoro-8-(6-oxa-2-azaspiro[3.5]nonan-2-yl)-5,11-dihydro-6H-benzo[b]pyrido[2,3-e][1,4]diazepin-6-yl)(1-(2,2,2-trifluoroethyl)piperidin-4-yl)methanone | 553 |
| 22 | 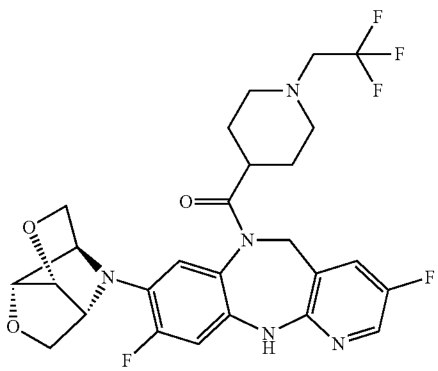 [SMILES: O=C(C1CCN(CC(F)(F)F)CC1)N1Cc2cc(F)cnc2Nc2cc(F)c(N3[C@@H]4CO[C@H]5[C@@H]4OC[C@H]53)cc21] | (3,9-difluoro-8-((3R,3aR,6R,6aR)-hexahydro-3,6-epiminofuro[3,2-b]furan-7-yl)-5,11-dihydro-6H-benzo[b]pyrido[2,3-e][1,4]diazepin-6-yl)(1-(2,2,2-trifluoroethyl)piperidin-4-yl)methanone | 553 |
| 23 | 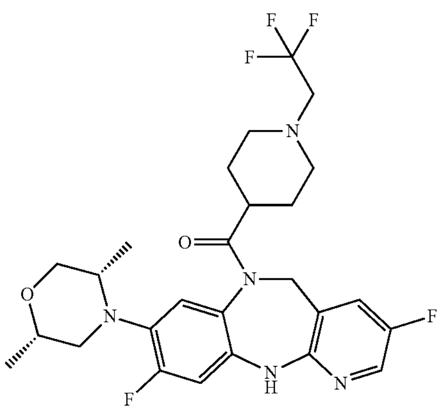 [SMILES: C[C@H]1CN(c2cc3c(cc2F)Nc2ncc(F)cc2CN3C(=O)C2CCN(CC(F)(F)F)CC2)[C@@H](C)CO1] | (8-((2S,5S)-2,5-dimethylmorpholino)-3,9-difluoro-5,11-dihydro-6H-benzo[b]pyrido[2,3-e][1,4]diazepin-6-yl)(1-(2,2,2-trifluoroethyl)piperidin-4-yl)methanone | 541 |
| 24 | 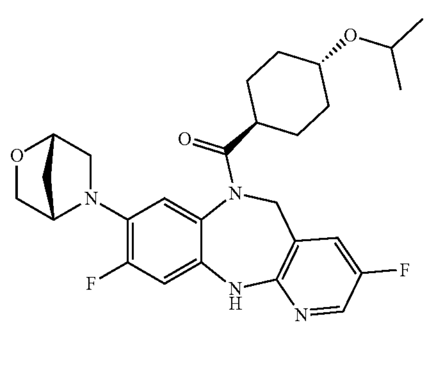 [SMILES: CC(C)O[C@H]1CC[C@H](C(=O)N2Cc3cc(F)cnc3Nc3cc(F)c(N4C[C@@H]5C[C@H]4CO5)cc32)CC1] | {3,9-difluoro-8-[(1S,4S)-2-oxa-5-azabicyclo[2.2.1]hept-5-yl]-5,11-dihydro-6H-pyrido[2,3-b][1,5]benzodiazepin-6-yl}[trans-4-(propan-2-yloxy)cyclohexyl]methanone | 500 |

TABLE 1-continued

| Ex. No. | Structure | Chemical Name | [M + H]+ |
|---|---|---|---|
| 25 | 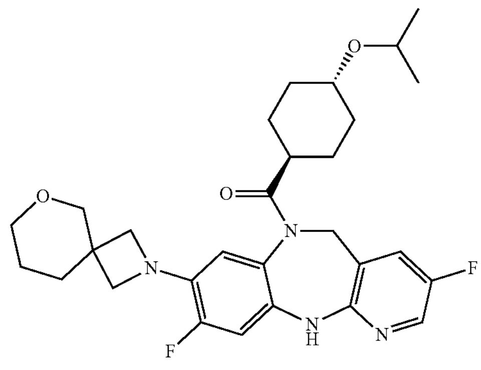 [SMILES: CC(C)O[C@H]1CC[C@H](C(=O)N2Cc3cc(F)cnc3Nc3cc(F)c(N4CC5(CCCOC5)C4)cc32)CC1] | [3,9-difluoro-8-(6-oxa-2-azaspiro[3.5]non-2-yl)-5,11-dihydro-6H-pyrido[2,3-b][1,5]benzodiazepin-6-yl][trans-4-(propan-2-yloxy)cyclohexyl]methanone | 528 |
| 26 | 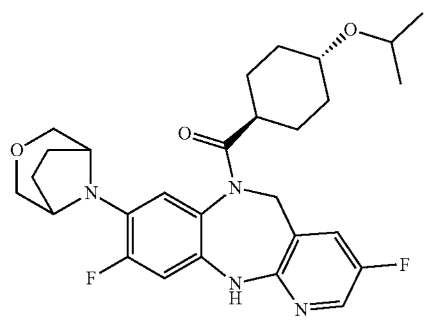 [SMILES: CC(C)O[C@H]1CC[C@H](C(=O)N2Cc3cc(F)cnc3Nc3cc(F)c(N4C5CCC4COC5)cc32)CC1] | [3,9-difluoro-8-(3-oxa-8-azabicyclo[3.2.1]oct-8-yl)-5,11-dihydro-6H-pyrido[2,3-b][1,5]benzodiazepin-6-yl][trans-4-(propan-2-yloxy)cyclohexyl]methanone | 514 |
| 27 | 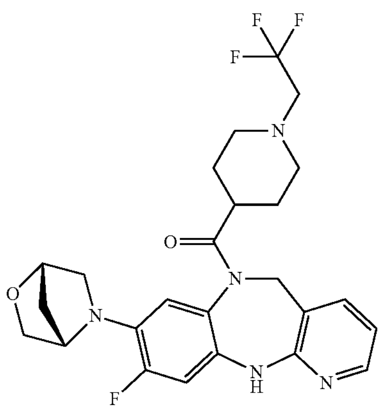 [SMILES: O=C(C1CCN(CC(F)(F)F)CC1)N1Cc2cccnc2Nc2cc(F)c(N3C[C@@H]4C[C@H]3CO4)cc21] | (8-((1S,4S)-2-oxa-5-azabicyclo[2.2.1]heptan-5-yl)-9-fluoro-5,11-dihydro-6H-benzo[b]pyrido[2,3-e][1,4]diazepin-6-yl)(1-(2,2,2-trifluoroethyl)piperidin-4-yl)methanone | 506 |
| 28 | 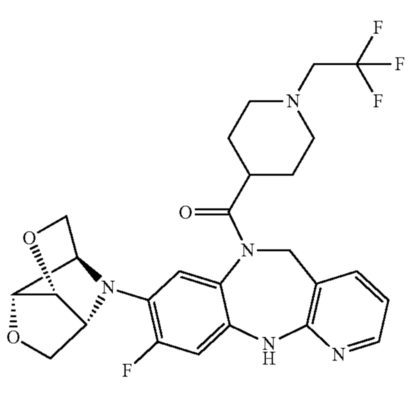 [SMILES: O=C(C1CCN(CC(F)(F)F)CC1)N1Cc2cccnc2Nc2cc(F)c(N3[C@@H]4CO[C@H]5[C@@H]4OC[C@H]53)cc21] | (9-fluoro-8-((3R,3aR,6R,6aR)-hexahydro-3,6-epiminofuro[3,2-b]furan-7-yl)-5,11-dihydro-6H-benzo[b]pyrido[2,3-e][1,4]diazepin-6-yl)(1-(2,2,2-trifluoroethyl)piperidin-4-yl)methanone | 534 |

TABLE 1-continued

| Ex. No. | Structure | Chemical Name | [M + H]+ |
|---|---|---|---|
| 29 | 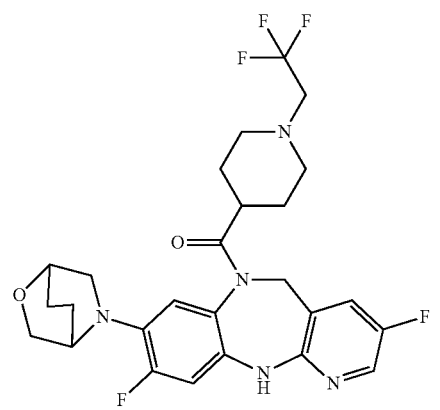 [SMILES: O=C(C1CCN(CC(F)(F)F)CC1)N1Cc2cc(F)cnc2Nc2cc(F)c(N3CC4CCC3CO4)cc21] | (8-(2-oxa-5-azabicyclo[2.2.2]octan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone | 539 |
| 30 | 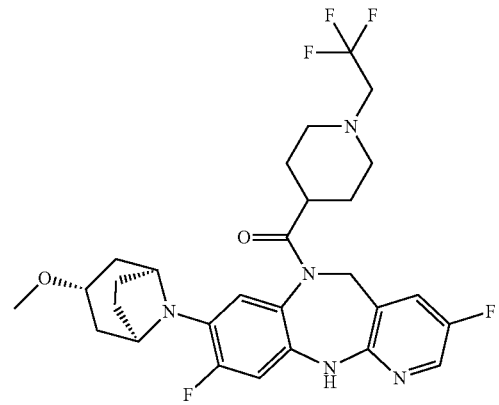 [SMILES: CO[C@H]1C[C@H]2CC[C@@H](C1)N2c1cc2c(cc1F)Nc1ncc(F)cc1CN2C(=O)C1CCN(CC(F)(F)F)CC1] | (3,9-difluoro-8-((1R,3r,5S)-3-methoxy-8-azabicyclo[3.2.1]octan-8-yl)-5,11-dihydro-6H-benzo[b]pyrido[2,3-e][1,4]diazepin-6-yl)(1-(2,2,2-trifluoroethyl)piperidin-4-yl)methanone | 567 |
| 31 | 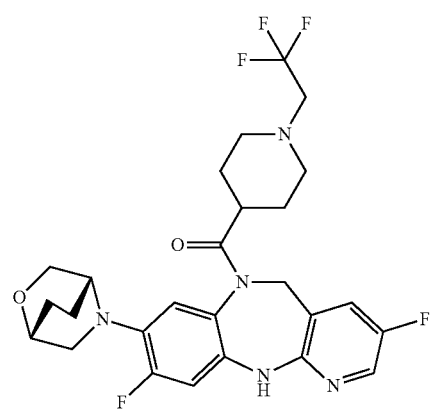 [SMILES: O=C(C1CCN(CC(F)(F)F)CC1)N1Cc2cc(F)cnc2Nc2cc(F)c(N3C[C@H]4CC[C@@H]3CO4)cc21] | (8-((1R,4R)-2-oxa-5-azabicyclo[2.2.2]octan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone | 539 |

TABLE 1-continued

| Ex. No. | Structure | Chemical Name | [M + H]+ |
|---|---|---|---|
| 32 | 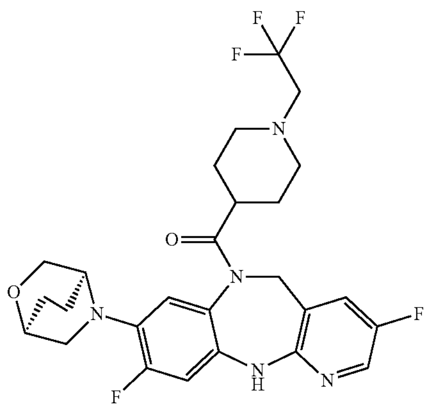 [SMILES: O=C(C1CCN(CC(F)(F)F)CC1)N1Cc2cc(F)cnc2Nc2cc(F)c(N3C[C@@H]4CC[C@H]3CO4)cc21] | (8-((1S,4S)-2-oxa-5-azabicyclo[2.2.2]octan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone | 539 |

Examples 33 and 34: (8-((S)-1,4-Dioxan-2-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone and (8-((R)-1,4-dioxan-2-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone

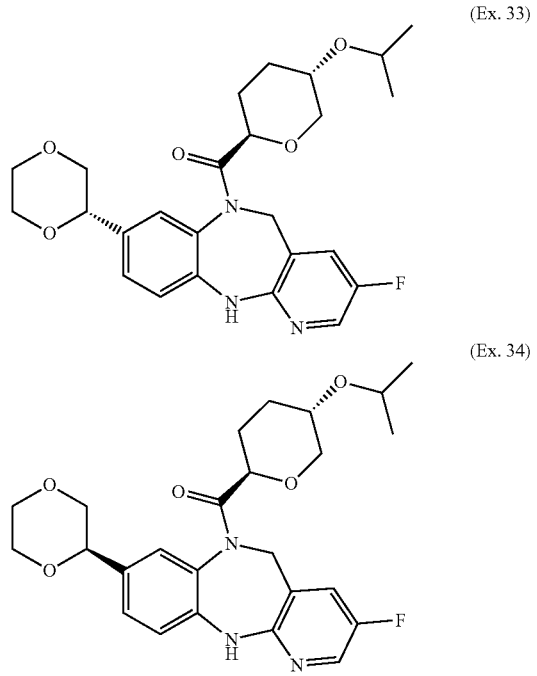

(Ex. 33)

(Ex. 34)

Step 1:
To a round bottle flask equipped with a stir bar was added 8-bromo-3-fluoro-6,11-dihydro-5H-benzo[b]pyrido[2,3-e][1,4]diazepine (24 g, 82 mmol), 2-(5,6-dihydro-1,4-dioxin-2-yl)-4,4,5,5-tetramethyl-1,3,2-dioxaborolane (26.0 g, 122 mmol), potassium phosphate, tribasic (204 ml, 408 mmol) and THF (272 ml). The 3rd Generation X-Phos precatalyst (3.45 g, 4.08 mmol) was added last and the flask was purged with nitrogen. The reaction mixture was refluxed for 45 min under nitrogen (70° C. internal temperature). Upon cooling, the reaction mixture was diluted with water, extracted with EtOAc (3×), dried over sodium sulfate, filtered, and concentrated in vacuo. The residue was diluted with DCM and triturated with hexanes. The solid was filtered off and washed with hexanes. The filtrate was again concentrated in vacuo, dissolved in minimal DCM and with hexanes. The solid was filtered off and washed with hexanes. The combined solids was dried in vacuo to afford (8-(5,6-dihydro-1,4-dioxin-2-yl)-3-fluoro-6,11-dihydro-5H-benzo[b]pyrido[2,3-e][1,4]diazepine).

Step 2:
8-(5,6-Dihydro-1,4-dioxin-2-yl)-3-fluoro-6,11-dihydro-5H-benzo[b]pyrido[2,3-e][1,4]diazepine (1.7 g, 5.68 mmol) and palladium on carbon (0.60 g, 0.568 mmol) were added to a round bottle flask purged with N₂ gas. MeOH (114 ml) was added and a three-way stop cock with a H₂ balloon was attached and the mixture was subjected to alternating vacuum and H₂ gas 3 times. The mixture was then stirred under an atmosphere of H₂ for 20 h. The mixture was then subjected to alternating vacuum and N₂ gas 3 times before the balloon was removed and the reaction vessel was flushed with a stream of N₂ gas. The mixture was then carefully filtered through celite and washed with DCM:MeOH. The filtrate was concentrated in vacuo and then dissolved in minimal DCM and triturated with hexanes. The solid was filtered off, washed with hexanes and dried in vacuo to afford the product 8-(1,4-dioxan-2-yl)-3-fluoro-6,11-dihydro-5H-benzo[b]pyrido[2,3-e][1,4]diazepine. The filtrate was concentrated in vacuo. The residue was purified by MPLC (30-100% EtOAc:Hex) to afford more desired product. The precipitate was combined with the product isolated by MPLC and the combined batch was further purified by chiral SFC (Chiralcel OD-H, 21×250 mm, isopropanol+0.25% dimethyl ethyl amine modifier in CO₂) to separate the enanatiomers (peak 1 and peak 2).

Step 3:
(2R,5S)-5-Isopropoxytetrahydro-2H-pyran-2-carboxylic acid (0.137 g, 0.730 mmol) was dissolved in DCM (6.64 ml) and one drop DMF was added. Oxalyl chloride (0.067 ml, 0.763 mmol) was added at RT. After 15 min, the reaction was evaporated and dried. To a different flask was added with 8-(1,4-dioxan-2-yl)-3-fluoro-6,11-dihydro-5H-benzo[b]pyrido[2,3-e][1,4]diazepine (peak 1 from SFC, 0.2 g, 0.664 mmol) and DCE. The mixture was heated at 80° C., followed by the addition of a solution of the freshly made acyl chloride suspension in DCE and DMAP (4 mg, 0.033 mmol). The mixture was heated for 3 h. Once completed, the reaction was extracted 3 times with saturated NaHCO₃ and EtOAc. The organic layer was dried over anhydrous magnesium sulfate and concentrated in vacuo. The residue was purified by MPLC (0-75% EtOAc:Hex) to afford (8-((S)-1,4-dioxan-2-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone. MS: 472 (M+1). ¹H NMR (600 MHz, d₆-DMSO): δ 9.45-9.49 (m, 1H); 8.02 (d, J=2.8 Hz, 1H); 7.52 (t, J=10.7 Hz, 1H); 7.16-7.29 (m, 3H); 5.17 (t, J=14.6 Hz, 1H); 4.48 (t, J=9.2 Hz, 1H); 3.45-3.92 (m, 8H); 2.77 (t, J=10.3 Hz, 1H); 2.34-2.39 (m, 1H); 1.83-1.94 (m, 2H); 1.43-1.55 (m, 2H); 1.02-1.19 (m, 2H); 0.90-0.98 (m, 6H).

Step 4:

(2R,5S)-5-Isopropoxytetrahydro-2H-pyran-2-carboxylic acid (0.350 g, 1.862 mmol) was dissolved in DCM (17 ml) and catalytic DMF was added. Oxalyl chloride (0.170 ml, 1.95 mmol) was added at RT. After 30 min, the reaction was evaporated and dried. To a different round bottle flask was added 8-(1,4-dioxan-2-yl)-3-fluoro-6,11-dihydro-5Hbenzo[b]pyrido[2,3-e][1,4]diazepine (peak 2 from SFC, 0.51 g, 1.693 mmol) and N,N-dimethylpyridin-4-amine (10.3 mg, 0.085 mmol). The mixture was stirred in DCE and the freshly made acyl chloride in DCE was added. The mixture was heated at 80° C. for 3 h. The reaction mixture was cooled to RT, diluted with sat. aq. sodium bicarbonate and extracted with EtOAc. The combined organic layers were washed with brine, dried over anhydrous magnesium sulfate, filtered, and concentrated in vacuo. The residue was purified by MPLC (30-100% EtOAc:Hex) to afford (8-((R)-1,4-dioxan-2-yl)-3-fluoro-5,11-dihydro-6H-benzo[b]pyrido[2,3-e][1,4]diazepin-6-yl)((2R,5 S)-5-isopropoxytetrahydro-2H-pyran-2-yl)methanone. MS: 472 (M+1). ¹H NMR (600 MHz, d₆-DMSO): δ 9.45-9.49 (m, 1H); 8.02 (d, J=2.8 Hz, 1H); 7.49-7.53 (m, 1H); 7.14-7.31 (m, 3H); 5.16 (dd, J=15.0, 11.9 Hz, 1H); 4.48 (d, J=10.1 Hz, 1H); 3.45-3.99 (m, 8H); 2.75 (t, J=10.5 Hz, 1H); 2.40 (t, J=10.3 Hz, 1H); 1.82-2.02 (m, 2H); 1.40-1.66 (m, 2H); 1.12-1.24 (m, 2H); 0.91-0.97 (m, 6H).

Examples 35 and 36: (8-(1,4-Dioxan-2-yl)-3,9-difluoro-5H-benzo[b]pyrido[2,3-e][1,4]diazepin-6(11H)-yl)((2R,5S)-5-isopropoxytetrahydro-2H-pyran-2-yl)methanone, both enantiomers

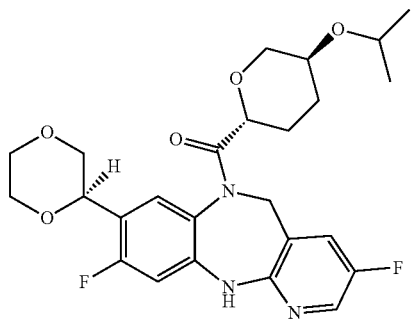

(Ex.35)

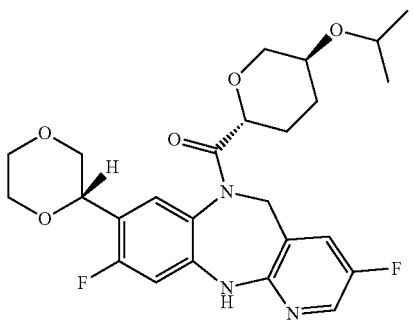

(Ex.36)

Step 1:

To a microwave vial equipped with a stir bar was added tert-butyl 8-chloro-3,9-difluoro-5H-benzo[b]pyrido[2,3-e][1,4]diazepine-11(6H)-carboxylate (446 mg, 1.21 mmol), 2-(5,6-dihydro-1,4-dioxin-2-yl)-4,4,5,5-tetramethyl-1,3,2-dioxaborolane (514 mg, 2.42 mmol), potassium phosphate, tribasic (12.1 mL, 6.06 mmol) and THF (7.5 mL). The 3rd Generation X-Phos Pd precatalyst (103 mg, 0.121 mmol) was added last and the vial was purged with nitrogen. The vial was sealed and heated to 100° C. for 45 min in the microwave. The mixture was cooled, water (10 mL) was added and the mixture was extracted with EtOAc (2×10 mL). The combined organic fractions were washed with brine (saturated, 1×10 mL), dried (Na₂SO₄), filtered and the solvent evaporated under reduced pressure. The residue was purified by column chromatography on silica gel (ISCO 40 g, eluted with EtOAc/isohexane), and the fraction was collected to afford tert-butyl 8-(5,6-dihydro-1,4-dioxin-2-yl)-3,9-difluoro-5H-benzo[b]pyrido[2,3-e][1,4]diazepine-11(6H)-carboxylate as a gum.

Step 2:

Under nitrogen gas flow, palladium on carbon (143 mg, 0.134 mmol) was added to the solid of tert-butyl 8-(5,6-dihydro-1,4-dioxin-2-yl)-3,9-difluoro-5H-benzo[b]pyrido[2,3-e][1,4]diazepine-11(6H)-carboxylate (560 mg, 1.342 mmol), followed by addition of MeOH (15 mL). The reaction mixture was N₂/vacuum exchanged and then H₂/vacuum exchanged for 3 times each. The reaction mixture was stirred with H₂ balloon at RT overnight. The reaction mixture was filtered over celite, washed with MeOH, concentrated to afford tert-butyl 8-(1,4-dioxan-2-yl)-3,9-difluoro-5H-benzo[b]pyrido[2,3-e][1,4]diazepine-11(6H)-carboxylate (490 mg, 1.168 mmol, 87% yield) as a foam. The racemate was resolved by SFC (Chiral OD-H (2×25 cm) OD-H (25×0.46 cm) 20% methanol (0.1% DEA)/CO2, 100 bar 65 mL/min, 220 nm inj vol.: 0.5 mL, 20 mg/mL, (3:1) methanol:DCM) to afford two enantiomers of tert-butyl dioxan-2-yl)-3,9-difluoro-5H-benzo[b]pyrido[2,3-e][1,4]diazepine-11(6H)-carboxylate.

Step 3:

(2R,5S)-5-isopropoxytetrahydro-2H-pyran-2-carboxylic acid (12.0 mg, 0.064 mmol), tert-butyl 8-(1,4-dioxan-2-yl)-3,9-difluoro-5H-benzo[b]pyrido[2,3-e][1,4]diazepine-11(6H)-carboxylate (26.7 mg, 0.064 mmol, enantiomer 1), PS-PPh₃ (93 mg, 0.191 mmol), trichloroacetonitrile (31.9 μl, 0.318 mmol) were dissolved in acetonitrile (637 μl), placed in a sealed tube and heated under microwave irradiation at 100° C. for 10 min. The mixture was cooled and filtered through a syringe filter disk. TFA (487 μl, 6.37 mmol) was added to the filtrate and the mixture was stirred at RT overnight. The mixture was diluted with dichloromethane (20 mL), washed with aqueous sodium hydrogen carbonate (saturated, 2×10 mL), dried (Na$_2$SO$_4$), filtered and the solvent evaporated under reduced pressure. The residue was purified by column chromatography on silica gel (ISCO 12 g, eluting with EtOAc/isohexane/EtOH (76:18:6)) to afford (8-(1,4-dioxan-2-yl)-3,9-difluoro-5H-benzo[b]pyrido[2,3-e][1,4]diazepin-6(11H)-yl)((2R,5S)-5-isopropoxytetrahydro-2H-pyran-2-yl)methanone as a gum. MS: 490 (M+1)$^1$H NMR (500 MHz, Methanol-d$_4$) δ 7.96 (dd, J=8.3, 2.8 Hz, 1H), 7.52 (d, J=7.1 Hz, 1H), 7.41 (dd, J=8.2, 3.3 Hz, 1H), 6.99-6.91 (m, 1H), 5.29 (dd, J=19.0, 14.9 Hz, 1H), 4.85 (d, J=18.1 Hz, 2H), 4.05-3.59 (m, 11H), 3.47-3.37 (m, 2H), 2.99 (t, J=10.4 Hz, 1H), 2.06-1.90 (m, 1H), 1.58-1.40 (m, 1H), 1.18-0.99 (m, 6H).

Example 36 can be synthesized from the other enantiomer of tert-butyl 8-(1,4-dioxan-2-yl)-3,9-difluoro-5H-benzo[b]pyrido[2,3-e][1,4]diazepine-11(6H)-carboxylate using reaction conditions in step 3.

The compounds in Table 2 were prepared using the methodology herein and the general procedure described in Example 35 and 36.

Example 39: (3-Fluoro-8-41R,3S,5S)-3-methoxy-8-azabicyclo[3.2.1]octan-8-yl)-5,11-dihydro-6H-benzo[b]pyrido[2,3-e][1,4]diazepin-6-yl)((2R,5S)-5-isopropoxytetrahydro-2H-pyran-2-yl)methanone

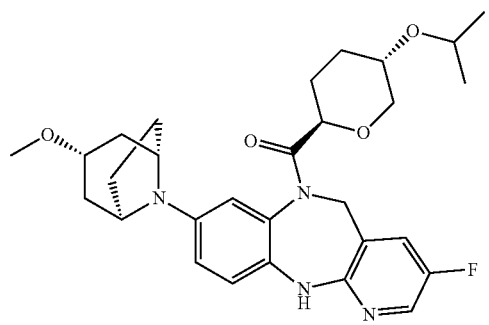 [SMILES: CO[C@H]1C[C@H]2CC[C@@H](C1)N2c1ccc2c(c1)N(C(=O)[C@H]1CC[C@H](OC(C)C)CO1)Cc1cc(F)cnc1N2]

TABLE 2

| Ex. No. | Structure | Chemical Name | [M + H]+ |
|---|---|---|---|
| 37 | Isomer 1 | (8-(1,4-dioxan-2-yl)-9-fluoro-5,11-dihydro-6H-benzo[b]pyrido[2,3-e][1,4]diazepin-6-yl)((2R,5S)-5-isopropoxytetrahydro-2H-pyran-2-yl)methanone | 472 |
| 38 | Isomer 2 | (8-(1,4-dioxan-2-yl)-9-fluoro-5,11-dihydro-6H-benzo[b]pyrido[2,3-e][1,4]diazepin-6-yl)((2R,5S)-5-isopropoxytetrahydro-2H-pyran-2-yl)methanone | 472 |

Step 1:

A solution of tert-butyl 8-chloro-3-fluoro-5H-benzo[b]pyrido[2,3-e][1,4]diazepine-11(6H)-carboxylate (1.93 g, 5.52 mmol), TEA (6.15 mL, 44.1 mmol), DMAP (0.81 g, 6.62 mmol), di-tert-butyl dicarbonate (4.82 g, 22.07 mmol) in THF (79 mL) was stirred at 70° C. for 4 h. To the reaction mixture was added another di-tert-butyl dicarbonate (2 g), DMAP (0.5 g) and TEA (2 mL). The reaction was heated for another 6 h, and then was cooled to RT and concentrated. The reaction mixture was diluted with water and extracted with EtOAc, dried over sodium sulfate, filtered and concentrated. The residue was purified by column chromatography (80 g silica gel, 0-30% EtOAc in hexane) to afford di-tert-butyl 8-chloro-3-fluoro-5H-benzo[b]pyrido[2,3-e][1,4]diazepine-6,11-dicarboxylate as a foam.

Step 2:

To a microwave vial was added di-tert-butyl 8-chloro-3-fluoro-5H-benzo[b]pyrido[2,3-e][1,4]diazepine-6,11-dicarboxylate (150 mg, 0.33 mmol), (1R,3r,5S)-3-methoxy-8-azabicyclo[3.2.1]octane, HCl (89 mg, 0.50 mmol), $Cs_2CO_3$ (652 mg, 2.00 mmol), and SPhos G2 Pd catalyst (24.0 mg, 0.033 mmol). The vial was sealed and vacuum/$N_2$ exchanged three times. DME (3.3 mL) was added and the reaction was heated to 88° C. overnight. The reaction was cooled down to RT, filtered over celite, and concentrated. The residue was purified by column chromatography (24 g silica gel, 0-70% EtOAc in hexane) to afford di-tert-butyl 3-fluoro-8-((1R,3r,5S)-3-methoxy-8-azabicyclo[3.2.1]octan-8-yl)-5H-benzo[b]pyrido[2,3-e][1,4]diazepine-6,11-dicarboxylate.

Step 3:

To a stirred solution of di-tert-butyl 3-fluoro-8-((1R,3r,5S)-3-methoxy-8-azabicyclo[3.2.1]octan-8-yl)-5H-benzo[b]pyrido[2,3-e][1,4]diazepine-6,11-dicarboxylate (127 mg, 0.23 mmol) in DCM (1 mL) was added TFA (1 mL, 12.98 mmol) at RT. The reaction was stirred at RT for 1 h. The solvents were removed under vacuum. The residue was quenched with saturated $NaHCO_3$, extracted with EtOAc, washed with brine, dried over sodium sulfate and concentrated to afford 3-fluoro-8-((1R,3r,5S)-3-methoxy-8-azabicyclo[3.2.1]octan-8-yl)-6,11-dihydro-5H-benzo[b]pyrido[2,3-e][1,4]diazepine.

Step 4:

To a stirred solution of (2R,5S)-5-isopropoxytetrahydro-2H-pyran-2-carboxylic acid (41.8 mg, 0.222 mmol) in DCM (0.35 mL) and one drop DMF was added oxalyl chloride (20.5 µl, 0.233 mmol) at RT. The reaction was stirred at RT for 1 h and then concentrated to dryness. The resulting acyl chloride was redissolved in DCE (1.5 mL) and added to a hot suspension of 3-fluoro-8-((1R,3r,5S)-3-methoxy-8-azabicyclo[3.2.1]octan-8-yl)-6,11-dihydro-5H-benzo[b]pyrido[2,3-e][1,4]diazepine (75 mg, 0.212 mmol) in DCE (0.7 mL) at 80° C. DMAP (1.3 mg) in DCE (0.5 mL) was added subsequently. The mixture was heated overnight. Upon cooling to RT, the mixture was diluted with water, extracted with ethyl acetate (2×) and the combined organic layers were washed with brine, dried over sodium sulfate, filtered, and concentrated under reduced pressure. The residue was purified by mass triggered reverse phase HPLC (ACN/water) to afford (3-fluoro-8-((1R,3S,5S)-3-methoxy-8-azabicyclo[3.2.1]octan-8-yl)-5,11-dihydro-6H-benzo[b]pyrido[2,3-e][1,4]diazepin-6-yl)((2R,5S)-5-isopropoxytetrahydro-2H-pyran-2-yl)methanone. MS: 525 (M+1). Rotamers were observed in proton NMR. The major peaks shown are as following: $^1$H NMR (500 MHz, Methanol-$d_4$) δ 7.89 (d, J=3.0 Hz, 1H), 7.34 (dd, J=8.3, 2.8 Hz, 1H), 7.09 (d, J=8.8 Hz, 1H), 6.91-6.73 (m, 2H), 5.34 (d, J=15.1 Hz, 1H), 4.21-4.15 (m, 1H), 4.12 (d, J=3.9 Hz, 2H), 4.06-3.97 (m, 2H), 3.72-3.64 (m, 1H), 3.38 (dq, J=10.3, 5.9, 5.1 Hz, 2H), 2.95 (t, J=10.4 Hz, 1H), 2.20 (d, J=7.0 Hz, 2H), 2.08 (dt, J=14.9, 4.7 Hz, 2H), 2.00-1.96 (m, 4H), 1.80 (t, J=12.1 Hz, 3H), 1.44-1.39 (m, 1H), 1.29 (d, J=5.2 Hz, 1H), 1.07 (d, J=5.9 Hz, 6H), 0.92-0.88 (m, 2H).

The compounds in Table 3 were prepared using the methodology herein and the general procedure described in Example 39.

TABLE 3

| Ex. No. | Structure | Chemical Name | [M + H]+ |
| --- | --- | --- | --- |
| 40 | 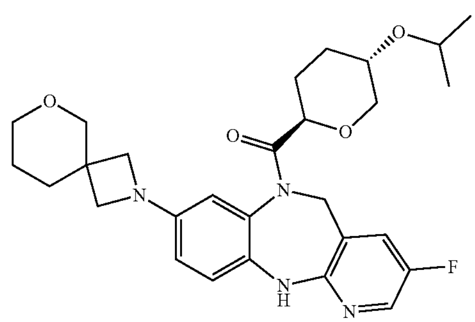 [SMILES: CC(C)O[C@H]1CC[C@H](C(=O)N2Cc3cc(F)cnc3Nc3ccc(N4CC5(CCCOC5)C4)cc32)OC1] | (3-fluoro-8-(6-oxa-2-azaspiro[3.5]nonan-2-yl)-5,11-dihydro-6H-benzo[b]pyrido[2,3-e][1,4]diazepin-6-yl)((2R,5S)-5-isopropoxytetrahydro-2H-pyran-2-yl)methanone | 512 |

TABLE 3-continued

| Ex. No. | Structure | Chemical Name | [M + H]+ |
|---|---|---|---|
| 41 | 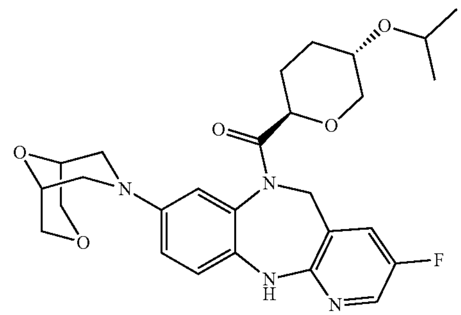 [SMILES: CC(C)O[C@H]1CC[C@H](C(=O)N2Cc3cc(F)cnc3Nc3ccc(N4CC5COCC(C4)O5)cc32)OC1] | (8-((1R,5S)-3,9-dioxa-7-azabicyclo[3.3.1]nonan-7-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone | 514 |
| 42 | 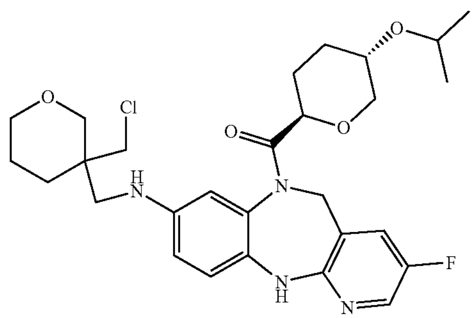 [SMILES: CC(C)O[C@H]1CC[C@H](C(=O)N2Cc3cc(F)cnc3Nc3ccc(NCC4(CCl)CCCOC4)cc32)OC1] | (8-(((3-(chloromethyl)tetrahydro-2H-pyran-3-yl)methyl)amino)-3-fluoro-5,11-dihydro-6H-benzo[b]pyrido[2,3-e][1,4]diazepin-6-yl)((2R,5S)-5-isopropoxytetrahydro-2H-pyran-2-yl)methanone | 548 |
| 43 | 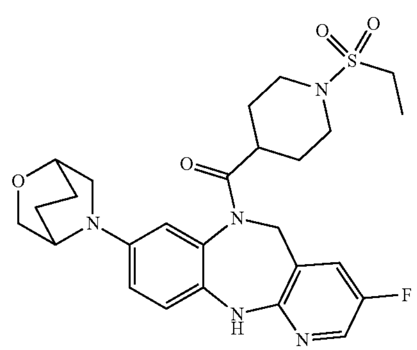 [SMILES: CCS(=O)(=O)N1CCC(C(=O)N2Cc3cc(F)cnc3Nc3ccc(N4CC5CCC4CO5)cc32)CC1] | (8-(2-oxa-5-azabicyclo[2.2.2]octan-5-yl)-3-fluoro-5,11-dihydro-6H-benzo[b]pyrido[2,3-e][1,4]diazepin-6-yl)(1-(ethylsulfonyl)piperidin-4-yl)methanone | 531 |
| 44 | 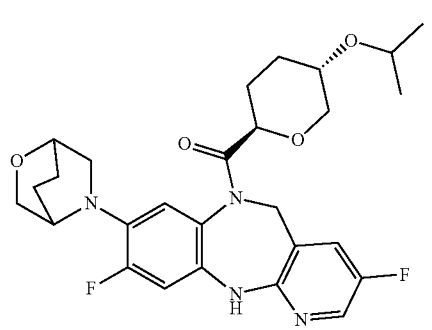 [SMILES: CC(C)O[C@H]1CC[C@H](C(=O)N2Cc3cc(F)cnc3Nc3cc(F)c(N4CC5CCC4CO5)cc32)OC1] | (8-(2-oxa-5-azabicyclo[2.2.2]octan-5-yl)-3,9-difluoro-5,11-dihydro-6H-benzo[b]pyrido[2,3-e][1,4]diazepin-6-yl)((2R,5S)-5-isopropoxytetrahydro-2H-pyran-2-yl)methanone | 516 |

Example 45: (3,9-Difluoro-8-(6-oxa-2-azaspiro[3.5]nonan-2-yl)-5H-benzo[b]pyrido[2,3-e][1,4]diazepin-6(11H)-yl)((2R,5S)-5-isopropoxytetrahydro-2H-pyran-2-yl)methanone

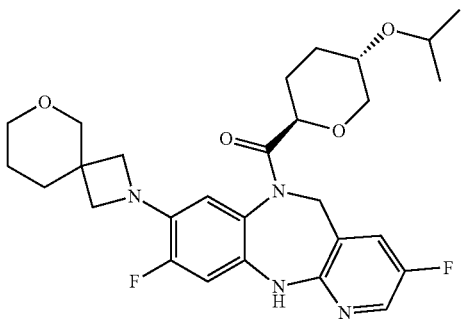 [SMILES: CC(C)O[C@H]1CC[C@H](C(=O)N2Cc3cc(F)cnc3Nc3cc(F)c(N4CC5(CCCOC5)C4)cc32)OC1]

Step 1:

To a microwave vial was charged with a solution of tert-butyl 8-chloro-3,9-difluoro-5H-benzo[b]pyrido[2,3-e][1,4]diazepine-11(6H)-carboxylate (0.1 g, 0.272 mmol), 6-oxa-2-azaspiro[3.5]nonane (0.086 g, 0.680 mmol), (2-dicyclohexylphosphino-2',6'-diisopropoxy-1,1'-biphenyl)[2-(2'-amino-1,1'-biphenyl)]palladium(II) methanesulfonate (RuPhos Pd G3) (0.011 g, 0.014 mmol) in THF (1.36 mL), and lithium bis(trimethylsilyl)amide in THF (1M, 2.72 mL, 2.72 mmol). The vial was sealed and heated at 80° C. overnight. This mixture was cooled to RT and diluted with $CH_2Cl_2$, washed with brine, dried over $MgSO_4$, filtered and concentrated. The residue was purified by column chromatography on silica gel (12 g, eluting with 0-50% EtOAc/hexane) to afford tert-butyl 3,9-difluoro-8-(6-oxa-2-azaspiro[3.5]nonan-2-yl)-5H-benzo[b]pyrido[2,3-e][1,4]diazepine-11(6H)-carboxylate as a solid.

Step 2:

To a solution of tert-butyl 3,9-difluoro-8-(6-oxa-2-azaspiro[3.5]nonan-2-yl)-5H-benzo[b]pyrido[2,3-e][1,4]diazepine-11(6H)-carboxylate (0.04 g, 0.087 mmol) in $CH_2Cl_2$ (0.5 mL) was added TFA (0.5 mL) and the reaction mixture was stirred for 1 h. The mixture was concentrated and then taken up in DCM. The reaction mixture was washed with aq. sat. $NaHCO_3$, dried over $MgSO_4$, filtered and concentrated to give a foamy-solid. This de-Boc compound, (2R,5S)-5-isopropoxytetrahydro-2H-pyran-2-carboxylic acid (0.016 g, 0.087 mmol), 2,2,2-trichloroacetonitrile (0.044 mL, 0.436 mmol), polymer bound triphenyl phosphone (0.068 g, 0.262 mmol) was dissolved in acetonitrile (0.872 mL), placed in a sealed tube and heated under microwave irradiation at 100° C. for 10 min. The mixture was cooled and filtered, washed with $CH_2Cl_2$ and the solvent was evaporated under reduced pressure. The residue was purified by column chromatography on silica gel (4 g, eluting with 0-50% EtOAc/hexane) to afford (3,9-difluoro-8-(6-oxa-2-azaspiro[3.5]nonan-2-yl)-5H-benzo[b]pyrido[2,3-e][1,4]diazepin-6(11H)-yl)((2R,5S)-5-isopropoxytetrahydro-2H-pyran-2-yl)methanone as a solid. MS: 529 (M+1), $^1$H NMR (500 MHz, Chloroform-d) δ 12.05 (s, 1H), 7.76-7.64 (m, 2H), 7.12 (m, 1H), 6.58-6.46 (m, 1H), 5.53-5.20 (m, 1H), 4.03 (dd, J=26.5, 10.2 Hz, 1H), 3.97-3.82 (m, 1H), 3.77 (s, 4H), 3.62 (d, J=33.9 Hz, 4H), 3.46 (s, 1H), 3.02 (t, J=10.4 Hz, 1H), 2.79 (m, 1H), 2.07 (d, J=12.6 Hz, 1H), 1.86 (s, 2H), 1.75 (m, 1H), 1.62 (s, 2H), 1.47 (d, J=13.9 Hz, 1H), 1.40-1.18 (m, 2H), 1.11 (td, J=6.4, 3.1 Hz, 6H).

The compounds in Table 4 were prepared using the methodology herein and the general procedure described in Example 45.

TABLE 4

| Ex. No. | Structure | Chemical Name | [M + H]+ |
| --- | --- | --- | --- |
| 46 | 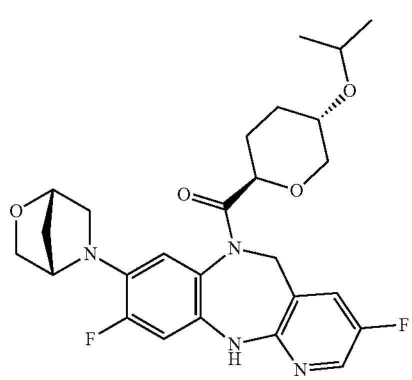 [SMILES: CC(C)O[C@H]1CC[C@H](C(=O)N2Cc3cc(F)cnc3Nc3cc(F)c(N4C[C@@H]5C[C@H]4CO5)cc32)OC1] | (8-((1S,4S)-2-oxa-5-azabicyclo[2.2.1]heptan-5-yl)-3,9-difluoro-5,11-dihydro-6H-benzo[b]pyrido[2,3-e][1,4]diazepin-6-yl)((2R,5S)-5-isopropoxytetrahydro-2H-pyran-2-yl)methanone | 502 |

TABLE 4-continued

| Ex. No. | Structure | Chemical Name | [M + H]+ |
| --- | --- | --- | --- |
| 47 | 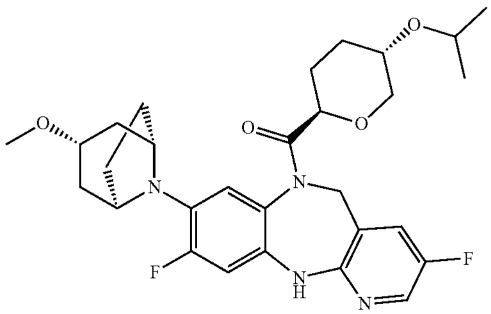 [SMILES: CO[C@H]1C[C@H]2CC[C@@H](C1)N2c1cc2c(cc1F)Nc1ncc(F)cc1CN2C(=O)[C@H]1CC[C@H](OC(C)C)CO1] | (3,9-difluoro-8-((1R,3S,5S)-3-methoxy-8-azabicyclo[3.2.1]octan-8-yl)-5,11-dihydro-6H-benzo[b]pyrido[2,3-e][1,4]diazepin-6-yl)((2R,5S)-5-isopropoxytetrahydro-2H-pyran-2-yl)methanone | 544 |
| 48 | 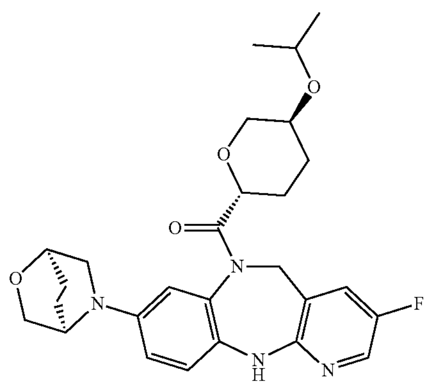 [SMILES: CC(C)O[C@H]1CC[C@H](C(=O)N2Cc3cc(F)cnc3Nc3ccc(N4C[C@H]5CC[C@@H]4CO5)cc32)OC1] | (8-((1R,4R)-2-oxa-5-azabicyclo[2.2.2]octan-5-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone | 498 |
| 49 | 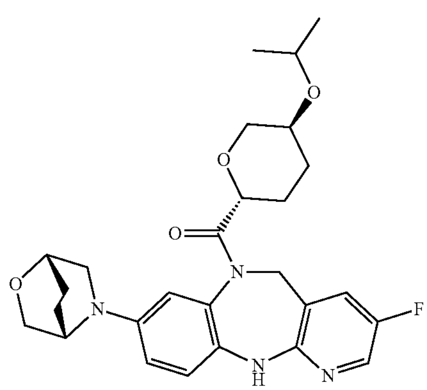 [SMILES: CC(C)O[C@H]1CC[C@H](C(=O)N2Cc3cc(F)cnc3Nc3ccc(N4C[C@@H]5CC[C@H]4CO5)cc32)OC1] | (8-((1S,4S)-2-oxa-5-azabicyclo[2.2.2]octan-5-yl)-3-fluoro-5,11-dihydro-6H-benzo[b]pyrido[2,3-e][1,4]diazepin-6-yl)((2R,5R)-5-isopropoxytetrahydro-2H-pyran-2-yl)methanone | 498 |

Example 50: (3,9-Difluoro-8-(1-methyl-1H-pyrazol-5-yl)-5,11-dihydro-6H-benzo[b]pyrido[2,3-e][1,4]diazepin-6-yl)(1-(2,2,2-trifluoroethyl)piperidin-4-yl)methanone

Example 52: (9-Fluoro-8-(1-methyl-1H-pyrazol-4-yl)-5,11-dihydro-6H-benzo[b]pyrido[2,3-e][1,4]diazepin-6-yl)(1-(2,2,2-trifluoroethyl)piperidin-4-yl)methanone

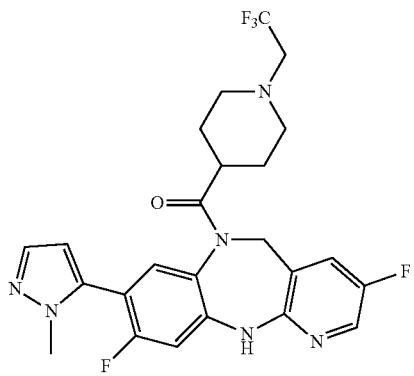 [SMILES: Cn1nccc1-c1cc2c(cc1F)Nc1ncc(F)cc1CN2C(=O)C1CCN(CC(F)(F)F)CC1]

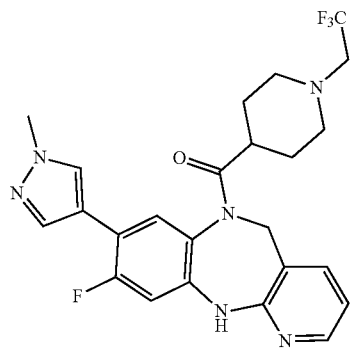 [SMILES: Cn1cc(-c2cc3c(cc2F)Nc2ncccc2CN3C(=O)C2CCN(CC(F)(F)F)CC2)cn1]

In a glovebox, 1-methyl-5-(4,4,5,5-tetramethyl-1,3,2-dioxaborolan-2-yl)-1H-pyrazole (16.9 mg, 0.081 mmol), 2nd generation Xphos Pd precatalyst (42.7 mg, 0.054 mmol), THF (1.0 mL) and potassium phosphate tribasic (0.5M, 0.340 mL) were added to the reaction vessel with (8-chloro-3,9-difluoro-5H-benzo[b]pyrido[2,3-e][1,4]diazepin-6(11H)-yl)(1-(2,2,2-trifluoroethyl)piperidin-4-yl)methanone (25 mg, 0.054 mmol). After heating at 40° C. for 16 h, the reaction mixture was cooled to ambient temperature and filtered. The solution was partionated between EtOAc and water, and the organic phase was separated, dried over Na₂SO₄, and solvent was removed under reduced pressure. The residue was purified by reverse phase HPLC (ACN/water with 0.05% TFA, gradient 10-45% in acetonitrile over 12 min) to afford (3,9-difluoro-8-(1-methyl-1H-pyrazol-5-yl)-5,11-dihydro-6H-benzo[b]pyrido[2,3e][1,4]diazepin-6-yl)(1-(2,2,2-trifluoroethyl)piperidin-4-yl)methanone as a solid. MS: 507 (M+H).

The compound in Table 5 was prepared using the methodology herein and the general procedure described in Example 50.

Step 1:

To a mixture of methanesulfonato(2-dicyclohexylphosphino-2',4'6'-tri-isopropyl-1,1'-biphenyl)(2'-amino-1,1'-biphenyl-2-yl)palladium(II) (11.69 mg, 0.014 mmol), 1-methyl-4-(4,4,5,5-tetramethyl-1,3,2-dioxaborolan-2-yl)-1H-pyrazole (38.3 mg, 0.184 mmol), and tert-butyl 8-chloro-9-fluoro-6-(1-(2,2,2-trifluoroethyl)piperidine-4-carbonyl)-5H-benzo[b]pyrido[2,3-e][1,4]diazepine-11(6H)-carboxylate (50 mg, 0.092 mmol) in a microwave vial was added dioxane (1.5 mL) followed by a solution of potassium phosphate tribasic (0.056 mL, 0.276 mmol) in water (0.5 mL). The reaction mixture was nitrogen/vacuum exchanged three times and it was allowed to stir at 100° C. for 1 h under microwave condition. LCMS showed clean reaction. The mixture was cooled and directly loaded on to ISCO column (40 g) eluting with EtOAc/hexane gradient (0-100%) to afford tert-butyl 9-fluoro-8-(1-methyl-1H-pyrazol-4-yl)-6-(1-(2,2,2-trifluoroethyl)piperidine-4-carbonyl)-5H-benzo[b]pyrido[2,3-e][1,4]diazepine-11(6H)-carboxylate as a syrup.

Step 2:

TFA (0.5 mL) was added to a stirred mixture of tert-butyl 9-fluoro-8-(1-methyl-1H-pyrazol-4-yl)-6-(1-(2,2,2-trifluoroethyl)piperidine-4-carbonyl)-5H-benzo[b]pyrido[2,3-e][1,4]diazepine-11(6H)-carboxylate (20 mg, 0.034 mmol) in DCM (1 mL) and the mixture was stirred at RT for 1 h. The

TABLE 5

| Ex. No. | Structure | Chemical Name | [M + H]+ |
| --- | --- | --- | --- |
| 51 |  | (3,9-difluoro-8-(1H-pyrazol-5-yl)-5,11-dihydro-6H-benzo[b]pyrido[2,3-e][1,4]diazepin-6-yl)(1-(2,2,2-trifluoroethyl)piperidin-4-yl)methanone | 493 | solvent was removed and the residue was taken up in DMSO (0.5 mL) and purified with reverse phase HPLC eluting with MeCN/0.1% TFA and water gradient (10-90%) to afford (9-fluoro-8-(1-methyl-1H-pyrazol-4-yl)-5H-benzo[b]pyrido[2,3-e][1,4]diazepin-6(11H)-yl)(1-(2,2,2-trifluoroethyl)piperidin-4-yl)methanone as a solid. MS: 489 (M+1).

The compound in Table 6 was prepared using the methodology herein and the general procedure described in Example 52.

TABLE 6

| Ex. No. | Structure | Chemical Name | [M + H]+ |
|---|---|---|---|
| 53 | 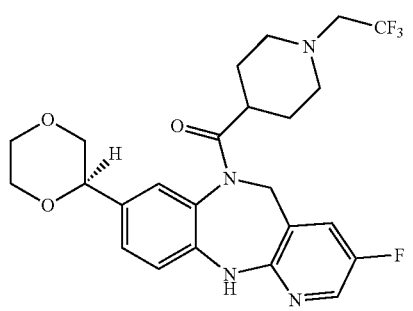 | (9-fluoro-8-(1-methyl-1H-pyrazol-5-yl)-5,11-dihydro-6H-benzo[b]pyrido[2,3-e][1,4]diazepin-6-yl)(1-(2,2,2-trifluoroethyl)piperidin-4-yl)methanone | 489 |

Examples 54 and 55: (S)-(8-(1,4-Dioxan-2-yl)-3-fluoro-5,11-dihydro-6H-benzo[b]pyrido[2,3-e][1,4]diazepin-6-yl)(1-(2,2,2-trifluoroethyl)piperidin-4-yl)methanone and (R)-(8-(1,4-dioxan-2-yl)-3-fluoro-5,11-dihydro-6H-benzo[b]pyrido[2,3-e][1,4]diazepin-6-yl)(1-(2,2,2-trifluoroethyl)piperidin-4-yl)methanone

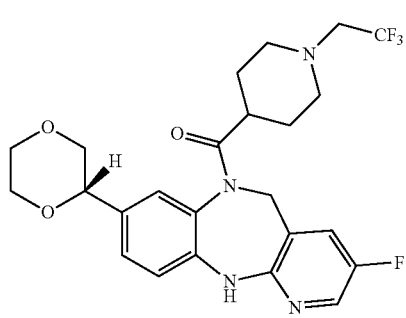

(Ex. 54)

(Ex. 55)

Step 1:
To a microwave vial equipped with a stir bar was added tert-butyl 8-chloro-3-fluoro-5H-benzo[b]pyrido[2,3-e][1,4]diazepine-11(6H)-carboxylate (300 mg, 0.858 mmol), 2-(5,6-dihydro-1,4-dioxin-2-yl)-4,4,5,5-tetramethyl-1,3,2-dioxaborolane (364 mg, 1.715 mmol), potassium phosphate, tribasic (8.58 mL, 0.5 M, 4.29 mmol) and THF (7.5 mL). The X-Phos G3 Pd precatalyst (72.6 mg, 0.086 mmol) was added last and the vial was sealed. The reaction mixture was degassed by bubbling nitrogen gas for 10 min. The reaction was microwave heated to 100° C. for 45 min. Upon cooling, the mixture was diluted with water, extracted with EtOAc, washed with brine, dried over sodium sulfate, filtered and concentrated. The residue was purified by column chromatography (eluent 0-60% EtOAc in hexane) to afford tert-butyl 8-(5,6-dihydro-1,4-dioxin-2-yl)-3-fluoro-5,6-dihydro-11H-benzo[b]pyrido[2,3-e][1,4]diazepine-11-carboxylate as a solid.

Step 2:
Under nitrogen gas flow, palladium on carbon (83 mg, 0.078 mmol) was added to the solid of tert-butyl 8-(5,6-dihydro-1,4-dioxin-2-yl)-3-fluoro-5,6-dihydro-11H-benzo[b]pyrido[2,3-e][1,4]diazepine-11-carboxylate (310 mg, 0.776 mmol), followed by addition of MeOH (15 mL). The reaction mixture was N₂/vacuum exchanged and then H₂/vacuum exchanged three times each. The reaction mixture was stirred with hydrogen balloon at RT for 16 h. The reaction was filtered over celite, washed with MeOH and concentrated to afford tert-butyl 8-(1,4-dioxan-2-yl)-3-fluoro-5,6-dihydro-11H-benzo[b]pyrido[2,3-e][1,4]diazepine-11-carboxylate.

Step 3:
To a stirred solution of 1-(2,2,2-trifluoroethyl)piperidine-4-carboxylic acid (171 mg, 0.808 mmol) in DCM (1.5 mL) and one drop DMF was added oxalyl chloride (77 μl, 0.882 mmol) at RT. The reaction was stirred at RT for 1.5 h and then concentrated to dryness. The resulting acyl chloride was redissolved in DCE (1.5 mL) and added to a hot suspension of tert-butyl 8-(1,4-dioxan-2-yl)-3-fluoro-5,6-dihydro-11H-benzo[b]pyrido[2,3-e][1,4]diazepine-11-carboxylate (295 mg, 0.735 mmol) in DCE (3 mL) at 80° C. DMAP (4.5 mg) in DCE (0.5 mL) was added subsequently. The mixture was heated overnight. Upon cooling to RT, the mixture was diluted with water, extracted with EtOAc (2×) and the combined organic layers were washed with brine, dried over sodium sulfate, filtered, and concentrated under reduced pressure. The residue was purified by column chromatography (40 g silica gel, EtOAc:EtOH (3:1) in hexanes 0-40%) to give roughly pure product, which was further purified by Gilson reverse phase HPLC (10-60% ACN/H2O with TFA modifier). The desired fractions were combined, concentrated to remove organic solvent, and the aqueous leftover was quenched with saturated NaHCO₃ solution, extracted with EtOAc (3×). The combined organic layers were washed with brine, dried over sodium sulfate, filtered, concentrated and dried to afford (8-(1,4-dioxan-2-yl)-3-fluoro-5,11-dihydro-6H-benzo[b]pyrido[2,3-e][1,4]diazepin-6-yl)(1-(2,2,2-trifluoroethyl)piperidin-4-yl)methanone as a racemic mixture. Chiral resolution with Chiralcel OZ-H column and 1:1 MeOH/acetonitrile co-solvent afforded both enantiomers as follows:

Peak 1: MS: 495 (M+1). $^1$H NMR (500 MHz, Methanol-$d_4$) δ 7.95 (d, J=2.8 Hz, 1H), 7.39 (dd, J=8.2, 2.9 Hz, 1H), 7.31-7.24 (m, 2H), 7.19 (dd, J=8.3, 4.5 Hz, 1H), 5.30 (dd, J=15.1, 2.4 Hz, 1H), 4.60 (ddd, J=9.7, 6.3, 2.7 Hz, 1H), 3.99 (dd, J=15.0, 5.9 Hz, 1H), 3.95-3.75 (m, 4H), 3.70 (td, J=11.2, 3.4 Hz, 1H), 3.42 (ddd, J=12.9, 11.6, 10.1 Hz, 1H), 3.03-2.87 (m, 3H), 2.79-2.69 (m, 1H), 2.51 (dtd, J=11.3, 7.2, 3.5 Hz, 1H), 2.28-2.17 (m, 1H), 1.97 (tt, J=11.9, 3.2 Hz, 1H), 1.91-1.76 (m, 2H), 1.39 (qt, J=12.2, 3.8 Hz, 1H), 1.20 (ddd, J=13.3, 6.2, 2.9 Hz, 1H).

Peak 2: MS: 495 (M+1). $^1$H NMR (500 MHz, Methanol-$d_4$) δ 7.94 (d, J=2.8 Hz, 1H), 7.38 (dd, J=8.2, 2.8 Hz, 1H), 7.32-7.23 (m, 2H), 7.18 (dd, J=8.3, 4.3 Hz, 1H), 5.30 (dd, J=15.1, 2.9 Hz, 1H), 4.60 (ddd, J=9.7, 6.3, 2.7 Hz, 1H), 3.98 (dd, J=15.0, 6.8 Hz, 1H), 3.94-3.74 (m, 4H), 3.74-3.65 (m, 1H), 3.42 (ddd, J=13.2, 11.6, 10.0 Hz, 1H), 3.03-2.87 (m, 3H), 2.75 (dt, J=11.8, 4.0 Hz, 1H), 2.50 (dtt, J=11.1, 7.3, 3.6 Hz, 1H), 2.22 (qd, J=11.8, 3.0 Hz, 1H), 1.97 (tt, J=11.9, 3.2 Hz, 1H), 1.90-1.77 (m, 2H), 1.39 (qt, J=12.2, 3.8 Hz, 1H), 1.20 (dd, J=9.8, 6.0 Hz, 1H).

Examples 56 and 57: (R)-(8-(1,4-Dioxan-2-yl)-9-fluoro-5,11-dihydro-6H-benzo[b]pyrido[2,3-e][1,4]diazepin-6-yl)(1-(2,2,2-trifluoroethyl)piperidin-4-yl)methanone and (S)-(8-(1,4-dioxan-2-yl)-9-fluoro-5,11-dihydro-6H-benzo[b]pyrido[2,3-e][1,4]diazepin-6-yl)(1-(2,2,2-trifluoroethyl)piperidin-4-yl)methanone

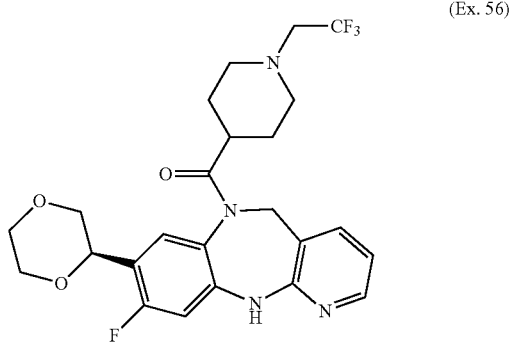
(Ex. 56)

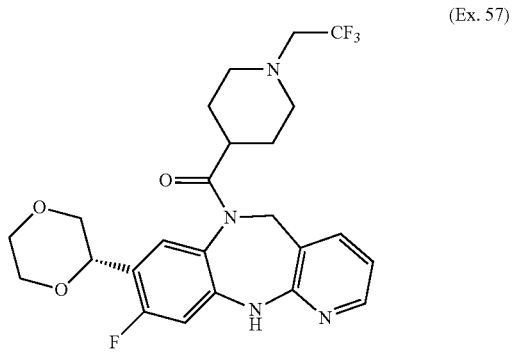
(Ex. 57)

Step 1:

To chloro[(di-(1-adamantyl)-N-butylphosphine)-2-(2-aminobiphenyl)]palladium(II) (70.9 mg, 0.106 mmol), 2-(5,6-dihydro-1,4-dioxin-2-yl)-4,4,5,5-tetramethyl-1,3,2-dioxaborolane (225 mg, 1.061 mmol), and tert-butyl 8-chloro-9-fluoro-6-(1-(2,2,2-trifluoroethyl)piperidine-4-carbonyl)-5H-benzo[b]pyrido[2,3-e][1,4]diazepine-11(6H)-carboxylate (288 mg, 0.530 mmol) in a microwave vial under nitrogen was added dioxane (3 mL) followed by a solution of potassium phosphate tribasic (0.27 mL, 1.326 mmol) in water (1.0 mL). The reaction mixture was $N_2$/vacuum exchanged for 3 times before it was allowed to stir at 100° C. for 1 h under microwave condition. LCMS showed the formation of the desired product. The mixture was directly loaded on ISCO column (40 g silica gel, eluting with EtOAc/hexane gradient (0-100%)) to afford a mixture of products. This mixture was purified with reverse phase HPLC eluting with MeCN/0.1% TFA and water gradient (10-90%) to afford tert-butyl 8-(5,6-dihydro-1,4-dioxin-2-yl)-9-fluoro-6-(1-(2,2,2-trifluoroethyl)piperidine-4-carbonyl)-5H-benzo[b]pyrido[2,3-e][1,4]diazepine-11(6H)-carboxylate as a foam. MS: 593 (M+1).

Step 2:

Tert-butyl 8-(5,6-dihydro-1,4-dioxin-2-yl)-9-fluoro-6-(1-(2,2,2-trifluoroethyl)piperidine-4-carbonyl)-5H-benzo[b]pyrido[2,3-e][1,4]diazepine-11(6H)-carboxylate (15 mg, 0.025 mmol) was dissolved in MeOH (2 mL). Pd—C (10 wt %, 3 mg, 2.82 μmol) was added and the reaction mixture was degassed and refilled with hydrogen in a balloon. The mixture was stirred at RT overnight. The mixture was filtered through a short celite pad, washed with EtOAc, and concentrated. The residue was used directly in the next step. MS: 595 (M+1).

Step 3:

TFA (0.5 mL) was added to a stirred mixture of tert-butyl 8-(1,4-dioxan-2-yl)-9-fluoro-6-(1-(2,2,2-trifluoroethyl)piperidine-4-carbonyl)-5H-benzo[b]pyrido[2,3-e][1,4]diazepine-11(6H)-carboxylate (15 mg, 0.025 mmol) in DCM (1 mL) and the mixture was stirred at RT for 1 h. LCMS showed clean reaction. The solvent was removed and the residue was purified with chiral SFC to afford (R)-(8-(1,4-dioxan-2-yl)-9-fluoro-5H-benzo[b]pyrido[2,3-e][1,4]diazepin-6(11H)-yl)(1-(2,2,2-trifluoroethyl)piperidin-4-yl)methanone (MS: 495 (M+1)) and (S)-(8-(1,4-dioxan-2-yl)-9-fluoro-5H-benzo[b]pyrido[2,3-e][1,4]diazepin-6(11H)-yl)(1-(2,2,2-trifluoroethyl)piperidin-4-yl)methanone as a solid. MS: 495 (M+1).

Examples 58 and 59: (Trans-4-isopropoxycyclohexyl) 9-methyl-8-[(1S,4S)-2-oxa-5-azabicyclo[2.2.2]oct-5-yl]-5,11-dihydro-6H-pyrido[2,3-b][1,5]benzodiazepin-6-yl]methanone and (trans-4-isopropoxycyclohexyl){7-methyl-8-[(1S,4S)-2-oxa-5-azabicyclo[2.2.2]oct-5-yl]-5,11-dihydro-6H-pyrido[2,3-b][1,5]benzodiazepin-6-yl}methanone

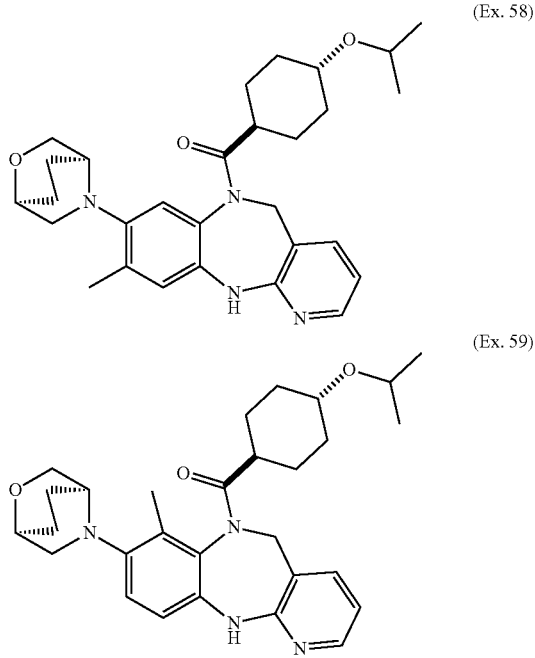

(Ex. 58)

(Ex. 59)

Inside a glovebox at 25° C., a mixture of tert-butyl peroxyacetate (27.7 mg, 0.210 mmol) in acetonitrile (0.42 mL) was added to an oven-dried vial containing a mixture of (trans-4-isopropoxycyclohexyl){8-[(1S,4S)-2-oxa-5-azabicyclo[2.2.2]oct-5-yl]-5,11-dihydro-6H-pyrido[2,3-b][1,5]benzodiazepin-6-yl}methanone (40 mg, 0.084 mmol) in acetonitrile (0.42 mL). TFA (64.7 µl, 0.839 mmol) was added. The reaction was transferred out of the glovebox and stirred under an LED light for 4 h. Upon cooling, the mixture was diluted with 10 mL of EtOAc, washed with sat. aqueous sodium hydrogen carbonate (3×5 mL), brine (5 mL), dried over $Na_2SO_4$, filtered and the mixture was evaporated under reduced pressure. The residue was purified by mass triggered reverse phase HPLC (ACN/water) to afford (trans-4-isopropoxycyclohexyl){9-methyl-8-[(1S,4S)-2-oxa-5-azabicyclo[2.2.2]oct-5-yl]-5,11-dihydro-6H-pyrido[2,3-b][1,5]benzodiazepin-6-yl}methanone and (trans-4-isopropoxycyclohexyl){7-methyl-8-[(1S,4S)-2-oxa-5-azabicyclo[2.2.2]oct-5-yl]-5,11-dihydro-6H-pyrido[2,3-b][1,5]benzodiazepin-6-yl}methanone. MS: 491 (M+1).

The compounds in Table 7 were prepared using the methodology herein and the general procedure described in Examples 58 and 59.

TABLE 7

| Ex. No. | Structure | Chemical Name | [M + H]+ |
|---|---|---|---|
| 60 | 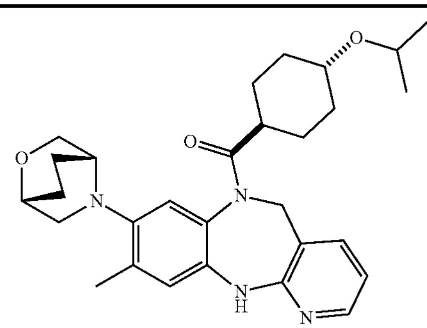 | (trans-4-isopropoxycyclohexyl){9-methyl-8-[(1R,4R)-2-oxa-5-azabicyclo[2.2.2]oct-5-yl]-5,11-dihydro-6H-pyrido[2,3-b][1,5]benzodiazepin-6-yl}methanone | 491 |
| 61 | 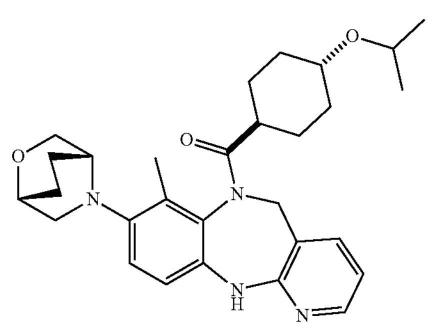 | (trans-4-isopropoxycyclohexyl){7-methyl-8-[(1R,4R)-2-oxa-5-azabicyclo[2.2.2]oct-5-yl]-5,11-dihydro-6H-pyrido[2,3-b][1,5]benzodiazepin-6-yl}methanone | 491 |

Examples 62 and 63: [9-fluoro-8-(2-oxa-5-azabicyclo[2.2.2]oct-5-yl)-5,11-dihydro-6H-pyrido[2,3-b][1,5]benzodiazepin-6-yl](trans-4-isopropoxycyclohexyl)methanone and [7-fluoro-8-(2-oxa-5-azabicyclo[2.2.2]oct-5-yl)-5,11-dihydro-6H-pyrido[2,3-b][1,5]benzodiazepin-6-yl](trans-4-isopropoxycyclohexyl)methanone (Ex. 62)

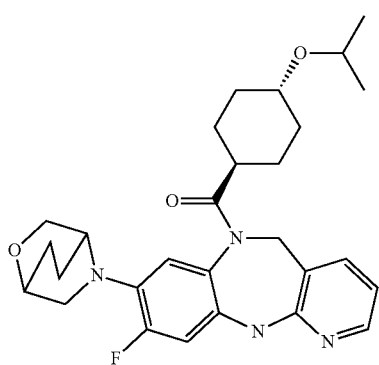

(Ex. 63)

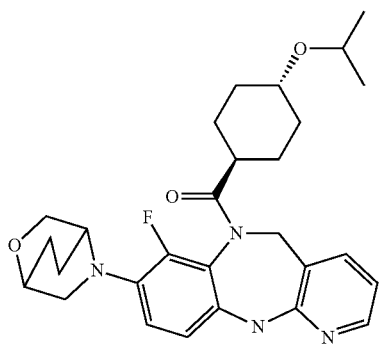

To a mixture of (trans-4-isopropoxycyclohexyl)[8-(2-oxa-5-azabicyclo[2.2.2]oct-5-yl)-5,11-dihydro-6H-pyrido[2,3-b][1,5]benzodiazepin-6-yl]methanone (200 mg, 0.420 mmol) in DMA (1 mL)/MeOH (1.0 mL) was added selectfluor (171 mg, 0.483 mmol) and the mixture was allowed to stir at RT for 1 h. The mixture was purified via reverse-phase chromatography to provide a single peak as a mixture of products. The mixture was purified via achiral SFC (ES, Ethyl Pyridine II, 21×250 (mm)) to afford [9-fluoro-8-(2-oxa-5-azabicyclo[2.2.2]oct-5-yl)-5,11-dihydro-6H-pyrido[2,3-b][1,5]benzodiazepin-6-yl](trans-4-isopropoxycyclohexyl)methanone (Peak 1 SFC), MS 495 (M+H), and [7-fluoro-8-(2-oxa-5-azabicyclo[2.2.2]oct-5-yl)-5,11-dihydro-6H-pyrido[2,3-b][1,5]benzodiazepin-6-yl](trans-4-isopropoxycyclohexyl)methanone (Peak 2 SFC), MS 495 (M+H).

Example 64: (8-((1S,4S)-2-Oxa-5-azabicyclo[2.2.1]heptan-5-yl)-9-fluoro-5H-benzo[b]pyrido[2,3-e][1,4]diazepin-6(11H)-yl)((2R,5S)-5-isopropoxytetrahydro-2H-pyran-2-yl)methanone

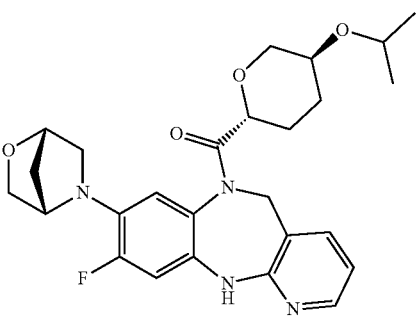 [SMILES: CC(C)O[C@H]1CC[C@H](C(=O)N2Cc3cccnc3Nc3cc(F)c(N4C[C@@H]5C[C@H]4CO5)cc32)OC1]

Step 1:

To an oven-dried, $N_2$(g) cooled 20 mL microwave vial was added di-tert-butyl 8-chloro-9-fluoro-5H-benzo[b]pyrido[2,3-e][1,4]diazepine-6,11-dicarboxylate (237 mg, 0.527 mmol), chloro(2-dicyclohexylphosphino-2',6'-di-isopropoxy-1,1'-biphenyl)[2-(2-aminoethylphenyl)]palladium (II), methyl-t-butylether adduct (43.0 mg, 0.053 mmol), and (1S,4S)-2-oxa-5-azabicyclo[2.2.1]heptane, HCl (107 mg, 0.790 mmol). Sodium tert-butoxide (506 mg, 5.27 mmol) was added and the vial was evacuated and filled with $N_2$(g). THF (10 mL) was added, the vial was sealed and the reaction mixture was heated to 80° C. overnight. Upon cooling to room temperature, trifluoroacetic acid (0.807 mL, 10.5 mmol) was added. After 1 hour, saturated aqueous sodium hydrogen carbonate (50 mL) was added and the mixture was extracted with EtOAc (3×30 mL). The combined organic fractions were washed with brine (30 mL), dried over $Na_2SO_4$, filtered and the mixture was evaporated under reduced pressure. The residue was purified by column chromatography on silica gel (ISCO 24 g, eluting with 0-30% ethyl acetate gradient in isohexane) to afford tert-butyl 8-((1S,4S)-2-oxa-5-azabicyclo[2.2.1]heptan-5-yl)-9-fluoro-5H-benzo[b]pyrido[2,3-e][1,4]diazepine-11(6H)-carboxylate as a foam.

Step 2:

To a mixture of tert-butyl 8-41S,4S)-2-oxa-5-azabicyclo[2.2.1]heptan-5-yl)-9-fluoro-5H-benzo[b]pyrido[2,3-e][1,4]diazepine-11(6H)-carboxylate (146 mg, 0.354 mmol) in DCM (1.42 mL) was added hydrochloric acid (4 M in water, 1.77 mL, 7.08 mmol). After 2 hours, the volatiles were evaporated under reduced pressure to afford (1S,4S)-5-(9-fluoro-6,11-dihydro-5H-benzo[b]pyrido[2,3-e][1,4]diazepin-8-yl)-2-oxa-5-azabicyclo[2.2.1]heptane as the HCl salt.

Step 3:

To a mixture of (2R,5S)-5-isopropoxytetrahydro-2H-pyran-2-carboxylic acid (16 mg, 0.083 mmol), (1S,4S)-5-(9-fluoro-6,11-dihydro-5H-benzo[b]pyrido[2,3-e][1,4]diazepin-8-yl)-2-oxa-5-azabicyclo[2.2.1]heptane (26 mg, 0.083 mmol), PS-PPh3 (2.06 mmol/g loading, 121 mg, 0.250 mmol), and trichloroacetonitrile (42 µl, 0.416 mmol) in a microwave vial was added acetonitrile (832 µl). The mixture was heated under microwave irradiation to 100° C. for 10 min. Upon cooling to room temperature, the mixture was filtered through a syringe filter disk and the filtrate was purified by preparative HPLC to afford (8-((1S,4S)-2-Oxa-5-azabicyclo[2.2.1]heptan-5-yl)-9-fluoro-5H-benzo[b]

pyrido[2,3-e][1,4]diazepin-6(11H)-yl)((2R,5S)-5-iso-propoxytetrahydro-2H-pyran-2-yl)methanone as a gum. MS: 483 (M+1). ¹H NMR (500 MHz, Methanol-d₄) δ 8.07-7.94 (m, 2H), 7.13 (td, J=11.9, 10.7, 2.0 Hz, 1H), 7.04 (ddd, J=7.0, 5.9, 4.2 Hz, 1H), 6.93 (d, J=8.5 Hz, 1H), 5.41 (dd, J=21.7, 15.1 Hz, 1H), 4.72-4.48 (m, 2H), 4.21-4.04 (m, 2H), 4.04-3.82 (m, 3H), 3.78-3.60 (m, 3H), 3.41 (td, J=10.5, 10.0, 4.9 Hz, 1H), 3.22 (ddd, J=35.1, 10.1, 3.1 Hz, 1H), 3.03-2.93 (m, 1H), 2.74-2.62 (m, 1H), 2.17-1.92 (m, 3H), 1.54 (tdd, J=13.2, 11.1, 3.8 Hz, 1H), 1.46-1.34 (m, 1H), 1.21-0.98 (m, 6H).

Example 65: (8-Chloro-5-methyl-5,11-dihydro-6H-benzo[b]pyrido[2,3-e][1,4]diazepin-6-yl)(trans-4-isopropoxycyclohexyl)methanone

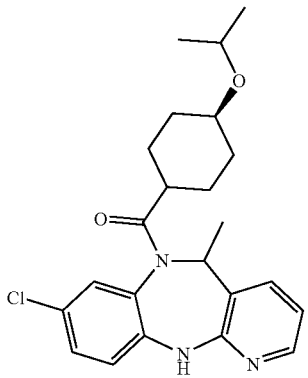

Step 1:
To a solution of 4-chloro-2-nitroaniline (474 mg, 2.75 mmol), 1-(2-bromopyridin-3-yl)ethanone (500 mg, 2.500 mmol), Pd₂(dba)₂ (114 mg, 0.125 mmol), (9,9-dimethyl-9H-xanthene-4,5-diyl)bis(diphenylphosphine) (Xantphos) (217 mg, 0.375 mmol), cesium carbonate (3.2 g, 10.00 mmol) in 1,4-dioxane (10 mL) was degassed by bubbling nitrogen through the reaction mixture. The mixture was heated to reflux and left overnight and then cooled to RT. Boc₂O (818 mg, 3.75 mmol) and DMAP (458 mg, 3.75 mmol) were added and stirred for 3-4 h. When the reaction was complete, it was diluted with dichloromethane and filtered through a pad of celite, washed three times with dichloromethane, and the solvent removed to afford crude tert-butyl (3-acetylpyridin-2-yl)(4-chloro-2-nitrophenyl)carbamate as a solid which was used in the next step without further purification. MS: 392 (M+1).
Step 2:
Under nitrogen gas flow, 3% Pt-0.6% V/C (299 mg) was added to tert-butyl (3-acetylpyridin-2-yl)(4-chloro-2-nitrophenyl)carbamate (600 mg, 1.531 mmol), followed by addition of methanol (20 mL) and ethyl acetate (10 mL). The reaction mixture was degassed with nitrogen and then stirred under hydrogen at RT overnight. The reaction mixture was diluted with dichloromethane and filtered over celite, washed with dichloromethane, concentrated and absorbed on silica gel and purified by ISCO chromatography (40 g column, 0-100% Hexane-Ethylacetate) to afford tert-butyl (3-acetylpyridin-2-yl)(2-amino-4-chlorophenyl)carbamate as a solid. MS: 362 (M+1).
Step 3:
To a solution of tert-butyl (3-acetylpyridin-2-yl)(2-amino-4-chlorophenyl)carbamate (300 mg, 0.829 mmol) in 1,2-dichloroethane (5 mL) was added sodiumtriacetoxyborohydride (527 mg, 2.487 mmol) and heated at 80° C. for 4 h. The reaction mixture was cooled to RT, taken into a separatory funnel, diluted with EtOAc, washed with water, brine and dried over anhydrous sodium sulfate. Filtration and removal of the solvent afforded the crude, which was purified by ISCO silica gel chromatography using hexane and EtOAc (0-100%) to afford tert-butyl 8-chloro-5-methyl-5,6-dihydro-11H-benzo[b]pyrido[2,3-e][1,4]diazepine-11-carboxylate as an oil. MS: 246 (M-ᵗBu).
Step 4:
To a solution of trans-4-isopropoxycyclohexanecarboxylic acid (118 mg, 0.636 mmol) in dichloromethane (3 mL) was added oxalyl chloride (0.101 mL, 1.157 mmol), followed by a drop of DMF and stirred for 1 h at RT. The reaction mixture was concentrated to dryness and vacuum was applied for 5 min to remove any residual oxalyl chloride. The residue was dissolved in 1,2-dichloroethane (3.0 mL) and tert-butyl 8-chloro-5-methyl-5H-benzo[b]pyrido[2,3-e][1,4]diazepine-11(6H)-carboxylate (200 mg, 0.578 mmol) was added followed by N,N-dimethylpyridin-4-amine (3.53 mg, 0.029 mmol) and stirred at 80° C. overnight. The reaction mixture was stirred for 24 h, poured into a separatory funnel, washed with water, saturated sodium bicarbonate solution, brine, dried over anhydrous sodium sulfate, filtered and the solvent removed to give crude mixture which was taken in dichloromethane (1 mL) and treated with trifluoroacetic acid (1 mL) and stirred at RT for 1 h. Removal of the solvent afforded the crude product, which was purified by Gilson reverse phase HPLC using acetonitrile and water both containing 0.05% TFA to afford (8-chloro-5-methyl-5,11-dihydro-6H-benzo[b]pyrido[2,3-e][1,4]diazepin-6-yl)(trans-4-isopropoxycyclohexyl)methanone as a solid. MS: 414 (M+1).

Example 66: (Trans-4-isopropoxycyclohexyl)(5-methyl-8-morpholino-5,11-dihydro-6H-benzo[b]pyrido[2,3-e][1,4]diazepin-6-yl)methanone

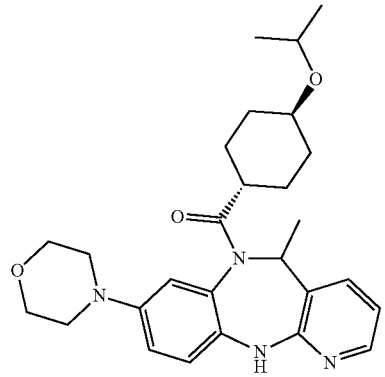 [SMILES: CC(C)O[C@H]1CC[C@H](C(=O)N2c3cc(N4CCOCC4)ccc3Nc3ncccc3C2C)CC1]

To a microwave vial was added (8-chloro-5-methyl-5H-benzo[b]pyrido[2,3-e][1,4]diazepin-6(11H)-yl)(trans-4-isopropoxycyclohexyl)methanone (13 mg, 0.031 mmol), chloro(2-dicyclohexylphosphino-2',6'-di-i-propoxy-1,1'-biphenyl)[2-(2-aminoethylphenyl)]palladium(II), methyl-t-butylether adduct (1.3 mg, 1.570 μmol) and 2-di-cyclohexylphosphino-2',6'-di-i-propoxy-1,1'-biphenyl (0.7 mg, 1.570 μmol). The vial was evacuated and refilled with N₂ gas. Lithium bis(trimethylsilyl)amide (0.19 mL, 0.188 mmol) in tetrahydrofuran was added via a syringe, followed by morpholine (3.3 mg, 0.038 mmol). The vial was sealed and the reaction mixture was heated to 80° C. overnight. Another batch of all the reagents was added and heating continued for one more day. Reaction mixture was cooled to RT, diluted with ethylacetate, and solvents were removed under reduced pressure. The residue was redissolved in DMF (2 mL) and purified by Gilson reverse phase HPLC using acetonitrile and water (both containing 0.05% TFA) to afford (trans-4-isopropoxycyclohexyl)(5-methyl-8-morpholino-5,11-dihydro-6H-benzo[b]pyrido[2,3-e][1,4]diazepin-6-yl)methanone as a solid. MS: 465 (M+1).

Example 67: (8-Methoxy-5-methyl-5,11-dihydro-6H-benzo[b]pyrido[2,3-e][1,4]diazepin-6-yl)(1-(2,2,2-trifluoroethyl)piperidin-4-yl)methanone

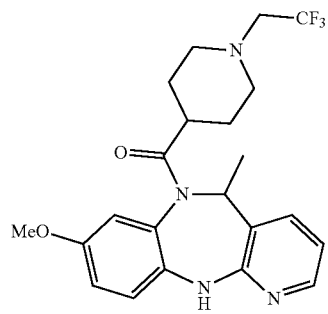 [SMILES: COc1ccc2c(c1)N(C(=O)C1CCN(CC(F)(F)F)CC1)C(C)c1cccnc1N2]

Step 1:
A mixture of 4-methoxybenzene-1,2-diamine (2.0 g, 14.48 mmol) and 1-(2-fluoropyridin-3-yl)ethanone (2.01 g, 14.48 mmol) in dioxane (20 mL) was heated at 100° C. overnight. The reaction mixture was cooled to RT. The solvent was removed under reduced pressure, and the crude was purified by ISCO silica gel chromatography using hexane and ethyl acetate (0-100%) to afford 1-(2-((2-amino-4-methoxyphenyl)amino)pyridin-3-yl)ethan-1-one as an oil. MS: 258 (M+1).
Step 2:
To a solution of 1-(2-((2-amino-4-methoxyphenyl)amino)pyridin-3-yl)ethanone (910 mg, 3.54 mmol) in 1,2-dichloroethane (20 mL) was added sodium triacetoxyborohydride (2.25 g, 10.61 mmol) and heated at 80° C. for 4 h. The reaction mixture was cooled to RT and taken into a separatory funnel, diluted with ethylacetate, washed with water, sodium bicarbonate saturated solution, water and brine. Removal of the solvent afforded the crude, which was purified by ISCO silica gel chromatography using hexane/ethyl acetate (0-100%) to afford 8-methoxy-5-methyl-6,11-dihydro-5H-benzo[b]pyrido[2,3-e][1,4]diazepine as a solid. MS: 242 (M+1).
Step 3:
To a solution of 1-(2,2,2-trifluoroethyl)piperidine-4-carboxylic acid (96 mg, 0.456 mmol) in dichloromethane (3 mL) was added oxalyl chloride (0.073 mL, 0.829 mmol) followed by a drop of DMF and stirred for 1 h at RT. The reaction mixture was concentrated to dryness and vacuum was applied for 5 min to remove any residual oxalyl chloride. The residue was redissolved in 1,2-dichloroethane (3.00 mL) and 8-methoxy-5-methyl-6,11-dihydro-5H-benzo[b]pyrido[2,3-e][1,4]diazepine (100 mg, 0.414 mmol) was added followed by N,N-dimethylpyridin-4-amine (2.5 mg, 0.021 mmol) and stirred at 80° C. overnight. The reaction mixture was poured into a separatory funnel, washed with water, saturated sodium bicarbonate solution, brine, dried over anhydrous sodium sulfate, filtered and the solvent removed to afford the crude which was purified by Gilson reverse phase HPLC using acetonitrile and water both containing 0.05% TFA to afford (8-methoxy-5-methyl-5,11-dihydro-6H-benzo[b]pyrido[2,3-e][1,4]diazepin-6-yl)(1-(2,2,2-trifluoroethyl)piperidin-4-yl)methanone. MS: 568 (M+1).

Example 68: (Trans-4-isopropoxycyclohexyl)(8-methoxy-5-methyl-5,11-dihydro-6H-benzo[b]pyrido[2,3-e][1,4]diazepin-6-yl)methanone

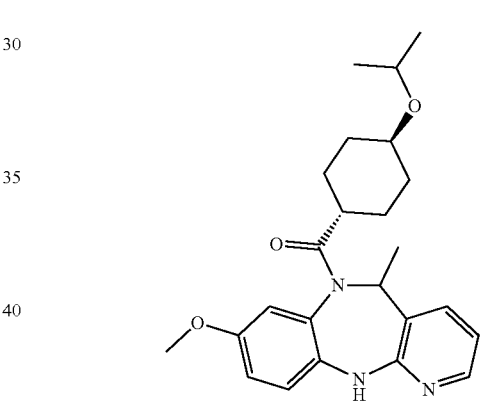

To a solution of trans-4-isopropoxycyclohexanecarboxylic acid (331 mg, 1.778 mmol) in DCM (5 mL) was added oxalyl dichloride (0.283 mL, 3.23 mmol) followed by a drop of DMF and stirred for 1 h at RT. The reaction mixture was concentrated to dryness and vacuum was applied for 5 min to remove any residual oxalyl chloride. The residue was redissolved in 1,2-dichloroethane (10 mL) and 8-methoxy-5-methyl-6,11-dihydro-5H-benzo[b]pyrido[2,3-e][1,4]diazepine (390 mg, 1.616 mmol) was added followed by N,N-dimethylpyridin-4-amine (9.87 mg, 0.081 mmol) and stirred at 80° C. for overnight. The reaction mixture was poured into a separatory funnel, washed with saturated sodium bicarbonate solution, water, brine, dried over anhydrous sodium sulfate, filtered and the solvent was removed to afford crude product which was purified by ISCO silica gel chromatography using hexane and ethyl acetate (40 g column, 0-100%) to afford (trans-4-isopropoxycyclohexyl)(8-methoxy-5-methyl-5,11-dihydro-6H-benzo[b]pyrido[2,3-e][1,4]diazepin-6-yl)methanone as a solid. MS: 410 (M+1).

Example 69: (8-((1S,4S)-2-Oxa-5-azabicyclo[2.2.2]
octan-5-yl)-3-methyl-5,11-dihydro-6H-benzo[b]
pyrido[2,3-e][1,4]diazepin-6-yl)(trans-4-isopropoxy-
cyclohexyl)methanone

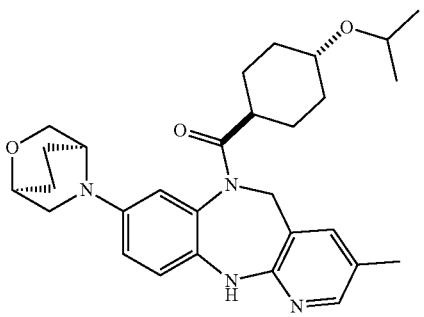

In glove box, potassium phosphate tribasic (74.7 µl, 0.075 mmol) was added to a stirred mixture of $2^{nd}$ generation Xphos Pd precatalyst (1.96 mg, 2.49 µmol), iodomethane (15.5 µl, 0.249 mmol) and (8-((1S,4S)-2-oxa-5-azabicyclo[2.2.2]octan-5-yl)-3-(4,4,5,5-tetramethyl-1,3,2-dioxaborolan-2-yl)-5,11-dihydro-6H-benzo[b]pyrido[2,3-e][1,4]diazepin-6-yl)(trans-4-isopropoxycyclohexyl)methanone (15 mg, 0.025 mmol) in THF (0.25 mL). The vial was sealed, and the reaction mixture was stirred at 70° C. overnight. The mixture was cooled, diluted with ethyl acetate (1 mL), washed with aqueous sodium hydrogen carbonate (saturated, 3×0.5 mL), dried over $Na_2SO_4$, filtered and the solvent was evaporated under reduced pressure. The residue was purified by reverse phase HPLC (ACN/water with 0.05% TFA, gradient 10-70% in acetonitrile over 15 min.) to afford (8-((1S,4S)-2-oxa-5-azabicyclo[2.2.2]octan-5-yl)-3-methyl-5,11-dihydro-6H-benzo[b]pyrido[2,3-e][1,4]diazepin-6-yl)(trans-4-isopropoxycyclohexyl)methanone as a solid. MS: 491 (M+H).

Example 70: (8-((1S,4S)-2-oxa-5-azabicyclo[2.2.2]
octan-5-yl)-3-(methylsulfonyl)-5,11-dihydro-6H-
benzo[b]pyrido[2,3-e][1,4]diazepin-6-yl)(trans-4-
isopropoxycyclohexyl)methanone

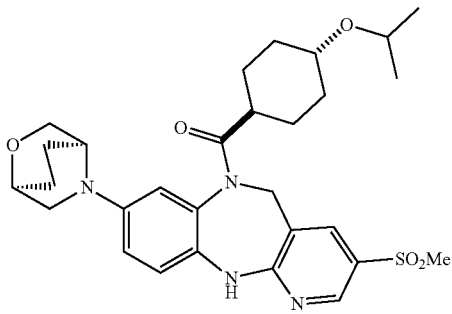

To a solution of (8-((1S,4S)-2-oxa-5-azabicyclo[2.2.2]octan-5-yl)-3-(4,4,5,5-tetramethyl-1,3,2-dioxaborolan-2-yl)-5,11-dihydro-6H-benzo[b]pyrido[2,3-e][1,4]diazepin-6-yl)(trans-4-isopropoxycyclohexyl)methanone (15 mg, 0.025 mmol) in DMF (0.25 mL) was added molecular sieves (30 mg), copper(II) acetate (5.0 mg, 0.027 mmol), potassium carbonate (7.0 mg, 0.050 mmol) and sodium methanesulfinate (3.8 mg, 0.037 mmol). The mixture was stirred at 70° C. for 2 h, cooled, diluted with ethyl acetate (2 mL), washed with water (1×1 mL), and the solvent was evaporated under reduced pressure. The residue was purified by reverse phase HPLC (ACN/water with 0.05% TFA, gradient 15-60% in acetonitrile over 15 min) to afford (8-((1S,4S)-2-oxa-5-azabicyclo[2.2.2]octan-5-yl)-3-(methylsulfonyl)-5,11-dihydro-6H-benzo[b]pyrido[2,3-e][1,4]diazepin-6-yl)(trans-4-isopropoxycyclohexyl)methanone. MS: 555 (M+H).

Example 71: (8-((1S,4S)-2-Oxa-5-azabicyclo[2.2.2]
octan-5-yl)-3-chloro-5,11-dihydro-6H-benzo[b]
pyrido[2,3-e][1,4]diazepin-6-yl)(trans-4-isopropoxy-
cyclohexyl)methanone

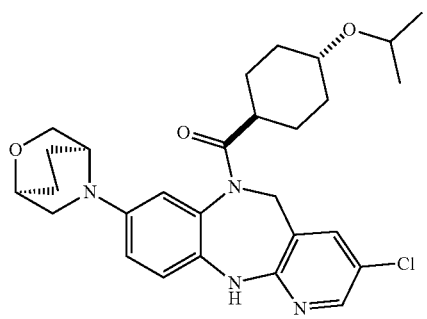

To the solution of (8-((1S,4S)-2-oxa-5-azabicyclo[2.2.2]octan-5-yl)-3-(4,4,5,5-tetramethyl-1,3,2-dioxaborolan-2-yl)-5,11-dihydro-6H-benzo[b]pyrido[2,3-e][1,4]diazepin-6-yl)(trans-4-isopropoxycyclohexyl)methanone (25 mg, 0.041 mmol) in MeOH (0.415 mL) was added a solution of copper (II) chloride (19.5 mg, 0.145 mmol) in water (0.415 mL), then the reaction mixture was stirred at RT overnight. The mixture was diluted with ethyl acetate (2 mL), washed with water (1×1 mL), dried over $Na_2SO_4$, filtered and the solvent was evaporated under reduced pressure. The residue was purified by reverse phase HPLC (ACN/water with 0.05% TFA, gradient 35-65% in acetonitrile over 12 min) to afford (8-((1S,4S)-2-oxa-5-azabicyclo[2.2.2]octan-5-yl)-3-chloro-5,11-dihydro-6H-benzo[b]pyrido[2,3-e][1,4]diazepin-6-yl)(trans-4-isopropoxycyclohexyl)methanone as a solid. MS: 511 (M+H).

Examples 72 and 73: (3,9-Difluoro-5,11-dihydro-6H-benzo[b]pyrido[2,3-e][1,4]diazepin-6-yl)(1-(2,2,2-trifluoroethyl)piperidin-4-yl)methanone and (8-(2-oxa-5-azabicyclo[2.2.2]octan-5-yl)-3,9-difluoro-5H-benzo[b]pyrido[2,3-e][1,4]diazepin-6(11H)-yl)(1-(2,2,2-trifluoroethyl)piperidin-4-yl)methanone (Ex. 72)

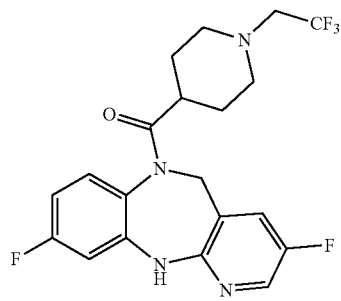

(Ex. 73)

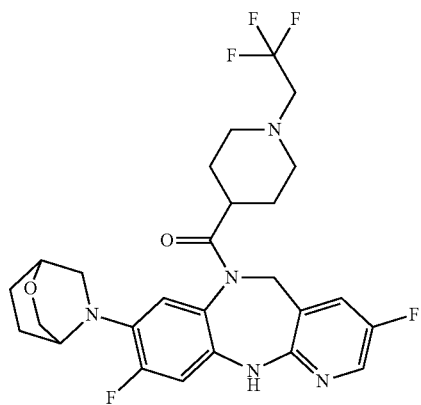

A mixture of (8-chloro-3,9-difluoro-5H-benzo[b]pyrido[2,3-e][1,4]diazepin-6(11H)-yl)(1-(2,2,2-trifluoroethyl)piperidin-4-yl)methanone (80 mg, 0.174 mmol), 2-oxa-5-azabicyclo[2.2.2]octane (67.6 mg, 0.347 mmol) and methanesulfonato(2-dicyclohexylphosphino-2',6'-di-i-propoxy-1,1'-biphenyl)(2'-amino-1,1'-biphenyl-2-yl)palladium(II) (RuPhos Palladacycle Gen. 3) (14.52 mg, 0.017 mmol) was vacuumed/N₂ exchanged three times, and lithium bis(trimethylsilyl)amide (1.0M in THF, 1.389 mL, 1.389 mmol) was added to the mixture. The reaction mixture was heated at 80° C. for 2 h. The reaction mixture was diluted with EtOAc and water. The aqueous was extracted with EtOAc, the combined organic layers were washed with brine, dried over Na₂SO₄, filtered and concentrated. The residue was separated by ISCO column (40 g gold, 0-80% EtOAc in hexane gradient) to afford (3,9-difluoro-5H-benzo[b]pyrido[2,3-e][1,4]diazepin-6(11H)-yl)(1-(2,2,2-trifluoroethyl)piperidin-4-yl)methanone (MS: 427 (M+1)) and (8-(2-oxa-5-azabicyclo[2.2.2]octan-5-yl)-3,9-difluoro-5H-benzo[b]pyrido[2,3-e][1,4]diazepin-6(11H)-yl)(1-(2,2,2-trifluoroethyl)piperidin-4-yl)methanone (MS: 538 (M+1)) as a foam (racemate).

Example 74: (9-Fluoro-5,11-dihydro-6H-benzo[b]pyrido[2,3-e][1,4]diazepin-6-yl)(1-(2,2,2-trifluoroethyl)piperidin-4-yl)methanone

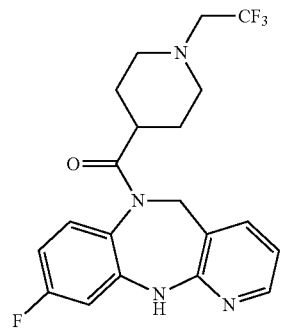 [SMILES: O=C(C1CCN(CC(F)(F)F)CC1)N1Cc2cccnc2Nc2cc(F)ccc21]

TFA (1 mL) was added to a stirred mixture of tert-butyl 9-fluoro-6-(1-(2,2,2-trifluoroethyl)piperidine-4-carbonyl)-5H-benzo[b]pyrido[2,3-e][1,4]diazepine-11(6H)-carboxylate (70 mg, 0.138 mmol) in DCM (2 mL) and the mixture was stirred at RT for 1 h. The solvent was removed, the residue was taken up in 0.5 mL DMSO and was purified by reverse phase HPLC eluting with MeCN/0.1% TFA and water gradient (10-90%) to afford (9-fluoro-5H-benzo[b]pyrido[2,3-e][1,4]diazepin-6(11H)-yl)(1-(2,2,2-trifluoroethyl)piperidin-4-yl)methanone as a solid. MS: 409 (M+1).

R132H IDH1 Enzymatic Assay

Each test compound (10 mM stock in DMSO) is diluted in DMSO to make a 10-point, 3-fold dilution series. 125 nL of each dilution or DMSO alone is dispensed to a 384-well Greiner Lumitrac 200 assay plate using an Echo® Liquid Handler. To each well of the plate is added 20 uL of enzyme in assay buffer or assay buffer alone. Assay buffer consists of 50 mM sodium phosphate, pH 7.0, 50 mM magnesium chloride, 50 mM sodium chloride, and 0.01% (w/v) bovine serum albumin. When present, the R132H mutant IDH1 enzyme is at a working concentration of 1.875 nM (final concentration in assay of 1.5 nM). The assay plate is allowed to incubate for 30 minutes at room temperature and 5 uL of 5× substrate mixture (2.5 uM nicotinamide adenine dinucleotide phosphate, 100 uM adenosine diphosphate, 7.5 mM glyceraldehyde-3-phosphate, 7.5 ug/mL of spinach glyceraldehyde-3-phosphate dehydrogenase, 25 nM phosphoglycerate kinase, and 5 mM alpha-ketoglutarate in assay buffer) is added to all wells. The reaction plate is incubated for 60 minutes followed by addition of 25 uL of Promega Kinase-GLO reagent to all wells and 10-minute incubation.

Luminescence is measured using a PerkinElmer Envision plate reader. The percent activity of each dilution is determined as the ratio of background corrected signal to the background corrected signal of wells receiving only DMSO. IC50 values are determined by fitting percent activity data to a four-parameter logistic dose response equation. The IC50 values of the exemplified compounds are included in Table 8.

TABLE 8

| IC50 values of the Exemplified Compounds | |
|---|---|
| Ex. No. | IC$_{50}$, nM |
| 1 | |
| 2 | |
| 3 | |

TABLE 8-continued

IC50 values of the Exemplified Compounds

| Ex. No. | IC$_{50}$, nM |
|---|---|
| 4 | |
| 5 | 11.3 |
| 6 | 12.1 |
| 7 | 18.5 |
| 8 | 25.4 |
| 9 | 21.7 |
| 10 | 6.2 |
| 11 | 23.8 |
| 12 | 22.1 |
| 13 | 35.5 |
| 14 | 44.3 |
| 15 | 83.4 |
| 16 | 24 |
| 17 | 28.4 |
| 18 | 8.6 |
| 19 | 6 |
| 20 | 6.7 |
| 21 | 4.5 |
| 22 | 4.2 |
| 23 | 23 |
| 24 | 5.6 |
| 25 | 7.8 |
| 26 | 13.8 |
| 27 | 27.5 |
| 28 | 27.6 |
| 29 | 9.9 |
| 30 | 14.1 |
| 31 | 18 |
| 32 | 18.1 |
| 33 | 21.82 |
| 34 | 23.45 |
| 35 | 28 |
| 36 | 23.7 |
| 37 | 36.9 |
| 38 | 36 |
| 39 | 10.4 |
| 40 | 25.5 |
| 41 | 21 |
| 42 | 13.6 |
| 43 | 87 |
| 44 | 11.4 |
| 45 | 18.3 |
| 46 | 17.9 |
| 47 | 15.8 |
| 48 | 10 |
| 49 | 12 |
| 50 | 3.5 |
| 51 | 3.6 |
| 52 | 5.7 |
| 53 | 7.2 |
| 54 | 5.6 |
| 55 | 6.5 |
| 56 | 18.1 |
| 57 | 12.2 |
| 58 | 18.3 |
| 59 | 58.7 |
| 60 | 25.9 |
| 61 | 54.1 |
| 62 | 35.2 |
| 63 | 57.0 |
| 64 | 46.3 |
| 65 | 105.6 |
| 66 | 71.9 |
| 67 | 214.6 |
| 68 | 112.2 |
| 69 | 102.6 |
| 70 | 5745 |
| 71 | 30 |
| 72 | 160 |
| 73 | 10 |
| 74 | 174 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

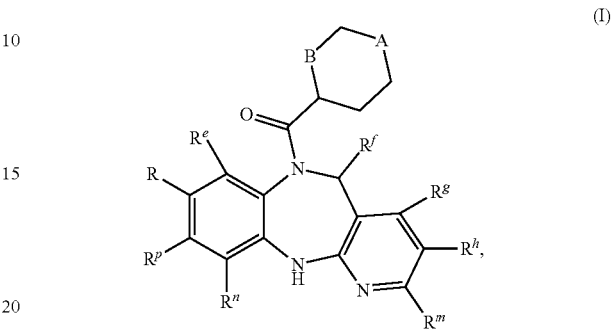

wherein:

A is —CH($R^1$)— or —N($R^2$)—; $R^1$ is selected from the group consisting of hydrogen, —O—$C_{1-10}$alkyl, and $C_{1-10}$alkyl optionally substituted with one to four halogens; and $R^2$ is selected from the group consisting of hydrogen, —S(O)$_2$—$C_{1-4}$alkyl, and $C_{1-10}$alkyl optionally substituted with one to four halogens;

B is —CH$_2$— or —O—;

R is selected from the group consisting of:
(1) hydrogen,
(2) halogen,
(3) —$C_{1-10}$alkyl,
(4) —O—$C_{1-10}$alkyl,
(5) —NR$^x$R$^y$, wherein each of R$^x$ and R$^y$ is independently selected from the group consisting of (a) hydrogen and (b) $C_{1-6}$alkyl optionally substituted with one to four substituents independently selected from halogen and heterocyclyl; wherein the heterocyclyl is optionally substituted with one to four substituents independently selected from methyl, ethyl, propyl, butyl, —CH$_2$—Cl, —CH$_2$—F, —CH$_2$CH$_2$—Cl, —CH$_2$CH$_2$—F, and —CH$_2$CF$_3$; and
(6) heterocyclyl, optionally substituted with one to four substituents independently selected from halogen, hydroxyl, —$C_{1-10}$alkyl, and —O—$C_{1-10}$alkyl;

R$^e$ is selected from the group consisting of:
(1) hydrogen,
(2) halogen, and
(3) $C_{1-6}$alkyl; and each of R$^f$, R$^g$, R$^h$, R$^m$, R$^n$ and R$^p$ is independently selected from the group consisting of:
(1) hydrogen,
(2) halogen,
(3) $C_{1-6}$alkyl, and
(4) —S(O)$_2$—$C_{1-4}$alkyl;

with the proviso that when R$^e$ is hydrogen, at least one of R$^f$, R$^g$, R$^h$, R$^m$, R$^n$ and R$^p$ is not hydrogen.

2. The compound of claim 1, or a pharmaceutically acceptable salt thereof, wherein each occurrence of a heterocyclyl is independently selected from the group consisting of 2-azabicyclo[2.2.2]octanyl, 8-azabicyclo[3.2.1]octanyl, 2-azaspiro[3.3]heptanyl, azaindolyl, 1,6-diazaspiro[3.3]heptanyl, 2,3-dihydro-1,4-dioxinyl, 1,4-dioxanyl, hexahydro-3,6-epiminofuro[3,2-b]furanyl, hexahydro-1H- furo[3,4-c]pyrrolyl, imidazolyl, isoxazolyl, morpholinyl, 2-oxa-5-azabicyclo[2.2.1]heptanyl, 6-oxa-3-azabicyclo[3.1.1]heptanyl, 6-oxa-2-azaspiro[3.5]nonanyl, 2-oxa-5-azabicyclo[2.2.2]octanyl, 3-oxa-8-azabicyclo[3.2.1]octanyl, 8-oxa-3-azabicyclo[3.2.1]octanyl, 1-oxa-8-azaspiro[4.5]decanyl, 6-oxa-2-azaspiro[3.4]octanyl, 3-oxa-1,7-diazaspiro[4.4]nonanyl, 3,9-dioxa-7-azabicyclo[3.3.1]nonanyl, oxazolidinyl, piperazinyl, piperidinyl, pyrazolyl, pyridazinyl, pyridinyl, pyrimidinyl, pyrrolidinyl, pyrrolyl, tetrahydrofuranyl and tetrahydropyranyl.

3. The compound of claim 1, or a pharmaceutically acceptable salt thereof, wherein:
A is —CH($R^1$)— or —N($R^2$)—; $R^1$ is selected from the group consisting of hydrogen, —$C_{1-6}$alkyl and —O—$C_{1-6}$alkyl; $R^2$ is selected from the group consisting of hydrogen, methyl, ethyl, propyl, butyl, —$CH_2CF_3$, and —$S(O)_2$—$C_{1-4}$alkyl; and
B is —$CH_2$— or —O—.

4. The compound of claim 1, or a pharmaceutically acceptable salt thereof, wherein R is selected from the group consisting of:
(1) hydrogen,
(2) halogen,
(3) —O—$C_{1-4}$alkyl,
(4) —NH—$C_{1-2}$alkyl, wherein the —$C_{1-2}$alkyl is substituted with a heterocyclyl; wherein the heterocyclyl is optionally substituted with methyl, ethyl, propyl, —$CH_2Cl$ or —$CH_2CF_3$; and
(5) heterocyclyl, optionally substituted with one to four substituents independently selected from halogen, $C_{1-4}$alkyl, and —O—$C_{1-4}$alkyl;
wherein each occurrence of a heterocyclyl of (4) and (5) is independently selected from the group consisting of 2-azabicyclo[2.2.2]octanyl, 8-azabicyclo[3.2.1]octanyl, 2-azaspiro[3.3]heptanyl, azaindolyl, 1,6-diazaspiro[3.3]heptanyl, 2,3-dihydro-1,4-dioxinyl, 1,4-dioxanyl, hexahydro-3,6-epiminofuro[3,2-b]furanyl, hexahydro-1H-furo[3,4-c]pyrrolyl, imidazolyl, isoxazolyl, morpholinyl, 2-oxa-5-azabicyclo[2.2.1]heptanyl, 6-oxa-3-azabicyclo[3.1.1]heptanyl, 6-oxa-2-azaspiro[3.5]nonanyl, 2-oxa-5-azabicyclo[2.2.2]octanyl, 3-oxa-8-azabicyclo[3.2.1]octanyl, 8-oxa-3-azabicyclo[3.2.1]octanyl, 1-oxa-8-azaspiro[4.5]decanyl, 6-oxa-2-azaspiro[3.4]octanyl, 3-oxa-1,7-diazaspiro[4.4]nonanyl, 3,9-dioxa-7-azabicyclo[3.3.1]nonanyl, oxazolidinyl, piperazinyl, piperidinyl, pyrazolyl, pyridazinyl, pyridinyl, pyrrolyl, tetrahydrofuranyl, and tetrahydropyranyl.

5. The compound of claim 4, or a pharmaceutically acceptable salt thereof, wherein R is selected from the group consisting of:
(1) hydrogen,
(2) —F,
(3) —Cl,
(4) —Br,
(5) —O-methyl,
(6) —O-ethyl,
(7) —NH—$CH_2$-heterocyclyl, wherein the heterocyclyl is substituted with —$CH_2Cl$, and
(8) heterocyclyl, optionally substituted with one to two substituents independently selected from —F, —Cl, methyl, ethyl, propyl, —O-methyl, —O-ethyl, —O-propyl and —O— isopropyl;
wherein each occurrence of a heterocyclyl of (7) and (8) is independently selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl, pyrazolyl, and tetrahydropyranyl.

6. The compound of claim 5, or a pharmaceutically acceptable salt thereof, wherein R is selected from the group consisting of:
(1) hydrogen,
(2) —F,
(3) —Cl,
(4) —Br,
(5) —O-methyl,
(6) —O-ethyl,
(7) —NH—$CH_2$-tetrahydropyranyl, wherein the tetrahydropyranyl is substituted with —$CH_2Cl$, and
(8) heterocyclyl, optionally substituted with one to two substituents independently selected from —Cl, —F, methyl, ethyl, propyl, —O-methyl, —O-ethyl, —O-propyl and —O— isopropyl;
wherein the heterocyclyl is selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl and pyrazolyl.

7. The compound of claim 1, or a pharmaceutically acceptable salt thereof, wherein:
$R^e$ is hydrogen, —F, —Cl, methyl or ethyl; and
each of $R^f$, $R^g$, $R^h$, $R^m$, $R^n$ and $R^p$ is independently selected from the group consisting of:
(1) hydrogen,
(2) —F,
(3) —Cl,
(4) —Br,
(5) methyl,
(6) ethyl,
(7) propyl, and
(8) —$S(O)_2$—$C_{1-2}$alkyl;
with the proviso that when $R^e$ is hydrogen, at least one of $R^f$, $R^g$, $R^h$, $R^m$, $R^n$ and $R^p$ is not hydrogen.

8. The compound of claim 1, or a pharmaceutically acceptable salt thereof, wherein:
$R^e$ is —F, —Cl, methyl or ethyl; and
each of $R^f$, $R^g$, $R^h$, $R^m$, $R^n$ and $R^p$ is hydrogen.

9. The compound of claim 1, or a pharmaceutically acceptable salt thereof, wherein:
A is —CH($R^1$)— or —N($R^2$)—; $R^1$ is selected from the group consisting of hydrogen, methyl, —O— methyl, —O-ethyl, —O-propyl and —O-isopropyl; $R^2$ is selected from the group consisting of hydrogen, —$CH_2CF_3$, and —$S(O)_2$-ethyl;
B is —$CH_2$— or —O—;
R is selected from the group consisting of:
(1) hydrogen,
(2) —F,
(3) —Cl,
(4) —O-methyl,
(5) —O-ethyl,
(6) —NH—$CH_2$-tetrahydropyranyl, wherein the tetrahydropyranyl is substituted with —$CH_2Cl$, and
(7) heterocyclyl, optionally substituted with one to two substituents independently selected from —Cl, —F, methyl, ethyl, propyl, —O-methyl, —O-ethyl, and —O-propyl;

wherein the heterocyclyl is selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl and pyrazolyl;

$R^e$ is hydrogen, —Cl, —F, methyl or ethyl; and each of $R^f$, $R^g$, $R^h$, $R^m$, $R^n$ and $R^p$ is independently selected from the group consisting of:
(1) hydrogen,
(2) —F,
(3) —Cl,
(4) —Br,
(5) methyl,
(6) ethyl,
(7) propyl, and
(8) —S(O)$_2$-methyl;

with the proviso that when $R^e$ is hydrogen, at least one of $R^f$, $R^g$, $R^h$, $R^m$, $R^n$ and $R^p$ is not hydrogen.

10. The compound of claim 1 of formula (Ia), or a pharmaceutically acceptable salt thereof:

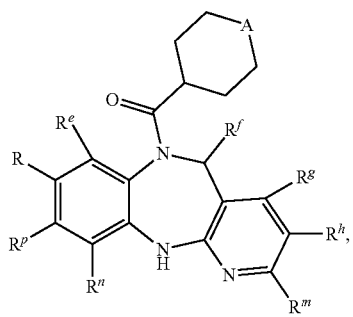

(Ia)

wherein

A is —CH(R$^1$)— or —N(R$^2$)—; R$^1$ is selected from the group consisting of hydrogen, methyl, —O— propyl and —O-isopropyl; R$^2$ is —CH$_2$CF$_3$ or —S(O)$_2$-ethyl;

$R^e$ is hydrogen, —Cl, —F, methyl or ethyl; and each of $R^f$, $R^g$, $R^h$, $R^m$, $R^n$ and $R^p$ is independently selected from the group consisting of:
(1) hydrogen,
(2) —F,
(3) —Cl,
(4) —Br,
(5) methyl,
(6) ethyl,
(7) propyl, and
(8) —S(O)$_2$-methyl;

with the proviso that when $R^e$ is hydrogen, at least one of $R^f$, $R^g$, $R^h$, $R^m$, $R^n$ and $R^p$ is not hydrogen.

11. The compound of claim 10, or a pharmaceutically acceptable salt thereof, wherein:

$R^e$ is —F or methyl; and each of $R^f$, $R^g$, $R^h$, $R^m$, $R^n$ and $R^p$ is hydrogen.

12. The compound of claim 10, or a pharmaceutically acceptable salt thereof, wherein:

$R^e$ is hydrogen;

each of $R^m$ and $R^n$ is hydrogen; and each of $R^f$, $R^g$, $R^h$, and $R^p$ is independently selected from the group consisting of:

(1) hydrogen,
(2) —F,
(3) —Cl,
(4) methyl, and
(5) —S(O)$_2$-methyl;

with the proviso that at least one of $R^f$, $R^g$, $R^h$ and $R^p$ is not hydrogen.

13. The compound of claim 1 of formula (Ib), or a pharmaceutically acceptable salt thereof:

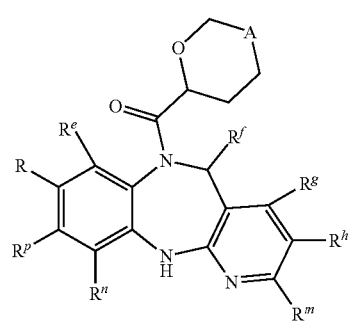

(Ib)

wherein

A is —CH(R$^1$)—; and R$^1$ is —O-propyl or —O-isopropyl;

$R^e$ is hydrogen;

each of $R^f$, $R^g$, $R^m$ and $R^n$ is hydrogen;

each of $R^h$ and $R^p$ is independently selected from the group consisting of:
(1) hydrogen,
(2) —F, and
(3) —Cl;

with the proviso that at least one of $R^h$ and $R^p$ is not hydrogen; and

R is a heterocyclyl selected from the group consisting of 2-azabicyclo[2.2.2]octanyl, 8-azabicyclo[3.2.1]octanyl, 1,4-dioxanyl, hexahydro-3,6-epiminofuro[3,2-b]furanyl, morpholinyl, 2-oxa-5-azabicyclo[2.2.1]heptanyl, 6-oxa-2-azaspiro[3.5]nonanyl, 2-oxa-5-azabicyclo[2.2.2]octanyl, 3,9-dioxa-7-azabicyclo[3.3.1]nonanyl, oxazolidinyl and pyrazolyl.

14. The compound of claim 1 selected from the group consisting of:

(8-Chloro-3-fluoro-5,11-dihydro-6H-benzo[b]pyrido[2,3-e][1,4]diazepin-6-yl)(1-(2,2,2-trifluoroethyl)piperidin-4-yl)methanone, (8-Chloro-3-fluoro-5,11-dihydro-6H-benzo[b]pyrido[2,3-e][1,4]diazepin-6-yl)(trans-4-isopropoxycyclohexyl)methanone, (8-Bromo-3-fluoro-5,11-dihydro-6H-benzo[b]pyrido[2,3-e][1,4]diazepin-6-yl)(trans-4-isopropoxycyclohexyl)methanone, (8-Chloro-3,9-difluoro-5,11-dihydro-6H-benzo[b]pyrido[2,3-e][1,4]diazepin-6-yl)(trans-4-isopropoxycyclohexyl)methanone, (8-Chloro-3,9-difluoro-5,11-dihydro-6H-benzo[b]pyrido[2,3-e][1,4]diazepin-6-yl)(1-(2,2,2-trifluoroethyl)piperidin-4-yl)methanone, (8-((1 S,4S)-2-Oxa-5-azabicyclo[2.2.1]heptan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone, (3-Fluoro-8-((3R,3aR,6R,6aR)-hexahydro-3,6-epiminofuro[3,2-b]furan-7-yl)-5,11-dihydro-6H-benzo[b]

pyrido[2,3-e][1,4]diazepin-6-yl)(1-(2,2,2-trifluoro-ethyl)piperidin-4-yl)methanone,
(8-(2-Oxa-5-azabicyclo[2.2.2]octan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone,
(8-(2-Oxa-5-azabicyclo[2.2.2]octan-5-yl)-3-fluoro-5,11-dihydro-6H-benzo[b]pyrido[2,3-e][1,4]diazepin-6-yl)(1-(2,2,2-trifluoroethyl)piperidin-4-yl)methanone,
(3-Fluoro-8-((1R,3r,5 S)-3-methoxy-8-azabicyclo[3.2.1]octan-8-yl)-5,11-dihydro-6H-benzo[b]pyrido[2,3-e][1,4]diazepin-6-yl)(1-(2,2,2-trifluoroethyl)piperidin-4-yl)methanone,
(8-((2S,5 S)-2,5-Dimethylmorpholino)-3-fluoro-5,11-dihydro-6H-benzo[b]pyrido[2,3-e][1,4]diazepin-6-yl)(1-(2,2,2-trifluoroethyl)piperidin-4-yl)methanone,
(3-Fluoro-8-(6-oxa-2-azaspiro[3.5]nonan-2-yl)-5,11-dihydro-6H-benzo[b]pyrido[2,3-e][1,4]diazepin-6-yl)(1-(2,2,2-trifluoroethyl)piperidin-4-yl)methanone,
[3-Fluoro-8-(2-oxa-5-azabicyclo[2.2.2]oct-5-yl)-5,11-dihydro-6H-pyrido[2,3-b][1,5]benzodiazepin-6-yl][trans-4-(propan-2-yloxy)cyclohexyl]methanone,
[3-Fluoro-8-(2-oxa-5-azabicyclo[2.2.2]oct-5-yl)-5,11-dihydro-6H-pyrido[2,3-b][1,5]benzodiazepin-6-yl][trans-4-(propan-2-yloxy)cyclohexyl]methanone,
(8-((1R,5 S)-3,9-Dioxa-7-azabicyclo[3.3.1]nonan-7-yl)-3-fluoro-5,11-dihydro-6H-benzo[b]pyrido[2,3-e][1,4]diazepin-6-yl)(1-(2,2,2-trifluoroethyl)piperidin-4-yl)methanone,
[3-Fluoro-8-(6-oxa-2-azaspiro[3.5]non-2-yl)-5,11-dihydro-6H-pyrido[2,3-b][1,5]benzodiazepin-6-yl][trans-4-(propan-2-yloxy)cyclohexyl]methanone,
(3-Fluoro-8-((3R,3aR,6R,6aR)-hexahydro-3,6-epiminofuro[3,2-b]furan-7-yl)-5,11-dihydro-6H-benzo[b]pyrido[2,3-e][1,4]diazepin-6-yl)(trans-4-isopropoxycyclohexyl)methanone,
(8-((1 S,4S)-2-Oxa-5-azabicyclo[2.2.1]heptan-5-yl)-3-fluoro-5,11-dihydro-6H-benzo[b]pyrido[2,3-e][1,4]diazepin-6-yl)(trans-4-isopropoxycyclohexyl)methanone,
(8-((1 S,4S)-2-Oxa-5-azabicyclo[2.2.1]heptan-5-yl)-3-fluoro-5,11-dihydro-6H-benzo[b]pyrido[2,3-e][1,4]diazepin-6-yl)(cis-4-isopropoxycyclohexyl)methanone,
(8-((1 S,4S)-2-Oxa-5-azabicyclo[2.2.1]heptan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone,
(3,9-Difluoro-8-(6-oxa-2-azaspiro[3.5]nonan-2-yl)-5,11-dihydro-6H-benzo[b]pyrido[2,3-e][1,4]diazepin-6-yl)(1-(2,2,2-trifluoroethyl)piperidin-4-yl)methanone,
(3,9-Difluoro-8-((3R,3 aR,6R,6aR)-hexahydro-3,6-epiminofuro[3,2-b]furan-7-yl)-5,11-dihydro-6H-benzo[b]pyrido[2,3-e][1,4]diazepin-6-yl)(1-(2,2,2-trifluoroethyl)piperidin-4-yl)methanone,
(8-((2S,5 S)-2,5-Dimethylmorpholino)-3,9-difluoro-5,11-dihydro-6H-benzo[b]pyrido[2,3-e][1,4]diazepin-6-yl)(1-(2,2,2-trifluoroethyl)piperidin-4-yl)methanone,
{3,9-Difluoro-8-[(1 S,4S)-2-oxa-5-azabicyclo[2.2.1]hept-5-yl]-5,11-dihydro-6H-pyrido[2,3-b][1,5]benzodiazepin-6-yl}[trans-4-(propan-2-yloxy)cyclohexyl]methanone,
[3,9-Difluoro-8-(6-oxa-2-azaspiro[3.5]non-2-yl)-5,11-dihydro-6H-pyrido[2,3-b][1,5]benzodiazepin-6-yl][trans-4-(propan-2-yloxy)cyclohexyl]methanone,
[3,9-Difluoro-8-(3-oxa-8-azabicyclo[3.2.1]oct-8-yl)-5,11-dihydro-6H-pyrido[2,3-b][1,5]benzodiazepin-6-yl][trans-4-(propan-2-yloxy)cyclohexyl]methanone,
(8-((1 S,4S)-2-Oxa-5-azabicyclo[2.2.1]heptan-5-yl)-9-fluoro-5,11-dihydro-6H-benzo[b]pyrido[2,3-e][1,4]diazepin-6-yl)(1-(2,2,2-trifluoroethyl)piperidin-4-yl)methanone,
(9-Fluoro-8-((3R,3 aR,6R,6aR)-hexahydro-3,6-epiminofuro[3,2-b]furan-7-yl)-5,11-dihydro-6H-benzo[b]pyrido[2,3-e][1,4]diazepin-6-yl)(1-(2,2,2-trifluoroethyl)piperidin-4-yl)methanone,
(8-(2-Oxa-5-azabicyclo[2.2.2]octan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone,
(3,9-Difluoro-8-((1R,3r,5 S)-3-methoxy-8-azabicyclo[3.2.1]octan-8-yl)-5,11-dihydro-6H-benzo[b]pyrido[2,3-e][1,4]diazepin-6-yl)(1-(2,2,2-trifluoroethyl)piperidin-4-yl)methanone,
(8-((1R,4R)-2-Oxa-5-azabicyclo[2.2.2]octan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone,
(8-((1 S,4S)-2-Oxa-5-azabicyclo[2.2.2]octan-5-yl)-3,9-difluoro-5,11-dihydro-6H-benzo[b]pyrido[2,3-e][1,4]diazepin-6-yl)(1-(2,2,2-trifluoroethyl)piperidin-4-yl)methanone,
(8-((S)-1,4-Dioxan-2-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone,
(8-((R)-1,4-dioxan-2-yl)-3-fluoro-5,11-dihydro-6H-benzo[b]pyrido[2,3-e][1,4]diazepin-6-yl)((2R,5S)-5-isopropoxytetrahydro-2H-pyran-2-yl)methanone,
(8-(1,4-Dioxan-2-yl)-3,9-difluoro-5H-benzo[b]pyrido[2,3-e][1,4]diazepin-6(11H)-yl)((2R,5 S)-5-isopropoxytetrahydro-2H-pyran-2-yl)methanone,
(8-(1,4-Dioxan-2-yl)-9-fluoro-5,11-dihydro-6H-benzo[b]pyrido[2,3-e][1,4]diazepin-6-yl)((2R,5 S)-5-isopropoxytetrahydro-2H-pyran-2-yl)methanone,
(8-(1,4-Dioxan-2-yl)-9-fluoro-5,11-dihydro-6H-benzo[b]pyrido[2,3-e][1,4]diazepin-6-yl)((2R,5 S)-5-isopropoxytetrahydro-2H-pyran-2-yl)methanone,
(3-Fluoro-8-((1R,3 S,5 S)-3-methoxy-8-azabicyclo[3.2.1]octan-8-yl)-5,11-dihydro-6H-benzo[b]pyrido[2,3-e][1,4]diazepin-6-yl)((2R,5 S)-5-isopropoxytetrahydro-2H-pyran-2-yl)methanone,
(3-Fluoro-8-(6-oxa-2-azaspiro[3.5]nonan-2-yl)-5,11-dihydro-6H-benzo[b]pyrido[2,3-e][1,4]diazepin-6-yl)((2R,5 S)-5-isopropoxytetrahydro-2H-pyran-2-yl)methanone,
(8-((1R,5 S)-3,9-Dioxa-7-azabicyclo[3.3.1]nonan-7-yl)-3-fluoro-5,11-dihydro-6H-benzo[b]pyrido[2,3-e][1,4]diazepin-6-yl)((2R,5 S)-5-isopropoxytetrahydro-2H-pyran-2-yl)methanone,
(8-(((3-(Chloromethyl)tetrahydro-2H-pyran-3-yl)methyl)amino)-3-fluoro-5,11-dihydro-6H-benzo[b]pyrido[2,3-e][1,4]diazepin-6-yl)((2R,5 S)-5-isopropoxytetrahydro-2H-pyran-2-yl)methanone,
(8-(2-Oxa-5-azabicyclo[2.2.2]octan-5-yl)-3-fluoro-5,11-dihydro-6H-benzo[b]pyrido[2,3-e][1,4]diazepin-6-yl)(1-(ethylsulfonyl)piperidin-4-yl)methanone,
(8-(2-Oxa-5-azabicyclo[2.2.2]octan-5-yl)-3,9-difluoro-5,11-dihydro-6H-benzo[b]pyrido[2,3-e][1,4]diazepin-6-yl)((2R,5 S)-5-isopropoxytetrahydro-2H-pyran-2-yl)methanone,
(3,9-Difluoro-8-(6-oxa-2-azaspiro[3.5]nonan-2-yl)-5H-benzo[b]pyrido[2,3-e][1,4]diazepin-6(11H)-yl)((2R,5 S)-5-isopropoxytetrahydro-2H-pyran-2-yl)methanone, (8-((1 S,4S)-2-Oxa-5-azabicyclo[2.2.1]heptan-5-yl)-3,9-difluoro-5,11-dihydro-6H-benzo[b]pyrido[2,3-e][1,4]diazepin-6-yl)((2R,5 S)-5-isopropoxytetrahydro-2H-pyran-2-yl)methanone, (3,9-Difluoro-8-((1R,3 S,5 S)-3-methoxy-8-azabicyclo[3.2.1]octan-8-yl)-5,11-dihydro-6H-benzo[b]pyrido[2,3-e][1,4]diazepin-6-yl)((2R,5 S)-5-isopropoxytetrahydro-2H-pyran-2-yl)methanone, (8-((1R,4R)-2-Oxa-5-azabicyclo[2.2.2]octan-5-yl)-3-fluoro-5,11-dihydro-6H-benzo[b]pyrido[2,3-e][1,4]diazepin-6-yl)((2R,5 S)-5-isopropoxytetrahydro-2H-pyran-2-yl)methanone, (8-((1 S,4S)-2-Oxa-5-azabicyclo[2.2.2]octan-5-yl)-3-fluoro-5,11-dihydro-6H-benzo[b]pyrido[2,3-e][1,4]diazepin-6-yl)((2R,5 S)-5-isopropoxytetrahydro-2H-pyran-2-yl)methanone, (3,9-Difluoro-8-(1-methyl-1H-pyrazol-5-yl)-5,11-dihydro-6H-benzo[b]pyrido[2,3-e][1,4]diazepin-6-yl)(1-(2,2,2-trifluoroethyl)piperidin-4-yl)methanone, (3,9-Difluoro-8-(1H-pyrazol-5-yl)-5,11-dihydro-6H-benzo[b]pyrido[2,3-e][1,4]diazepin-6-yl)(1-(2,2,2-trifluoroethyl)piperidin-4-yl)methanone, (9-Fluoro-8-(1-methyl-1H-pyrazol-4-yl)-5,11-dihydro-6H-benzo[b]pyrido[2,3-e][1,4]diazepin-6-yl)(1-(2,2,2-trifluoroethyl)piperidin-4-yl)methanone, (9-Fluoro-8-(1-methyl-1H-pyrazol-5-yl)-5,11-dihydro-6H-benzo[b]pyrido[2,3-e][1,4]diazepin-6-yl)(1-(2,2,2-trifluoroethyl)piperidin-4-yl)methanone, (S)-(8-(1,4-Dioxan-2-yl)-3-fluoro-5,11-dihydro-6H-benzo[b]pyrido[2,3-e][1,4]diazepin-6-yl)(1-(2,2,2-trifluoroethyl)piperidin-4-yl)methanone, (R)-(8-(1,4-Dioxan-2-yl)-3-fluoro-5,11-dihydro-6H-benzo[b]pyrido[2,3-e][1,4]diazepin-6-yl)(1-(2,2,2-trifluoroethyl)piperidin-4-yl)methanone, (R)-(8-(1,4-Dioxan-2-yl)-9-fluoro-5,11-dihydro-6H-benzo[b]pyrido[2,3-e][1,4]diazepin-6-yl)(1-(2,2,2-trifluoroethyl)piperidin-4-yl)methanone, (S)-(8-(1,4-Dioxan-2-yl)-9-fluoro-5,11-dihydro-6H-benzo[b]pyrido[2,3-e][1,4]diazepin-6-yl)(1-(2,2,2-trifluoroethyl)piperidin-4-yl)methanone, (Trans-4-isopropoxycyclohexyl){9-methyl-8-[(1S,4S)-2-oxa-5-azabicyclo[2.2.2]oct-5-yl]-5,11-dihydro-6H-pyrido[2,3-b][1,5]benzodiazepin-6-yl}methanone, (Trans-4-isopropoxycyclohexyl){7-methyl-8-[(1S,4S)-2-oxa-5-azabicyclo[2.2.2]oct-5-yl]-5,11-dihydro-6H-pyrido[2,3-b][1,5]benzodiazepin-6-yl}methanone, (Trans-4-isopropoxycyclohexyl){9-methyl-8-[(1R,4R)-2-oxa-5-azabicyclo[2.2.2]oct-5-yl]-5,11-dihydro-6H-pyrido[2,3-b][1,5]benzodiazepin-6-yl}methanone, (Trans-4-isopropoxycyclohexyl){7-methyl-8-[(1R,4R)-2-oxa-5-azabicyclo[2.2.2]oct-5-yl]-5,11-dihydro-6H-pyrido[2,3-b][1,5]benzodiazepin-6-yl}methanone,

[9-Fluoro-8-(2-oxa-5-azabicyclo[2.2.2]oct-5-yl)-5,11-dihydro-6H-pyrido[2,3-b][1,5]benzodiazepin-6-yl](trans-4-isopropoxycyclohexyl)methanone,

[7-Fluoro-8-(2-oxa-5-azabicyclo[2.2.2]oct-5-yl)-5,11-dihydro-6H-pyrido[2,3-b][1,5]benzodiazepin-6-yl](trans-4-isopropoxycyclohexyl)methanone, (8-((1 S,4S)-2-Oxa-5-azabicyclo[2.2.1]heptan-5-yl)-9-fluoro-5H-benzo[b]pyrido[2,3-e][1,4]diazepin-6(11H)-yl)((2R,5 S)-5-isopropoxytetrahydro-2H-pyran-2-yl)methanone, (8-Chloro-5-methyl-5,11-dihydro-6H-benzo[b]pyrido[2,3-e][1,4]diazepin-6-yl)(trans-4-isopropoxycyclohexyl)methanone, (Trans-4-isopropoxycyclohexyl)(5-methyl-8-morpholino-5,11-dihydro-6H-benzo[b]pyrido[2,3-e][1,4]diazepin-6-yl)methanone, (8-Methoxy-5-methyl-5,11-dihydro-6H-benzo[b]pyrido[2,3-e][1,4]diazepin-6-yl)(1-(2,2,2-trifluoroethyl)piperidin-4-yl)methanone, (Trans-4-isopropoxycyclohexyl)(8-methoxy-5-methyl-5,11-dihydro-6H-benzo[b]pyrido[2,3-e][1,4]diazepin-6-yl)methanone, (8-((1 S,4S)-2-Oxa-5-azabicyclo[2.2.2]octan-5-yl)-3-methyl-5,11-dihydro-6H-benzo[b]pyrido[2,3-e][1,4]diazepin-6-yl)(trans-4-isopropoxycyclohexyl)methanone, (8-((1 S,4S)-2-Oxa-5-azabicyclo[2.2.2]octan-5-yl)-3-(methylsulfonyl)-5,11-dihydro-6H-benzo[b]pyrido[2,3-e][1,4]diazepin-6-yl)(trans-4-isopropoxycyclohexyl)methanone, (8-((1 S,4S)-2-Oxa-5-azabicyclo[2.2.2]octan-5-yl)-3-chloro-5,11-dihydro-6H-benzo[b]pyrido[2,3-e][1,4]diazepin-6-yl)(trans-4-isopropoxycyclohexyl)methanone, (3,9-Difluoro-5,11-dihydro-6H-benzo[b]pyrido[2,3-e][1,4]diazepin-6-yl)(1-(2,2,2-trifluoroethyl)piperidin-4-yl)methanone, (8-(2-Oxa-5-azabicyclo[2.2.2]octan-5-yl)-3,9-difluoro-5H-benzo[b]pyrido[2,3-e][1,4]diazepin-6(11H)-yl)(1-(2,2,2-trifluoroethyl)piperidin-4-yl)methanone, and (9-Fluoro-5,11-dihydro-6H-benzo[b]pyrido[2,3-e][1,4]diazepin-6-yl)(1-(2,2,2-trifluoroethyl)piperidin-4-yl)methanone, or a pharmaceutically acceptable salt thereof.

15. A composition which comprises an inert carrier and a compound of claim 1, or a pharmaceutically acceptable salt thereof.

16. A method for treating a disease or disorder associated with mutant IDH enzyme activity in a mammalian subject in need thereof, which comprises administering to the subject an effective amount of a compound of claim 1, or a pharmaceutically acceptable salt thereof.

17. A method for treating a disease or disorder associated with mutant IDH enzyme activity in a mammalian subject which comprises B administering to the subject an effective amount of a compound of claim 1, or a pharmaceutically B acceptable salt thereof n combination with another anti-cancer agent.

18. The method of claim 16, wherein the disease or disorder associated with mutant IDH enzyme activity is a cancer selected from the group consisting of glioma, glioblastoma multiforme, paraganglioma, supratentorial primordial neuroectodermal tumors, acute myeloid leukemia (AML), breast cancer, prostate cancer, thyroid cancer, colon cancer, chondrosarcoma, cholangiocarcinoma, peripheral T-cell lymphoma, and melanoma.

19. The method of claim 18, wherein the cancer is selected from glioma, glioblastoma multiforme, acute myeloid leukemia and breast cancer.

* * * * *